United States Patent
De Man et al.

(10) Patent No.: US 11,832,979 B2
(45) Date of Patent: Dec. 5, 2023

(54) SYSTEMS AND METHODS FOR A STATIONARY CT IMAGING SYSTEM

(71) Applicant: GE Precision Healthcare LLC, Milwaukee, WI (US)

(72) Inventors: Bruno Kristiaan Bernard De Man, Clifton Park, NY (US); Jed Douglas Pack, Glenville, NY (US); Mingye Wu, Clifton Park, NY (US); Chad Allan Smith, Franklin, WI (US); Jean-Baptiste Thibault, Brookfield, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 24 days.

(21) Appl. No.: 17/342,324

(22) Filed: Jun. 8, 2021

(65) Prior Publication Data
US 2021/0378618 A1    Dec. 9, 2021

Related U.S. Application Data

(60) Provisional application No. 63/036,162, filed on Jun. 8, 2020, provisional application No. 63/036,272, filed
(Continued)

(51) Int. Cl.
*A61B 6/00*        (2006.01)
*A61B 6/03*        (2006.01)
(Continued)

(52) U.S. Cl.
CPC ............ *A61B 6/4266* (2013.01); *A61B 6/032* (2013.01); *A61B 6/0407* (2013.01); *A61B 6/06* (2013.01);
(Continued)

(58) Field of Classification Search
CPC ..... A61B 6/4266; A61B 6/032; A61B 6/0407; A61B 6/06; A61B 6/4007; A61B 6/4014; A61B 6/4078; A61B 6/4275; A61B 6/4405; A61B 6/4411; A61B 6/4452; A61B 6/4476; A61B 6/5264; A61B 6/5282; G06T 7/20; G06T 11/003; G06T 11/006; G06T 2207/10081; G06T 2207/20081;
(Continued)

(56) References Cited

U.S. PATENT DOCUMENTS 6,735,274 B1 * 5/2004 Zahavi ................. A61B 6/4028
378/4
2005/0226363 A1 * 10/2005 Edie ..................... A61B 6/4275
378/9
(Continued)

*Primary Examiner* — Courtney D Thomas
(74) *Attorney, Agent, or Firm* — McCoy Russell LLP

(57) ABSTRACT

Various methods and systems are provided for stationary CT imaging. In one embodiment, an imaging system comprises a stationary distributed x-ray source unit comprising a plurality of emitters positioned to emit x-ray beams through the imaging volume, one or more detector arrays extending around at least a portion of an imaging volume, each detector array comprising a plurality of detector elements, each detector element configured to receive x-ray beams from more than one emitter, and an anti-scatter device configured to be positioned between one or more emitters of the plurality of emitters and an object in the imaging volume.

20 Claims, 30 Drawing Sheets

Related U.S. Application Data on Jun. 8, 2020, provisional application No. 63/036,203, filed on Jun. 8, 2020, provisional application No. 63/039,071, filed on Jun. 15, 2020, provisional application No. 63/039,181, filed on Jun. 15, 2020.

(51) Int. Cl.
  *G06T 11/00*   (2006.01)
  *A61B 6/06*    (2006.01)
  *A61B 6/04*    (2006.01)
  *G06T 7/20*    (2017.01)

(52) U.S. Cl.
  CPC .......... *A61B 6/4007* (2013.01); *A61B 6/4014* (2013.01); *A61B 6/4078* (2013.01); *A61B 6/4275* (2013.01); *A61B 6/4405* (2013.01); *A61B 6/4411* (2013.01); *A61B 6/4452* (2013.01); *A61B 6/4476* (2013.01); *A61B 6/5264* (2013.01); *A61B 6/5282* (2013.01); *G06T 7/20* (2013.01); *G06T 11/003* (2013.01); *G06T 11/006* (2013.01); *G06T 2207/10081* (2013.01); *G06T 2207/20081* (2013.01); *G06T 2207/30004* (2013.01); *G06T 2211/40* (2013.01); *G06T 2211/412* (2013.01)

(58) Field of Classification Search
  CPC ....... G06T 2207/30004; G06T 2211/40; G06T 2211/412
  See application file for complete search history.

(56) References Cited

U.S. PATENT DOCUMENTS

| | | | |
|---|---|---|---|
| 2006/0023832 A1* | 2/2006 | Edic | A61B 6/4014 378/7 |
| 2019/0261930 A1* | 8/2019 | Wang | A61B 6/4014 |

* cited by examiner

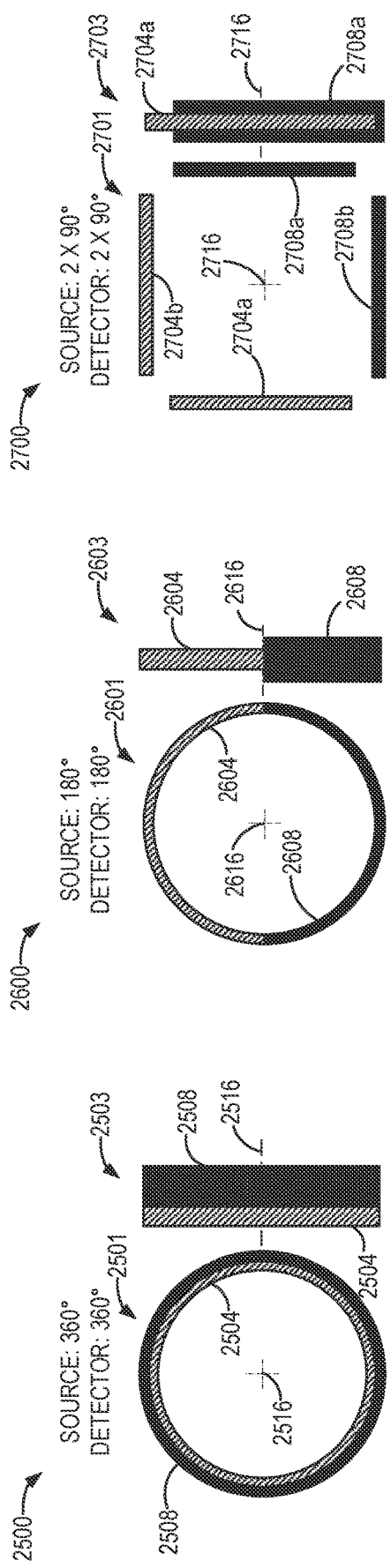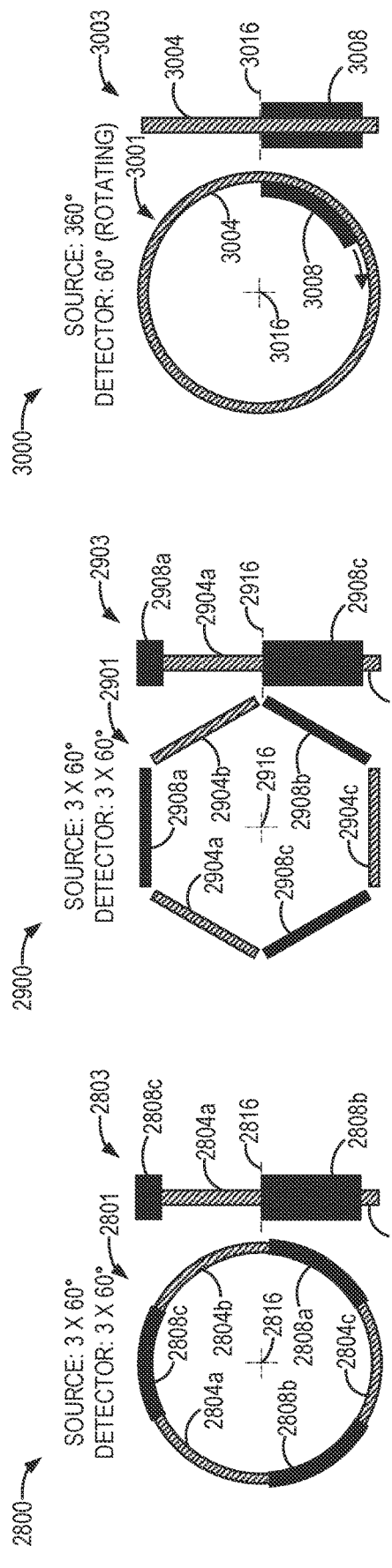

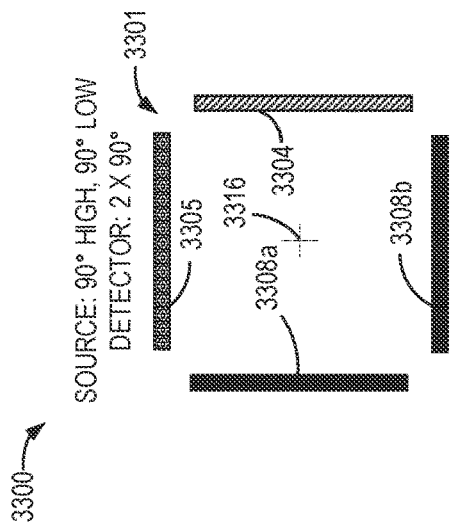
FIG. 31
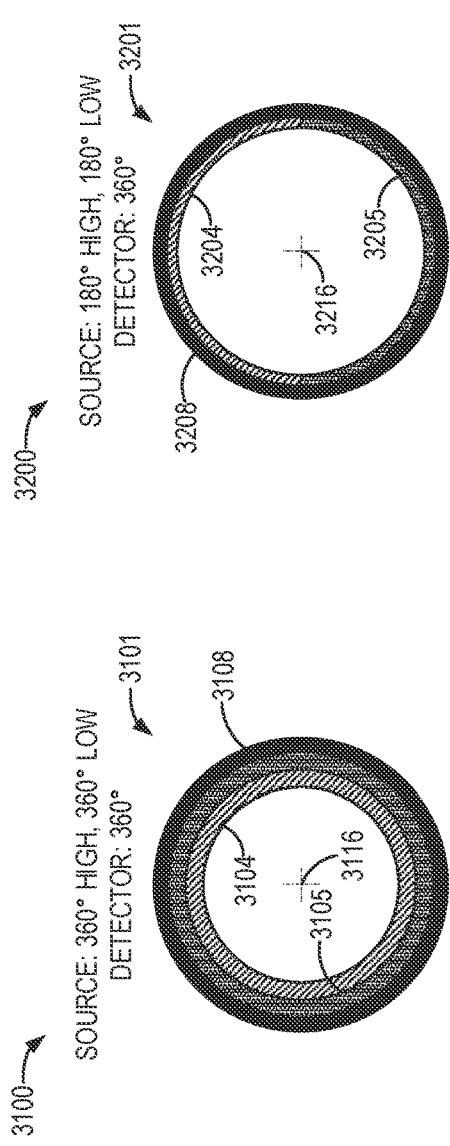
FIG. 32
FIG. 33
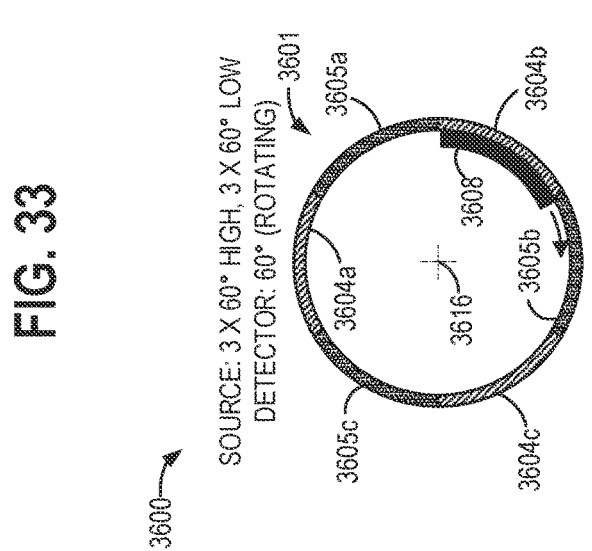
FIG. 34
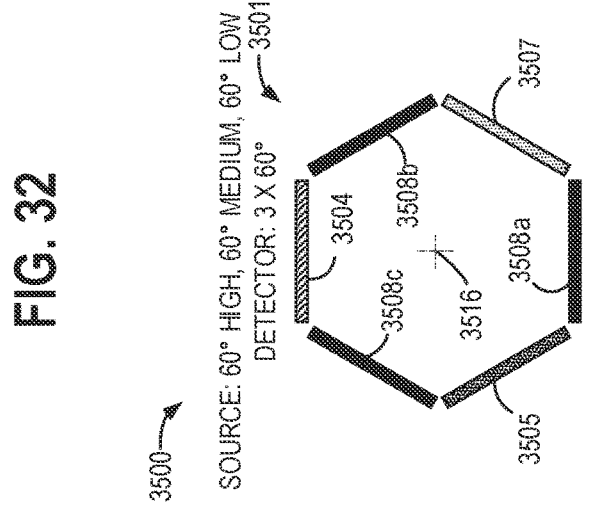
FIG. 35
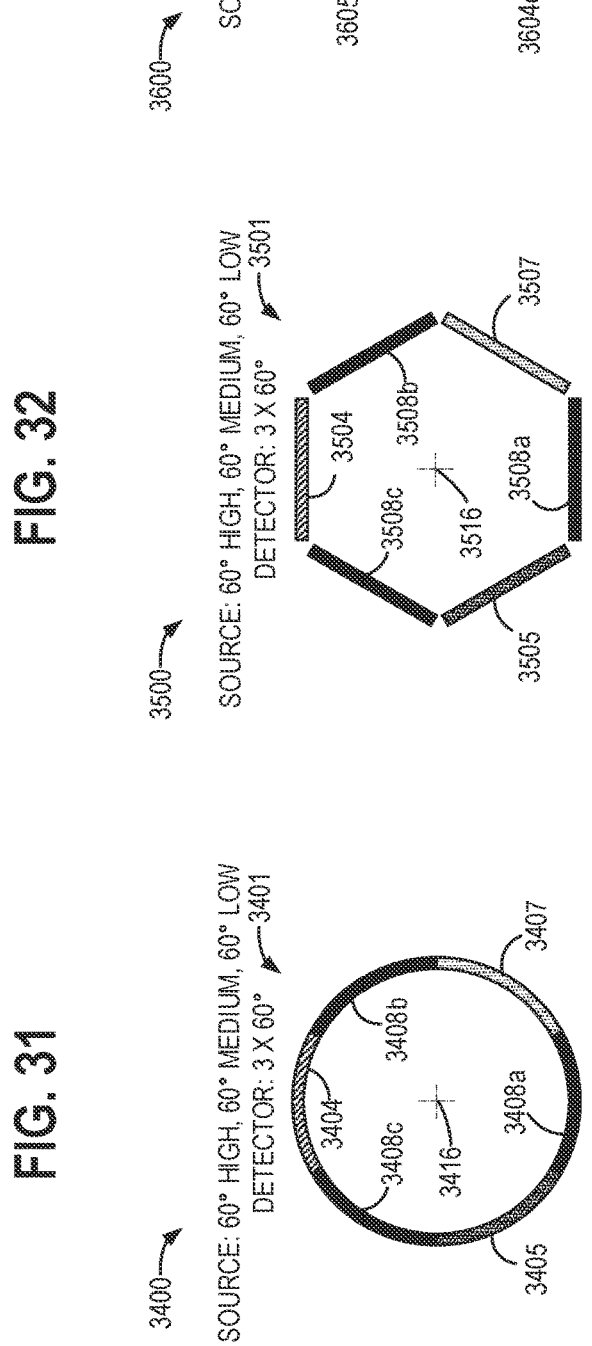
FIG. 36

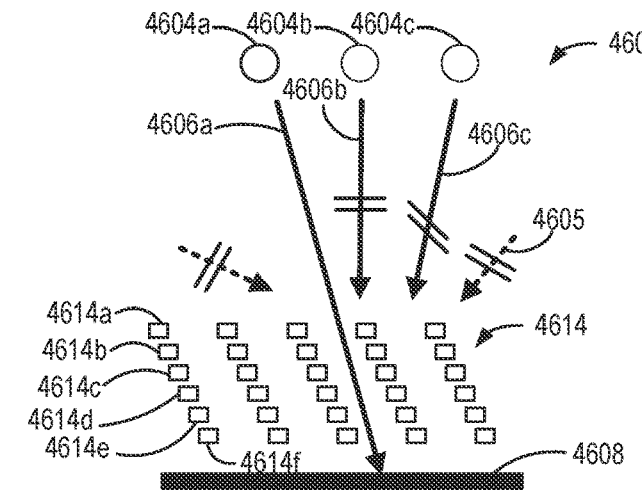
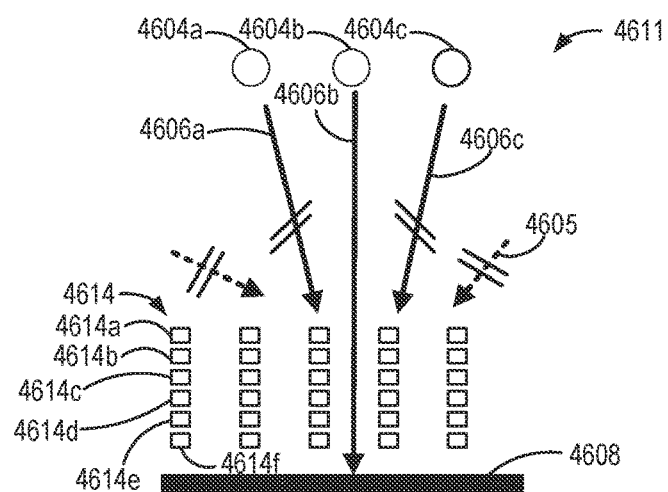
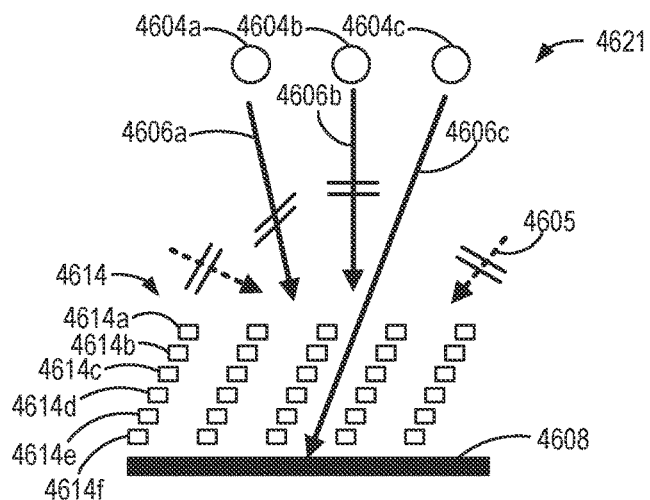
FIG. 46

SYSTEMS AND METHODS FOR A STATIONARY CT IMAGING SYSTEM

CROSS REFERENCE TO RELATED APPLICATIONS

This application claims priority to U.S. Provisional Patent Application No. 63/036,162, titled "A TRANSPORTABLE AND AUTONOMOUS STATIONARY CT IMAGING SYSTEM," and filed Jun. 8, 2020; U.S. Provisional Patent Application No. 63/036,272, titled "AN UPRIGHT STATIONARY CT IMAGING SYSTEM AND IMAGE RECONSTRUCTION FOR SAME," and filed Jun. 8, 2020; U.S. Provisional Patent Application No. 63/036,203, titled "A DISTRIBUTED X-RAY SOURCE FOR AN IMAGING SYSTEM," and filed Jun. 8, 2020; U.S. Provisional Patent Application No. 63/039,071, titled "A STATIONARY CT IMAGING SYSTEM AND SCATTERED X-RAY RADIATION," and filed Jun. 15, 2020; and U.S. Provisional Patent Application No. 63/039,181, titled "A MULTI-ENERGY STATIONARY CT IMAGING SYSTEM," and filed Jun. 15, 2020. The entire contents of each of the above-identified applications is hereby incorporated by reference for all purposes.

FIELD

Embodiments of the subject matter disclosed herein relate to computed tomography (CT) imaging, and more particularly to a stationary CT imaging system.

BACKGROUND

Computed tomography (CT) imaging systems enable fast, non-invasive imaging of a variety of tissues, including bone, soft tissue, etc., as well as high contrast detection that allows CT imaging systems to visualize contrast agents. However, conventional CT imaging systems rely on complex and tightly controlled rotating gantries that support one or more x-ray sources and one or more detector arrays. Accordingly, conventional CT imaging systems are expensive, large, heavy, and difficult to install, which limits the environments in which CT imaging systems may be utilized.

BRIEF DESCRIPTION

This summary introduces concepts that are described in more detail in the detailed description. It should not be used to identify essential features of the claimed subject matter, nor to limit the scope of the claimed subject matter.

In one aspect, a stationary computed tomography (CT) system includes a stationary distributed x-ray source unit comprising a plurality of emitters positioned to emit x-ray beams through the imaging volume, one or more detector arrays extending around at least a portion of an imaging volume, each detector array comprising a plurality of detector elements, each detector element configured to receive x-ray beams from more than one emitter, and an anti-scatter device configured to be positioned between one or more emitters of the plurality of emitters and an object in the imaging volume. In this way, the stationary CT system may be used to non-invasively image a subject without relying on moving parts, particularly a rotating gantry, and thus may be smaller and lighter weight, expanding the environments in which the CT system may be deployed. However, because the stationary CT system includes detector elements that receive attenuated x-ray beams from more than one emitter, conventional anti-scatter grids that are positioned between the detector elements and the subject cannot be utilized in the stationary CT system. As such, projection data obtained by the stationary CT system may include a relatively large amount of scattered x-ray beams, which may result in noisy images. By including an anti-scatter grid between the object and one or more of the emitters, scatter may be reduced by reducing the angular range of the x-ray beams or breaking each x-ray beam into a series of narrower beams, for example.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 25 schematically shows a first exemplary single energy distributed x-ray source and detector configuration for an imaging unit, according to an embodiment.

FIG. 26 schematically shows a second exemplary single energy distributed x-ray source and detector configuration for an imaging unit, according to an embodiment.

FIG. 27 schematically shows a third exemplary single energy distributed x-ray source and detector configuration for an imaging unit, according to an embodiment.

FIG. 28 schematically shows a fourth exemplary single energy distributed x-ray source and detector configuration for an imaging unit, according to an embodiment.

FIG. 29 schematically shows a fifth exemplary single energy distributed x-ray source and detector configuration for an imaging unit, according to an embodiment.

FIG. 30 schematically shows a sixth exemplary single energy distributed x-ray source and detector configuration for an imaging unit, according to an embodiment.

FIG. 31 schematically shows a first exemplary multi-energy distributed x-ray source and detector configuration for an imaging unit, according to an embodiment.

FIG. 32 schematically shows a second exemplary multi-energy distributed x-ray source and detector configuration for an imaging unit, according to an embodiment.

FIG. 33 schematically shows a third exemplary multi-energy distributed x-ray source and detector configuration for an imaging unit, according to an embodiment.

FIG. 34 schematically shows a fourth exemplary multi-energy distributed x-ray source and detector configuration for an imaging unit, according to an embodiment.

FIG. 35 schematically shows a fifth exemplary multi-energy distributed x-ray source and detector configuration for an imaging unit, according to an embodiment.

FIG. 36 schematically shows a sixth exemplary multi-energy distributed x-ray source and detector configuration for an imaging unit, according to an embodiment.

FIG. 46 schematically shows a multi-layer aperture device for an imaging unit, according to an embodiment.

FIGS. 2-7 and 9-21 are shown approximately to scale, although other relative dimensions may be used, if desired.

DETAILED DESCRIPTION

Embodiments of the present disclosure will now be described, by way of example, with reference to the FIGS. 1-57, which relate to various embodiments for stationary computed tomography (CT) imaging systems.

Figure 1:
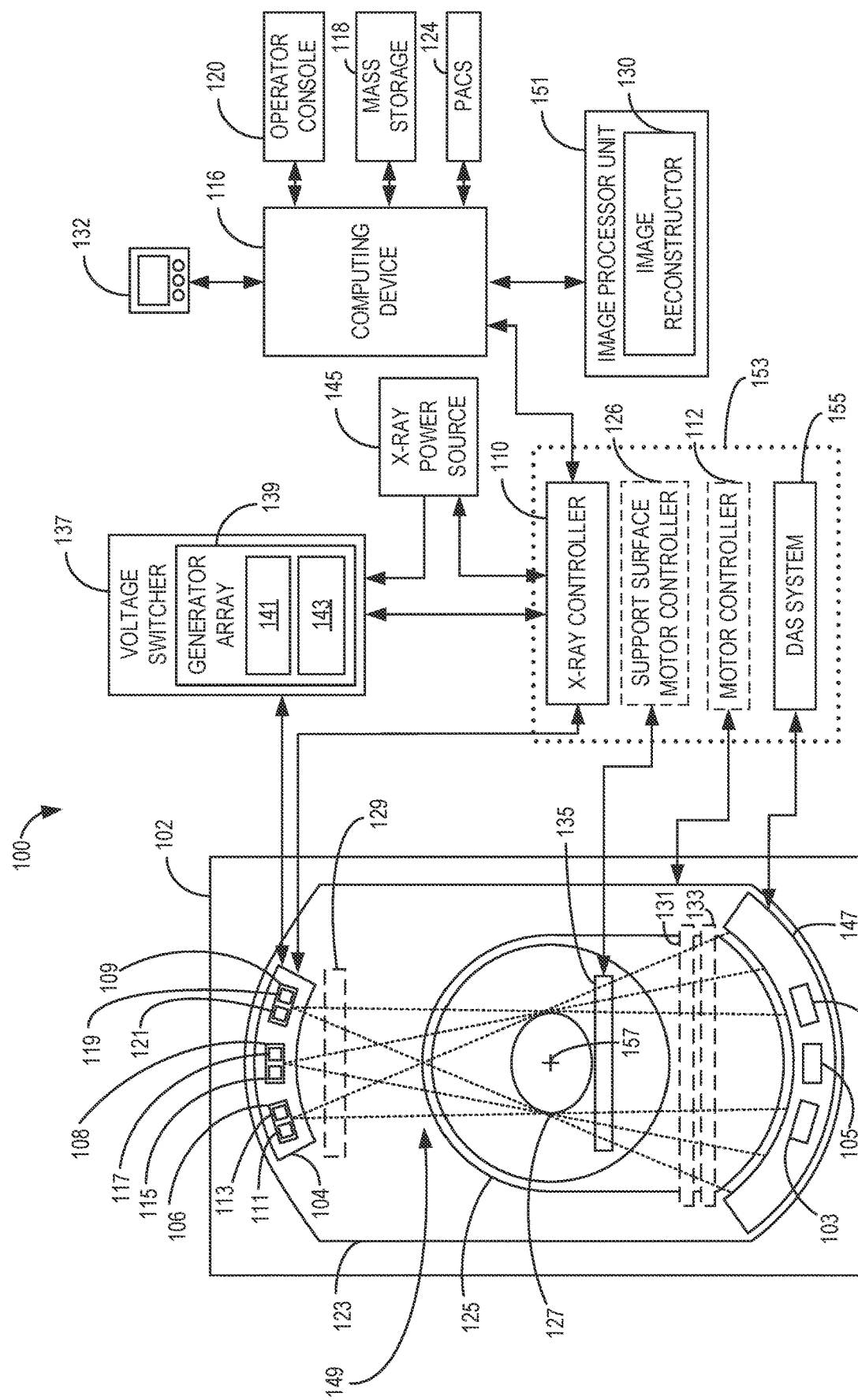
FIG. 1 shows a block schematic diagram of an exemplary imaging system, according to an embodiment.

FIG. 1 illustrates an exemplary imaging system 100 configured for CT imaging. Particularly, the imaging system 100 is configured to image a subject 127. Subject 127 may be a patient, an inanimate object, one or more manufactured parts, and/or foreign objects such as dental implants, stents, and/or contrast agents present within the body. In one embodiment, the imaging system 100 includes a frame 102, which in turn, may further include at least one distributed x-ray source unit 104 configured to project x-ray radiation for use in imaging the subject 127 supported by a support surface 135. Specifically, the distributed x-ray source unit 104 is configured to project x-ray radiation beams 149 towards a detector array 147 positioned on the opposite side of the frame 102, with the detector array 147 including a plurality of x-ray detectors (e.g., detector cells) such as a detector 103, a detector 105, a detector 107, etc. Although FIG. 1 depicts only a single distributed x-ray source unit 104 and a single detector array 147, in certain embodiments, multiple distributed x-ray source units and detector arrays may be employed to project x-ray radiation beams for acquiring projection data. Although FIG. 1 depicts the detector array 147 as including three detectors (e.g., the detector 103, the detector 105, and the detector 107), in some embodiments, the detector array 147 and/or other detector arrays may include a different number of detectors (e.g., four, five, ten, etc.). Further, although FIG. 1 depicts the distributed x-ray source unit 104 as including three individual x-ray emitters such as an emitter 106, an emitter 108, and an emitter 109, in some embodiments, the distributed x-ray source unit 104 and/or other distributed x-ray source units may include a different number of x-ray emitters (e.g., four, five, ten, etc.).

The detectors of the detector array 147 sense the x-ray radiation beams 149 that pass through the subject 127 to acquire corresponding projection data. In some embodiments, one or more of the detectors of the imaging system 100 (e.g., the detectors of detector array 147) may be a different type of detector relative to other detectors of the imaging system 100. For example, the detectors of the detector array 147 (e.g., the detector 103, the detector 105, the detector 107, etc.) may be energy-integrating detectors, energy-discriminating detectors, photon-counting detectors, multiple resolution detectors (e.g., higher resolution detectors or lower resolution detectors), multiple dimension detectors (e.g., larger detectors covering a larger area or smaller detectors covering a smaller area), scintillator-based detectors, direct-conversion detectors, etc., or some combination thereof (e.g., the detector 103 may be an energy-integrating detector and the detector 105 may be a photon-counting detector, the detector 105 may be a lower resolution detector and the detector 107 may be a higher resolution detector, etc.). In some embodiments, the distributed x-ray source unit 104 may enable dual-energy gemstone spectral imaging (GSI) by rapid peak kilovoltage (kVp) switching. In some embodiments, the x-ray detectors employed are photon-counting detectors that are capable of differentiating x-ray photons of different energies. In other embodiments, two sets of x-ray sources and detectors are used to generate dual-energy projections, with one set at a low kVp and the other at a high kVp. It may thus be appreciated that the methods described herein may be implemented with single energy acquisition techniques as well as dual (or multiple) energy acquisition techniques.

Each x-ray emitter of the distributed x-ray source unit 104 includes a respective anode and a respective cathode. For example, the emitter 106 includes an anode 111 and a cathode 113, the emitter 108 includes an anode 115 and a cathode 117, and the emitter 109 includes an anode 121 and a cathode 119. Electrons emitted by the cathodes (e.g., resulting from energization of the cathodes) may be intercepted by the respective anodes. Electrons intercepted by the anodes may release energy in the form of x-rays, with the x-rays being directed toward the detector array 147. An area of each anode surface that receives the electrons from the respective cathode and forms the emitted x-rays may be referred to herein as a "focal spot." In some embodiments, one or more of the anodes may be rotating anodes configured to rotate around an axis extending between the anodes and respective cathodes (e.g., the anode 111 may rotate around an axis extending between the anode 111 and cathode 113). The rotation of the anodes may reduce a heating of the anodes by the electrons emitted by the respective cathodes (e.g., rotation of the anodes may increase an effective surface area of the anodes coming into contact with the electrons emitted by the cathodes). However, in other embodiments, the anodes may not be rotating anodes.

In certain embodiments, the imaging system 100 further includes an image processor unit 151 with an image reconstructor 130 configured to reconstruct images of a target volume of the subject 127 using an iterative or analytic image reconstruction method. For example, the image reconstructor 130 may use an analytic image reconstruction approach such as filtered back projection (FBP) to reconstruct images of a target volume of the patient. As another example, the image reconstructor 130 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 127. As described further herein, in some examples, the image reconstructor 130 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector of the detector array produces a separate electrical signal that is a measurement of the x-ray beam attenuation at the detector location. The attenuation measurements from all the detectors are acquired separately to produce a transmission profile.

In the examples described herein, the distributed x-ray source units and the detector arrays are arranged within an imaging plane around the object to be imaged. In this configuration, beams of x-ray radiation from the distributed x-ray source units intersect the object (e.g., the subject 127) at different angles, with the beams being intercepted by the detectors of the detector arrays. For example, a given beam of x-ray radiation may pass through the subject 127 and may be attenuated by the subject 127, and the attenuated beam may then be intercepted by the detectors of the detector arrays. x-ray radiation attenuation measurements (e.g., projection data) acquired by a given detector may be associated with a given beam of x-ray radiation intercepted by the detector at a given angle and may be referred to herein as a "view" (e.g., each beam intercepted by the detector may be projected toward the detector at a different angle and may correspond to a different view). A "scan" of the object includes a set of views made at different angles, or view angles. For example, a scan of the object may include one or more views acquired by a first detector and one or more views acquired by a second detector, where an angle of a given beam of x-ray radiation to the first detector may be different than an angle of the given beam to the second detector. The term "view" as used herein is not limited to the use as described above with respect to projection data from one frame angle. The term "view" is used to mean one data acquisition whenever there are multiple data acquisitions from different angles.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection (FBP) technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient may be moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present disclosure in which data representing an image is generated but a viewable image is not. Therefore, as used herein, the term "image" broadly refers to both viewable images and data representing a viewable image. However, many embodiments generate (or are configured to generate) at least one viewable image.

In some embodiments, each detectors array, such as detector array 147, is fabricated in a multi-slice configuration including a plurality of rows of detectors (e.g., the detector 103, the detector 105, the detector 107, etc.). In such a configuration, one or more additional rows of the detectors are arranged in a parallel configuration for acquiring the projection data.

As the distributed x-ray source unit 104 and the detector array 147 collects data of the attenuated x-ray beams, the data collected by the detector array 147 undergoes pre-processing and calibration to condition the data to represent the line integrals of the attenuation coefficients of the scanned subject 127. The processed data are commonly called projections.

In some examples, the individual detectors of the detector array 147 (e.g., the detector 103, the detector 105, the detector 107, etc.) may be photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 100 reveals internal features of the subject 127, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 100 includes a control mechanism 153 to control movement of components such as the support surface 135 and the operation of the distributed x-ray source unit 104. The control mechanism 153 may further include an x-ray controller 110 configured to provide power and timing signals to the distributed x-ray source unit 104. Additionally, the control mechanism 153 may include a support surface motor controller 126 configured to control a translation speed and/or position of the support surface 135 based on a desired imaging configuration.

In certain embodiments, the control mechanism 153 further includes a data acquisition system (DAS) 155 configured to sample analog data received from the detectors of the detector array 147 and convert the analog data to digital signals for subsequent processing. The DAS 155 may be further configured to selectively aggregate analog data from a subset of the detectors of the detector array 147 into so-called macro-detectors, as described further herein. The data sampled and digitized by the DAS 155 is transmitted to a computer or computing device 116. In one example, the computing device 116 stores the data in a storage device or mass storage 118. The mass storage 118, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 116 provides commands and parameters to one or more of the DAS 155, the x-ray controller 110, and the support surface motor controller 126 for controlling system operations such as data acquisition and/or processing. In certain embodiments, the computing device 116 controls system operations based on operator input. The computing device 116 receives the operator input, for example, including commands and/or scanning parameters via an operator console 120 operatively coupled to the computing device 116. The operator console 120 may include a keyboard (not shown) or a touchscreen to allow the operator to specify the commands and/or scanning parameters.

Although FIG. 1 illustrates only one operator console 120, more than one operator console may be coupled to the imaging system 100, for example, for inputting or outputting system parameters, requesting examinations, plotting data, and/or viewing images. Further, in certain embodiments, the imaging system 100 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 100 either includes, or is coupled to, a picture archiving and communications system (PACS) 124. In an exemplary implementation, the PACS 124 is further coupled to a remote system such as a radiology department information system, hospital information system, and/or to an internal or external network (not shown) to allow operators at different locations to supply commands and parameters and/or gain access to the image data.

The computing device 116 uses the operator-supplied and/or system-defined commands and parameters to operate support surface motor controller 126, which in turn, may control a position of the support surface 135. Specifically, the support surface motor controller 126 may move the support surface 135 for appropriately positioning the subject 127 within an opening 125 for acquiring projection data corresponding to the target volume of the subject 127.

As previously noted, the DAS 155 samples and digitizes the projection data acquired by the detectors of the detector array 147. Subsequently, the image reconstructor 130 uses the sampled and digitized x-ray data to perform high-speed reconstruction. Although FIG. 1 illustrates the image reconstructor 130 as a separate entity, in certain embodiments, the image reconstructor 130 may form part of the computing device 116. Alternatively, the image reconstructor 130 may be absent from the imaging system 100 and instead the computing device 116 may perform one or more functions of the image reconstructor 130. Moreover, the image reconstructor 130 may be located locally or remotely, and may be operatively connected to the imaging system 100 using a wired or wireless network. Particularly, one exemplary embodiment may use computing resources in a "cloud" network cluster for the image reconstructor 130.

In one embodiment, the image reconstructor 130 stores the images reconstructed in the mass storage 118. Alternatively, the image reconstructor 130 may transmit the reconstructed images to the computing device 116 for generating useful patient information for diagnosis and evaluation. In certain embodiments, the computing device 116 may transmit the reconstructed images and/or the patient information to a display or display device 132 communicatively coupled to the computing device 116 and/or the image reconstructor 130. In some embodiments, the reconstructed images may be transmitted from the computing device 116 or the image reconstructor 130 to the mass storage 118 for short-term or long-term storage.

In some embodiments, the imaging system 100 may include a voltage switcher 137 configured to control energization of emitters of the imaging system 100 (e.g., the emitter 106, the emitter 108, the emitter 109, etc.). The voltage switcher 137 may include a generator array 139 comprising one or more generators, such as a generator 141, a generator 143, etc. Although FIG. 1 shows the generator array 139 including two generators, in some embodiments, the voltage switcher and generator array may include a different number of generators (e.g., one, three, four, etc.). In some examples, one or more of the generators may be dynamic resonance energy-recovery (DRER) generators configured to recover electrical charge stored on the capacitances of the imaging system 100 (e.g., charge stored on cables, anodes, etc. of the imaging system 100).

The voltage switcher 137 is electronically coupled to an x-ray power source 145. In some embodiments, the x-ray power source 145 may be a stationary power source, such as an electrical power supply of a medical facility housing the imaging system 100. In other embodiments, the x-ray power source 145 may be a mobile electrical power source, such as a battery or an array of batteries. The x-ray power source 145 is configured to provide electrical power to the emitters of the imaging system 100 via the x-ray controller 110 and/or the voltage switcher 137. For example, in embodiments that do not include the voltage switcher 137, the x-ray emitters of the imaging system 100 may receive electrical power (e.g., electrical current) from the x-ray power source 145 via the x-ray controller 110 (e.g., the x-ray controller 110 may be configured to control an energization timing and/or energization amount of the x-ray emitters). In other embodiments, the x-ray emitters may receive electrical power from the x-ray power source 145 via one or both of the x-ray controller 110 and the voltage switcher 137. For example, the x-ray controller 110 may control an operating mode of the distributed x-ray source unit 104 (e.g., adjust the distributed x-ray source unit 104 between an "ON" mode wherein one or more emitters of the distributed x-ray source unit 104 are energized, and an "OFF" mode in which none of the emitters of the distributed x-ray source unit 104 are energized), and the voltage switcher 137 may control an amount of energization of one or more of the emitters independent of the other emitters (e.g., the voltage switcher 137 may control a voltage of the emitter 106 and the emitter 108 separately, such that the emitter 106 may be operated at a first voltage and the emitter 108 may be operated at a different, second voltage).

The voltage switcher 137 may control the energization of the x-ray emitters by adjusting the amount and/or timing of the energization to individual emitters. As one example, one or more emitters of the distributed x-ray source unit 104 may be configured to operate at a different voltage relative to other emitters of the distributed x-ray source unit 104 (e.g., the emitter 106 may be configured to operate at a different voltage compared to the emitter 108). The generator 141 may be configured to energize one or more of the emitters of the distributed x-ray source unit 104 at a first voltage (e.g., 0 kVp, with the respective cathode maintained at −50 kVp), and the generator 143 may be configured to energize one or more of the emitters of the distributed x-ray source unit 104 at a different, second voltage (e.g., 50 kVp, with the respective cathode maintained at −50 kVp). As another example, the anodes of the emitters may be maintained at a given voltage (e.g., 90 kVp), and the first generator 141 and/or the second generator 143 may adjust the voltage of each respective cathode in order to adjust the electrical potential difference between the anodes and cathodes, where the adjustment for a given emitter may be different compared to at least one other emitter (e.g., the anodes of both of the emitter 106 and the emitter 108 may be maintained at 90 kVp, and the voltage switcher may adjust the cathodes between −50 kVp and 0 kVp independently of each other, as one example).

As another example, one or more of the emitters of the distributed x-ray source unit 104 may be configured to operate in different energization modes, with the voltage switcher 137 configured to adjust the emitters between the different energization modes (e.g., the emitter 106 may be configured to operate in a higher, first voltage mode or a lower, second voltage mode, with the voltage switcher 137 configured to adjust the emitter 106 between the first voltage mode and the second voltage mode). For example, in configurations in which one or more of the generators is configured as a DRER generator as described above, a switching speed (e.g., adjustment speed) of the emitters between the different energization modes may be increased. As another example, one or more of the emitters may include two or more anodes, and the anodes may be configured to operate at different voltages. The two or more anodes may intercept electrons emitted by a single cathode, or in some examples the one or more emitters including the two or more anodes may include two or more respective cathodes. As another example, the imaging system 100 includes the distributed x-ray source unit 104 along with one or more additional distributed x-ray source units. The emitters of different distributed x-ray source units may be configured to operate at different voltages (e.g., the distributed x-ray source unit 104, which may be referred to as a first distributed x-ray source unit, includes emitters that may be operated at a first voltage, and a second distributed x-ray source unit of the imaging system may include emitters configured to operate at a different, second voltage).

In some examples, one or more of the emitters of the distributed x-ray source units of the imaging system 100 (e.g., distributed x-ray source unit 104) may be sized differently relative to other emitters of the imaging system 100. For example, the emitter 106 may be larger than the emitter 108 (e.g., the anode 111 may be larger than the anode 115). Larger emitters (e.g., focal spots) may increase a signal-to-noise ratio of images acquired by the imaging system 100. However, smaller emitters may increase a spatial resolution of the images acquired by the imaging system 100. Images acquired by emitters having the larger size may be reconstructed into one image, and images acquired by emitters having the smaller size may be reconstructed into a different, second image. The resulting low-noise and high-resolution images may then be combined using a deep learning network, in some examples.

In some examples, one or more of the emitters of the distributed x-ray source unit 104 may be formed of two or more different materials, where each material is configured to emit x-ray radiation at different energy levels (e.g., different frequencies). For example, the emitter 106 may include the cathode 113 configured to emit electrons to the anode 111, where the anode 111 includes at least two different materials configured to intercept the electrons emitted by the cathode 113. During conditions in which the electrons are intercepted by the portion of the anode 111 including a first material, the anode 111 may emit x-ray radiation with a first energy (e.g., a first wavelength), and during conditions in which the electrons are intercepted by a portion of the anode 111 including a different, second material, the anode 111 may emit x-ray radiation with a different, second energy (e.g., a second wavelength). In some examples, the anode 111 may be rotated via the x-ray controller 110 in order to control whether the electrons emitted by the cathode 113 are intercepted by the portion of the anode 111 formed by the first material or the portion of the anode 111 formed by the second material in order to control the energy of the x-ray radiation emitted by the anode 111. Although the emitter 106 is described above as an example, in other examples one or more of the emitter 108, the emitter 109, or other emitters of the imaging system 100 may include a similar configuration (e.g., a configuration including an anode having two or more materials that may intercept electrons emitted by a respective cathode). In some examples, the anodes may include other materials such as one or more diamond layers and/or phase-change materials, in addition to the materials described above.

As described above, the imaging system 100 includes the distributed x-ray source unit 104 and may further include additional distributed x-ray source units. In some embodiments, the x-ray emitters of a given distributed x-ray source unit may be maintained at a different voltage relative to the x-ray emitters of at least one other distributed x-ray source unit. For example, the emitter 106, the emitter 108, and the emitter 109 of the distributed x-ray source unit 104 may each be maintained at a first voltage, and emitters of a second distributed x-ray source unit may be maintained at a different, second voltage. In embodiments in which the imaging system includes four or more distributed x-ray source units, distributed x-ray source units that are arranged adjacent to each other may have emitters that are maintained at different voltages. For example, in a configuration that includes four distributed x-ray source units arranged around a central axis of the imaging system, a first distributed x-ray source unit may be arranged at a first position, a second distributed x-ray source unit may be arranged at a second position in a clockwise direction around the central axis from the first distributed x-ray source unit, a third distributed x-ray source unit may be arranged at a third position in the clockwise direction around the central axis from the second distributed x-ray source unit, and a fourth distributed x-ray source unit may be arranged at a fourth position in the clockwise direction around the central axis from the third distributed x-ray source unit. The first distributed x-ray source unit and the third distributed x-ray source unit may each include x-ray emitters maintained at a first voltage (e.g., 90 kVp), and the second distributed x-ray source unit and fourth distributed x-ray source unit may each include x-ray emitters maintained at a second voltage (e.g., 140 kVp). As another example, the imaging system may include a first plurality of distributed x-ray source units arranged around the central axis (e.g., encircling the central axis) at a first location along the central axis, and a second plurality of distributed x-ray source units arranged around the central axis at a different, second location along the central axis (e.g., where the second location is spaced apart from the first location). The first plurality of distributed x-ray source units may include emitters maintained at the first voltage, and the second plurality of distributed x-ray source units may include emitters maintained at the second voltage. Other examples are possible.

The imaging system 100 includes the frame 102 and an imaging unit 123, where the imaging unit 123 may comprise a gantry having the opening 125 and includes the distributed x-ray source units (e.g., the distributed x-ray source unit 104) and the detectors arrays (e.g., the detector array 147). In some embodiments (e.g., similar to the example described below with reference to FIGS. 2-3), the imaging unit 123 may be a stationary imaging unit 123 configured to image the subject 127 without rotation or translation. For example, the imaging unit 123 may include a plurality of distributed x-ray source units and a plurality of detector arrays arranged around a central axis 157. The subject 127 to be imaged may be positioned along the central axis 157 such that the subject 127 is encircled by the distributed x-ray source units and the detector arrays, and the distributed x-ray source units may project x-ray beams through the subject 127 toward the detectors arrays for imaging the subject 127 without moving (e.g., rotating, translating, etc.) relative to the subject 127. The imaging system 100 may reconstruct images of the subject 127 via the image reconstructor 130 according to the methods described herein (e.g., via a deep learning network).

In some embodiments (e.g., similar to the example described below with reference to FIGS. 4-5), the imaging system may include the motor controller 112 configured to adjust a translation of the imaging unit 123. For example, the subject 127 to be imaged may be arranged vertically in an upright position (e.g., with a base, or feet, of the subject 127 arranged toward a ground surface upon which the imaging system 100 sits, and with a top, or head, of the subject 127 arranged away from the ground surface), and the motor controller 112 may translate the imaging unit 123 in the vertical direction during imaging of the subject 127 (e.g., during a scan of the subject 127). Although the motor controller 112 may translate the imaging unit 123, the motor controller 112 does not rotate the imaging unit 123. Moving the imaging unit 123 via the motor controller 112 may be performed during a chest scan of the subject 127, for example, and may increase an amount of the subject 127 imaged by the imaging system 100. In order to provide for a wide angle range of imaging of the subject 127 (e.g., 180 degrees around the subject, 270 degrees around the subject, 360 degrees around the subject, etc.) without rotation of the imaging unit 123, the distributed x-ray source units and the detectors of the imaging system are arranged around the axis of translation of the imaging unit 123. The image reconstructor 130 may provide views of the subject 127 through the wide angle range using the images acquired by the detectors according to the methods described herein (e.g., via a deep learning network).

In some embodiments, the selection and orientation of the distributed x-ray source units and detectors may be based on an anatomy of the subject 127 to be imaged. For example, the imaging system 100 may be configured with the distributed x-ray source units and detectors in an arrangement providing increased imaging quality for imaging a particular anatomical feature of the subject 127 (e.g., chest, head, etc.). As one example, the distributed x-ray source units and detectors may be arranged to provide increased imaging quality for imaging of the chest of the subject 127 by reducing distortion resulting from an inward and outward motion of the chest as the patient breathes. As another example, the distributed x-ray source units and detectors may be arranged to provide increased imaging quality for imaging of the head of the patient by reducing distortion resulting from a side-to-side movement of the head of the subject 127. In yet other examples, the distributed x-ray source units and detectors may be arranged to reduce a power consumption of the imaging system 100 (e.g., reduce a path length between the distributed x-ray source units and the respective detectors). As yet another example, the distributed x-ray source units and detectors may be arranged to reduce an x-ray dosage to particular anatomical features (e.g., reduce an amount of x-rays directed toward posterior features of the subject while imaging anterior features of the subject). In some examples, the spacing and positioning of the x-ray emitters and the detectors may be configured to increase a sampling density of the imaging system 100 by interlacing conjugate x-ray beams.

The imaging system 100 may further include a plurality of components arranged between the distributed x-ray source units (e.g., the distributed x-ray source unit 104) and the detector arrays (e.g., the detector array 147), with the components configured to adjust one or more characteristics of the beams of x-rays emitted by the distributed x-ray source units and/or received by the detectors of the detector arrays. For example, imaging system 100 may include a filter array 129, where the filter array 129 comprises one or more filters configured to adjust an energy of the x-ray beams emitted by the distributed x-ray source units. As one example, the filter array 129 may include a first filter configured to filter x-ray energy in a first range emitted by the distributed x-ray source units (e.g., below 50 keV). In some examples, the filter array 129 may include one or more additional filters, such as a second filter configured to filter x-ray energy in a second range emitted by the distributed x-ray source units (e.g., below 70 keV). In some examples, the filters of the filter array 129 may be positioned to filter x-ray beams emitted by pre-determined emitters of the imaging system (e.g., the filters of the filter array 129 may filter all of the x-ray beams emitted by the emitters or only x-ray beams emitted by a pre-determined set of the emitters). As one example, the filters of the filter array 129 may be configured to filter the beams of x-ray radiation emitted by the emitters of the distributed x-ray source unit 104 and may not be configured to filter beams of x-ray radiation emitted by other emitters of other distributed x-ray source units of the imaging system. As another example, the filters may be configured to filter beams of x-ray radiation emitted by one or more emitters of the distributed x-ray source unit 104 and may be configured to not filter beams of x-ray radiation emitted by at least one emitter of the distributed x-ray source unit 104.

In yet other examples, a position of the filter array 129 may be adjustable in order to adjust which emitters of the imaging system are filtered by the filters of the filter array. For example, the filter array 129 may be adjustable from a first position in which beams of x-ray radiation emitted by the emitter 106 and the emitter 109 are filtered by the filters of the filter array 129 (e.g., a position in which the filters of the filter array absorb x-rays emitted by the emitter 106 and emitter 109 at a particular energy range) to a second position in which beams of x-ray radiation emitted by the emitter 106 and the emitter 109 are not filtered by the filters of the filter array 129. As another example, a given emitter of the imaging system may be filtered by either a first filter or a second filter of the filter array 129, with the filter array 129 being adjustable to arrange either or both of the first filter or the second filter into position to filter the x-ray beams emitted by the given emitter. In some embodiments, the filter array may be arranged on an annulus, and the annulus may be configured to rotate to provide different filtration characteristics for different emitters, similar to the examples described further below.

The imaging system 100 may include an anti-scatter grid 131 in some embodiments. The anti-scatter grid 131 is configured to reduce an amount of scattered x-ray radiation intercepted by the detectors. For example, the emitter 106 may emit a beam of x-ray radiation in the direction of the detector 107. The anti-scatter grid 131 may be configured to permit x-ray radiation projected from the emitter 106 directly toward the detector 107 to be intercepted by the detector 107, while x-ray radiation scattered in directions not directly toward the detector 107 may be absorbed by the anti-scatter grid 131. In this configuration, the anti-scatter grid 131 may intercept scattered x-ray radiation and increase an imaging quality of the imaging system 100. In some examples, the anti-scatter grid 131 may be rotatable relative to the detectors in order to adjust a radiation absorbing characteristic of the anti-scatter grid 131 (e.g., to adjust the direction in which x-ray radiation may pass through the anti-scatter grid 131 to the detectors). In some examples, the anti-scatter grid 131 may include a plurality of partitions and may be configured to permit x-ray radiation to pass between adjacent partitions in directions parallel with the adjacent partitions. The positions of the partitions may be individually adjustable (e.g., via the control mechanism 153) in order to control the direction at which x-ray radiation may pass through the anti-scatter grid 131 for interception by the detectors.

The imaging system 100 may include a multi-layer aperture device 133 configured to control the direction of x-ray radiation intercepted by the detectors. The multi-layer aperture device 133 may be included in addition to the anti-scatter grid 131 described above, or the imaging system 100 may include the multi-layer aperture device 133 without the anti-scatter grid 131. The multi-layer aperture device 133 may include a plurality of rows (e.g., layers) of partitions, where the partitions may be similar to the partitions included by the anti-scatter grid 131. However, each row of partitions may be rotatable and/or translatable independently of each other row of partitions. For example, a first row of partitions may initially be aligned with a second row of partitions (e.g., each partition of the first row may be arranged parallel and along a same axis as a respective partition of the second row). The partitions of the first row may be shifted (e.g., translated) together relative to the partitions of the second row in order to adjust an alignment of openings (e.g., apertures) formed between the partitions of the first row with openings formed between the partitions of the second row.

Adjusting the alignment of the openings may adjust a direction at which x-ray radiation may pass through the multi-layer aperture device 133, similar to the examples described further below. For example, in a first configuration, the multi-layer aperture device 133 may allow x-ray radiation to pass through the openings of the multi-layer aperture device 133 in a first direction at a first angle (e.g., 0 degrees) relative to an axis extending between a given emitter and a given detector, with the multi-layer aperture device 133 arranged between the given emitter and the given detector. In a second configuration, the multi-layer aperture device 133 may allow x-ray radiation to pass through the openings in a second direction at a second angle (e.g., 30 degrees) relative to the axis extending between the given emitter and the given detector while blocking x-ray radiation projected in the first direction. Other configurations (e.g., other angles) are possible. The multi-layer aperture device 133 may thus control the direction of x-ray radiation intercepted by the detectors (e.g., in order to reduce absorption of scattered radiation by the detectors).

As described above, the imaging unit 123 of the imaging system 100 may be translated in some embodiments via the motor controller 112 (e.g., moved during imaging of the subject 127). However, in some embodiments, the motor controller 112 may be omitted and the imaging unit 123 may be stationary (e.g., not moved during imaging of the subject 127). As one example, similar to the example described below with reference to FIGS. 2-3, the imaging system 100 may be configured as a stationary imaging system including a plurality of distributed x-ray source units (e.g., distributed x-ray source unit 104) and a plurality of detectors (e.g., detector 103, detector 105, detector 107, etc. of detector array 147) arranged around central axis 157, with imaging of the subject 127 occurring without movement (e.g., translation, rotation, etc.) of the distributed x-ray source units or detectors.

Although the imaging system 100 is shown including the imaging unit 123 and the frame 102 as separate components, in some embodiments the imaging unit 123 and frame 102 may be a single, unitary piece. Further, in some embodiments (e.g., similar to the example described below with reference to FIGS. 2-3), the imaging unit 123 and the frame 102 may be a single structure formed (e.g., assembled) as a result of coupling a plurality of distributed x-ray source units (e.g., the distributed x-ray source unit 104) with a plurality of detector arrays (e.g., the detector array 147). For example, the distributed x-ray source units and/or detector arrays may include brackets or other fastening components configured to couple the distributed x-ray source units together with the detector arrays, with coupled distributed x-ray source units and detector arrays forming a rigid and self-supporting structure which may be referred to the frame and/or imaging unit of the imaging system. Further, the coupling of the distributed x-ray source units and detector arrays may be releasable such that the distributed x-ray source units and detector arrays may be decoupled from each other to disassemble the imaging system (e.g., disassemble the self-supporting structure formed by the distributed x-ray source units and detector arrays). The example of the distributed x-ray source units and detector arrays configured to couple to each other to form the self-supporting structure may be referred to herein as a modular configuration, where each module comprises either a single distributed x-ray source unit or a single detector array.

The various methods and processes (such as the methods described below with reference to FIGS. 51-55) described further herein may be stored as executable instructions in non-transitory memory on a computing device (or controller) in imaging system 100, such as the computing device 116. In one embodiment, the image reconstructor 130 may include such executable instructions in non-transitory memory, and may apply the methods described herein to reconstruct an image from scanning data. In another embodiment, the computing device 116 may include the instructions in non-transitory memory, and may apply the methods described herein, at least in part, to a reconstructed image after receiving the reconstructed image from the image reconstructor 130. In yet another embodiment, the methods and processes described herein may be distributed across the image reconstructor 130 and the computing device 116.

In one embodiment, the display device 132 allows the operator to evaluate the imaged anatomy. The display device 132 may also allow the operator to select a volume of interest (VOI) and/or request patient information, for example, via a graphical user interface (GUI) for a subsequent scan or processing. In some examples, the display device 132 may be a monitor or touchscreen. In other examples, the display device 132 may be a headset. For example, the display device 132 may be a headset configured with a virtual reality display and/or augmented reality display and may be configured to display images of the imaged subject 127 acquired by the imaging system 100 layered onto a real-time anatomical view of the subject 127 (e.g., the headset may display a view of the subject 127 in real time, with images acquired by the imaging system 100 arranged virtually on top of, or adjacent to, the real-time view of the subject 127).

Thus, imaging system 100 provides an example of a stationary CT system that may eliminate or reduce the number of moving parts relative to tradition CT systems with rotating gantries. Such stationary CT systems may be lightweight and, at least in some configurations, portable and/or modular. The stationary CT system may enable deployment of the CT system in environments that traditionally could not support a CT imaging system, such as field hospitals. For example, forward deployed military field hospitals (e.g., Role-2 and Role-3 military treatment facilities) typically have access to two-dimensional (2D) x-ray radiography capabilities, which are helpful in identifying injuries. However, radiographs offer limited low contrast detectability and can only detect large attenuation contrasts, with limited or no visibility of bleeds, lacerations, or ruptures. Moreover, the projection nature of radiographs makes it difficult for precise localization, geometric interpretation and quantitation of injuries.

CT imaging systems or scanners would be the imaging modality of choice to image almost all battlefield indications, since they quickly and non-invasively provide detailed three-dimensional (3D) images of bone, soft tissues, and foreign bodies. The 3D imaging capability offers all possible information, from which advanced artificial intelligence (AI) algorithms can extract a wealth of information. However, conventional CT scanners have been found to be impractical to deploy with field hospitals because they are large, heavy, difficult to transport and install, and lack robustness for a battlefield environment. Even the smallest whole-body CT scanners available today weigh several hundreds of pounds and include a high-precision rotating gantry. This makes their transportation, installation, and maintenance impractical in forwardly deployed field environments where mobility and ease-of-use are desired. Furthermore, the power that is used to operate a conventional CT scanner uses a dedicated generator to supply at least 150 kVA of peak power.

There is a clinical opportunity to quickly deploy CT scanners in rugged environments, such as near battle fronts, coupled with autonomous operation and diagnosis. Today, these environments are limited to 2D x-ray radiography systems since 3D CT imaging systems or scanners are too complex, hard to transport, and not robust.

There is a desire for fast assessment of casualties where immediate patient care is performed, as in forward military deployment for combat casualty care or field hospitals for public health emergencies. In the scenario of combat casualty care, when a wounded soldier is brought in, surgeons may benefit from immediate and actionable information on the state of the casualties so they can expeditiously stabilize the patient. This includes detection and visualization of the most common combat-related indications, such as foreign objects (e.g., bullets, shrapnel, metal components in body, etc.), bone fractures, bleeds, lacerations, ruptures, and traumatic brain injuries.

For practical reasons, it is desired for this to be performed with a device that is easy to transport and install and that works reliably and robustly in a rugged environment. Access to this capability closer to the point of injury may significantly reduce deaths from difficult-to-detect internal injuries. Earliest access to this data will help surgeons to take immediate and decisive action, increasing survival chances of wounded soldiers. It would therefore be desirable to provide a transportable, robust, and autonomous stationary CT imaging system that addresses the above issues.

Embodiments of the present disclosure will now be described, by way of example, with reference to the drawings, in which a highly mobile (e.g., portable), transportable, autonomous, stationary (e.g., a static, stationary or non-rotational gantry) CT imaging system or scanner without moving components provides CT imaging to environments that may be inaccessible to other CT imaging systems. The CT imaging system (which may be referred to herein as a scanner and/or portable stationary CT system) is able to provide imaging for forwardly deployed field hospitals, in some examples. The highly mobile, transportable, autonomous, stationary CT imaging system may provide faster assessment of casualties during conditions in which prompt patient care is desired, as in forward military deployment for combat care or field hospitals for public health emergencies.

According to at least one embodiment of the present disclosure, a stationary computed tomography (CT) imaging system (e.g., a static, stationary, non-rotational imaging system) may be separated into portable components (e.g., modules) and easily assembled in the field. The CT imaging system includes a plurality of x-ray sources and a plurality of x-ray detectors arranged around a portable patient support structure. The CT imaging system may be operated from a portable personal computer, such as a laptop, iPad, tablet, smart phone, etc. The portable personal computer may have system software and algorithms loaded thereon that may be used for operating the CT imaging system and/or processing data. In another example, the algorithms may be deployed on a cloud computing network and computations may be performed in the cloud computing network (e.g., while internet access is available when operating the CT imaging system). Advanced deep learning techniques may be used for image reconstruction (e.g., for sparse view and low power/low dose applications) and for image analysis, including detecting foreign objects, such as bullets, shrapnel, metal components in body, diagnosing injuries, and visualization. Visualization may be implemented through augmented reality and/or virtual reality media technologies. The CT imaging system design may be self-shielded to reduce and/or eliminate non-imaging radiation exposure even without a lead room. The CT imaging system may be battery powered such that it may operate without high-voltage power infrastructure.

Input electrical power and radiation shielding may be configured such that the stationary CT imaging system may operate without a lead room or a dedicated high-voltage power infrastructure as described above. An overall power reduction may realized from the elimination of the electric motor and driver that is typically provided for rotation of the x-ray source and detector gantry in a conventional CT imaging system. This overall reduction in power may result in a lower power requirement of the CT imaging systems of the present disclosure.

In an example, a transportable and autonomous stationary CT imaging system comprises a plurality of linear distributed x-ray sources interspersed with a plurality of digital flat-panel x-ray detectors. In one example, the stationary CT imaging system includes a plurality of alternating compact linear distributed x-ray sources and digital flat-panel x-ray detectors configured in a self-supporting structure (which may be referred to herein as a self-supporting stationary gantry) that includes alternating x-ray sources and x-ray detectors coupled to each other in an arrangement that completely surrounds a portable patient support structure through 360 degrees to form a self-supporting ring-shaped imager. Each x-ray source is positioned in-between and adjacent to two x-ray detectors, and each x-ray detector positioned in-between and adjacent to two x-ray sources. The stationary CT imaging system includes x-ray source and x-ray detector pairs. Each x-ray source is positioned opposite an x-ray detector. In another example, the self-supporting stationary gantry may comprise a half-ring of x-ray sources and a half-ring of x-ray detectors.

In the example stationary CT imaging system, three compact linear distributed x-ray sources and three digital flat-panel x-ray detector pairs are arranged in a hexagonal frame. More x-ray source and x-ray detector pairs may be used and the image reconstruction algorithm may be modified accordingly to accommodate a different number of x-ray source and x-ray detector pairs and the relative angles between the x-ray source and x-ray detector pairs.

The self-supporting stationary gantry may be coupled to a portable patient support structure (which may be referred to herein as a support surface). The portable patient support structure may include a patient support, such as a bed, gurney, stretcher, cradle, table, etc. to support a patent being imaged, two (or more) wheels coupled to a first end of portable patient support structure, and two (or more) collapsible legs coupled to a second end of the portable patent support structure. The two collapsible legs may extend down from the portable patent support structure to support the patent support off of the ground in a parallel arrangement to the ground. The patient support may include two (or more) handles extending from at least one end of the patient support to allow for easy transportability of the stationary CT imaging system. The at least two wheels may be coupled to an axle extending through a center of the wheels or alternatively, each wheel may be attached to a fork or frame member allowing the wheels to rotate when the stationary CT imaging system is moved or transported.

The self-supporting stationary gantry, including the plurality of x-ray sources and the plurality of x-ray detectors, and the portable patient support structure, including the patient support, two wheels, and two collapsible legs, are all individual, lightweight removable components that may be collapsible or removable and easily transportable. As the x-ray source and detector pairs are arranged around the patient support, operation of the stationary CT imaging system begins by energizing the x-ray sources in sequence or simultaneously. This provides the virtual rotation of an x-ray source to generate a sinogram of projection x-ray data. The sinogram may be reconstructed using conventional filtered back projection, accounting for the different x-ray output of the x-ray detectors, and x-ray detector sensitivity from a calibration scan. In this manner, no gantry rotation is used to generate a sinogram of projection x-ray data for each rotation angle. In an example, self-supporting stationary gantry may include a lead-shielded gantry and radiation shields covering the front and back of the gantry bore. In another embodiment, artificial intelligence based autonomous operation or one-button operation of the stationary CT imaging system may be provided.

In the example, the three x-ray sources (e.g., distributed x-ray source units) and three x-ray detectors (e.g., detector arrays) weigh approximately 50 kg each and are easily assembled into the self-supporting stationary gantry forming a ring-shaped imager. The self-supporting stationary gantry is mounted around the patient support structure. The location of the patient support relative to the self-supporting stationary gantry may be adjustable. In one example, an indicator member with marked gradations that may be read by a bar code reader may detect the speed that the patient support is advanced into the stationary gantry to cover the anatomical region to be scanned. This information may by input into the image reconstruction engine to enable whole body coverage.

In the example, each of the linear distributed x-ray sources (e.g., distributed x-ray source units) includes at least ten separate identical electron guns or electron emitters (e.g., cathodes) that may be powered at different voltage potentials to generate electrons and accelerate the electrons in the form of an electron beam toward at least ten separate identical stationary targets (e.g., anodes) at a ground potential to generate x-rays. Each linear distributed x-ray source is sealed in a vacuum enclosure and may have no moving components, no electric motors for target rotation, and no bearings. In some examples, no active pumping is performed. Instead, passive pumping via a getter component may be performed to ensure robustness, reduced weight, compactness, and simplicity for battlefield deployment. The getter component may ensure appropriate pressure in the vacuum enclosure. Each electron emitter includes electron emitter heating circuitry and electrostatic based beam optics optimization circuitry. In an example, a high voltage generator may be coupled to the plurality of linear distributed x-ray sources to provide heating power to the electron emitters, accelerate electrons in an electron beam to more than 100 kV, and provide bias voltages to control the x-ray focal spot size.

In the example, the electron emitters may be dispenser cathodes or cold-cathode electron emitters. In another example, smart electron beam focusing may be available via voltage bias to tailor the x-ray focal spot size for different applications as needed. A matrix type control may be used for electron emitter heating circuitry and electrostatic based beam optics optimization circuitry. In another example, one electron emitter may be powered at a time or multiple electron emitters may be powered at a time, as needed. In another example, high voltage arc protection may be provided for the electronics. In another example, ion back bombarding protection may be provided for the electron emitters. In another example, electron emitter life tracking may be provided. In another example, a potential topology of multiple targets for the same electron beam may be enabled via electrostatic beam deflection. In another embodiment, artificial intelligence based autonomous operation of the x-ray sources may be provided to optimize operation of the stationary CT imaging system on the fly.

The plurality of linear distributed x-ray sources may utilize a modular approach as a multi-source CT imaging system. In this example, the plurality of linear distributed x-ray sources may include an array of 32 separate electron guns, configured in a modular fashion with 32 x-ray focal spots within a vacuum chamber. Also, in this example, 32 separate stationary targets may be used, with no moving components, no bearings, and no electric motors. By rapidly switching between these 32 separate x-ray sources, multiple views may be acquired to replace the mechanical rotation of a CT scanner gantry. Individual emitter current control and focal spot control may be used to control each of the 32 separate electron guns. For example, compact and robust electronics may be used to adjust focusing parameters, emitted current per focal spot, duration of x-ray exposures. Innovative beam optics may be provided for increased image resolution tailored for different applications.

Tomographic image reconstruction techniques employed on the stationary CT imaging system may include model-based iterative reconstruction for low dose/low power applications, and wide-cone reconstruction for a large-area detector. This disclosure also contemplates the use of deep learning techniques for sparse view and low dose image reconstruction to produce diagnostic quality images from a reduced number of views. Deep learning based image reconstruction provides a computationally efficient way to produce high-quality images from sparse, low power data on a portable personal computer. A CT scan is automatically analyzed and annotated in terms of detection and visualization of the most common combat-related indications, such as foreign objects (e.g., bullets, shrapnel, metal components in body, etc.), bone fractures, bleeds, lacerations, ruptures, and traumatic brain injuries. Image analytics and annotated images may be visualized by a healthcare professional through overhead displays or through virtual reality technology.

This stationary CT imaging system may be used for military applications in some examples. As another example, this stationary CT imaging system may be useful in the case of pandemics where quick access to 3D imaging (in the form of low-end CT) is desired.

Figure 2:
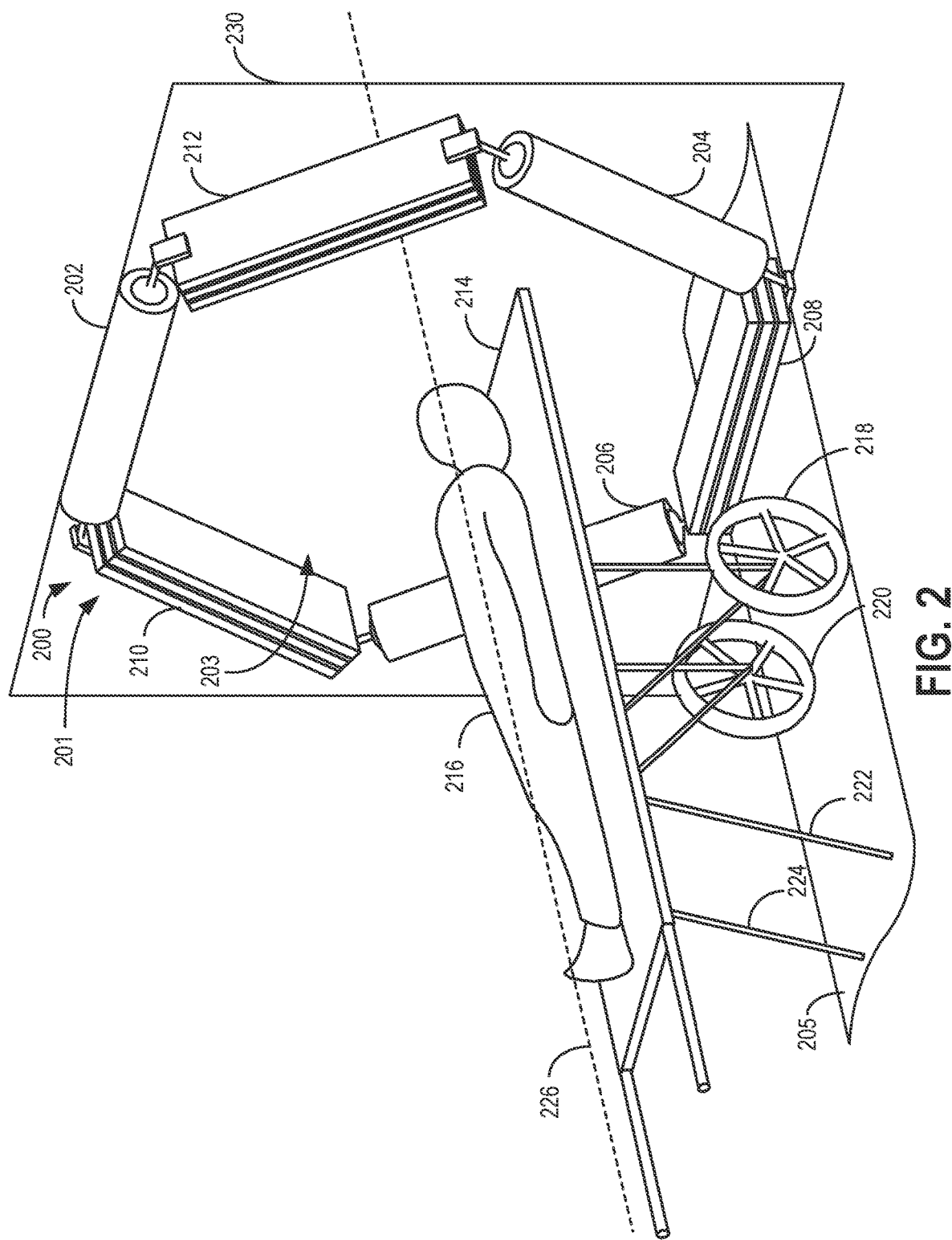
FIG. 2 shows a perspective view of a modular stationary imaging system, according to an embodiment.

Referring to FIG. 2, a perspective view of an imaging system 200 similar to, or the same as, the example described above is shown. Imaging system 200 may be referred to herein as a modular imaging system, stationary CT imaging system, and/or portable imaging system. Imaging system 200 is a non-limiting example of imaging system 100 and thus may include several components similar to those described above with reference to FIG. 1. For example, imaging system 200 includes a plurality of distributed x-ray source units (e.g., a first distributed x-ray source unit 202, a second distributed x-ray source unit 204, and a third distributed x-ray source unit 206), which may each be similar to the distributed x-ray source unit 104 described above with reference to FIG. 1. The distributed x-ray source units are releasably coupled to (e.g., fixedly coupled to, and able to be decoupled from) a plurality of detector arrays that are similar to the detector array 147 shown by FIG. 1 and described above. In the example shown in FIG. 2, the plurality of detector arrays includes a first detector array 208, a second detector array 210, and a third detector array 212. The plurality of distributed x-ray source units and the plurality of detector arrays form a self-supporting structure 201 including a central opening 203 shaped to receive a subject 216 to be imaged. The subject 216 may be positioned along a central axis 226 of the central opening 203 for imaging via the imaging system 200. For example, the subject 216 (e.g., a patient) may be supported by a support surface 214, and the subject 216 and the support surface 214 may each be moved along the central axis 226 into the central opening 203. The support surface 214 may be joined to legs (e.g., a leg 222, a leg 224, etc.), wheels (e.g., a wheel 218, a wheel 220, etc.), etc. configured to maintain the vertical position of the support surface 214 relative to the central opening 203. Stationary imaging (or imaging via a stationary imaging system) may refer to imaging of the subject without rotation of components of the imaging system 200 around the subject (e.g., without rotation of the distributed x-ray source units). In the example shown by FIGS. 2-3, the imaging system 200 is configured to perform stationary imaging and is additionally configured to be portable (e.g., via decoupling of the distributed x-ray source units and the detector arrays) such that the imaging system 200 may be more easily moved from one location to another.

Figure 3:
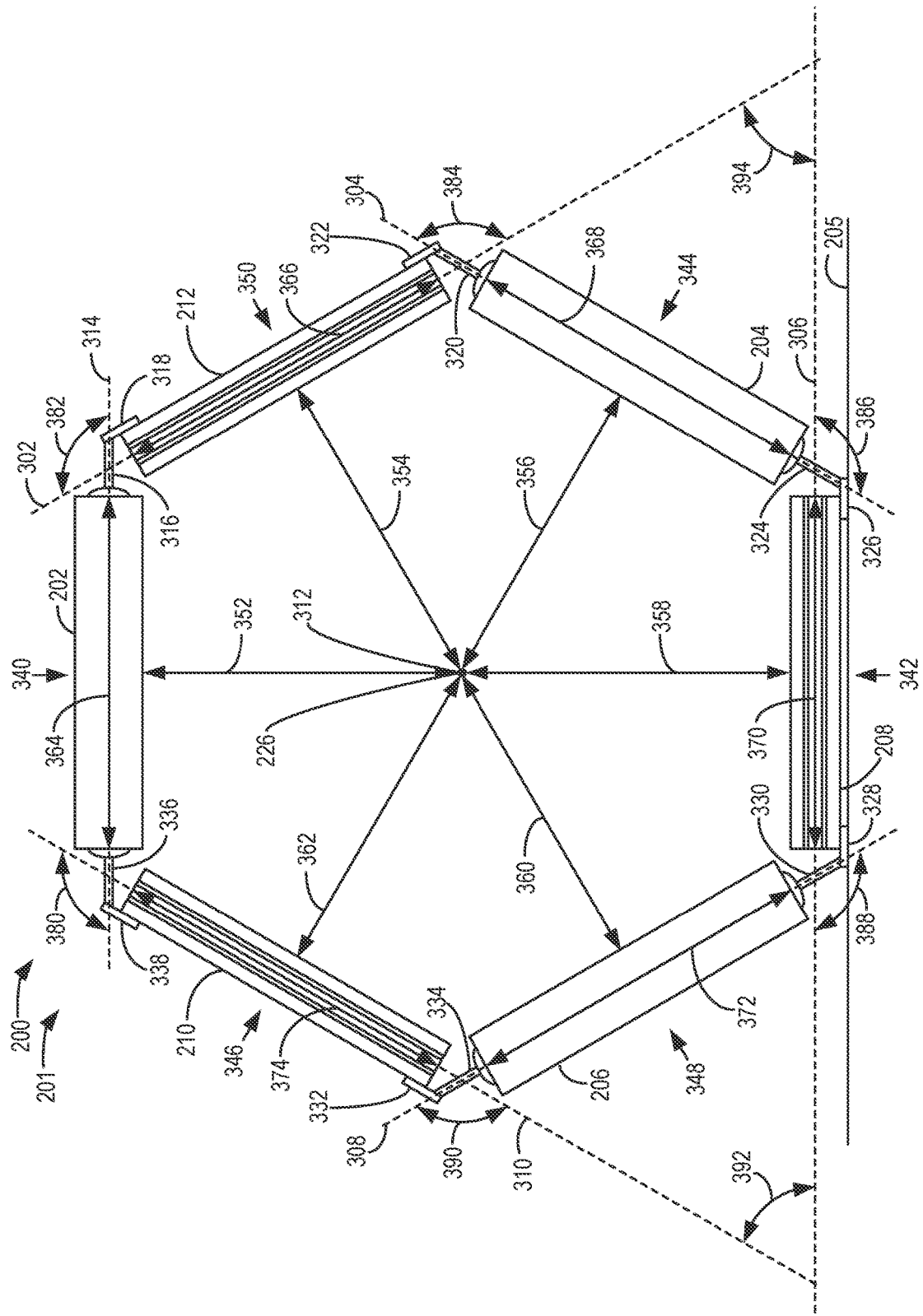
FIG. 3 shows a front view of the modular stationary imaging system of FIG. 2.

The self-supporting structure 201 may be referred to herein as a frame or imaging unit of the imaging system 200 (e.g., similar to the frame 102 and/or the imaging unit 123 described above with reference to FIG. 1). The self-supporting structure 201 is a rigid assembly resulting from the coupling of the plurality of distributed x-ray source units with the plurality of detector arrays. In some examples, the plurality of distributed x-ray source units may couple in interlocking engagement with the plurality of detector arrays to form the self-supporting structure 201. In other examples, fasteners such as brackets may releaseably couple the plurality of distributed x-ray source units with the plurality of detector arrays. The distributed x-ray source units and the detector arrays are coupled together such that the central axis 226 of the central opening 203 of the self-supporting structure 201 is arranged approximately parallel with a ground surface 205 on which the imaging system 200 sits. In some examples, a balance (e.g., weight distribution) of the self-supporting structure 201 may be configured such that the self-supporting structure 201 may be maintained in an upright position (e.g., with the central axis 226 arranged approximately parallel with the ground surface 205, as shown by FIGS. 2-3) without additional supports (e.g., without components other than the distributed x-ray source units, detector arrays, or brackets). For example, the first distributed x-ray source unit 202, the second distributed x-ray source unit 204, the third distributed x-ray source unit 206, the second detector array 210, and the third detector array 212 may each be supported by the first detector array 208 in the vertical direction relative to the ground surface 205 on which the imaging system 200 sits.

In other examples, the self-supporting structure 201 may include one or more rods or other components configured to maintain the self-supporting structure 201 in the upright position, with the relative position of the individual distributed x-ray source units and the detector arrays being maintained via the coupling between the distributed x-ray source units and the detector arrays (e.g., the interlocking engagement of the distributed x-ray source units with the detector arrays and/or the brackets coupling the distributed x-ray source units with the detector arrays).

Each distributed x-ray source unit may be interchangeable with each other distributed x-ray source unit of the plurality of distributed x-ray source units forming the self-supporting structure 201. For example, the imaging system 200 may include the first distributed x-ray source unit 202, the second distributed x-ray source unit 204, the third distributed x-ray source unit 206, the first detector array 208, the second detector array 210, and the third detector array 212, as shown by FIGS. 2-3. During assembly of the distributed x-ray source units with the detector arrays in order to form the self-supporting structure 201, the distributed x-ray source units may be interchanged with each other without affecting an imaging quality of the imaging system 200. For example, the first distributed x-ray source unit 202 and the second distributed x-ray source unit 204 may be interchanged (e.g., the first distributed x-ray source unit 202 may instead be arranged at the location of the second distributed x-ray source unit 204 shown by FIGS. 2-3, and the second distributed x-ray source unit 204 may instead be arranged at the location of the first distributed x-ray source unit 202 shown by FIGS. 2-3) without altering the imaging quality of the imaging system 200 (e.g., without increasing an imaging noise, x-ray radiation scattering, etc. of the imaging system 200). Similarly, the detectors arrays may be interchanged with each other without affecting the imaging quality. For example, the second detector array 210 may be interchanged with the third detector array 212 without altering the imaging quality (e.g., the second detector array 210 may instead be arranged at the location of the third detector array 212 shown by FIGS. 2-3, and the third detector array 212 may instead be arranged at the location of the second detector array 210 shown by FIGS. 2-3). During conditions in which the distributed x-ray source units and the detector arrays are coupled together to form the self-supporting structure 201 described above, the first distributed x-ray source unit 202, the second distributed x-ray source unit 204, the third distributed x-ray source unit 206, the first detector array 208, the second detector array 210, and the third detector array 212 are each vertically fixed (e.g., maintained in position in the vertical direction) within a same imaging plane 230 relative to the ground surface 205 on which the imaging system 200 sits.

The interchangeable characteristic of the distributed x-ray source units and the detector arrays may be increased in some examples by configuring each of the distributed x-ray source units to have a same shape (e.g., an equal sizing) and configuring each of the detector arrays to have a same shape. For example, the first distributed x-ray source unit 202 may have a length 364 along a centerline of the first distributed x-ray source unit 202, the second distributed x-ray source unit 204 may have a length 368 along a centerline of the second distributed x-ray source unit 204, and the third distributed x-ray source unit 206 may have a length 372 along a centerline of the third distributed x-ray source unit 206. The length 364, the length 368, and the length 372 may each be equal (e.g., a same amount of length). Similarly, the first detector array 208 may have a length 370 along a centerline of the first detector array 208, the second detector array 210 may have a length 374 along a centerline of the second detector array 210, and the third detector array 212 may have a length 366 along a centerline of the third detector array 212, with the length 370, the length 374, and the length 366 being equal (e.g., a same amount of length). In some examples, the length 364, the length 368, the length 372, the length 370, the length 374, and the length 366 may each be equal. By configuring the distributed x-ray source units and detector arrays to have the same size, an ease of assembling the distributed x-ray source units and detector arrays to form the self-supporting structure 201 may be increased. For example, a user may couple the detector arrays with the distributed x-ray source units in an alternating arrangement (e.g., with each distributed x-ray source unit coupled between two adjacent detector arrays) to assemble the self-supporting structure 201 without maintaining the exact sequential order of the distributed x-ray source units in the clockwise direction or counterclockwise direction between each assembly and disassembly operation. For example, in one assembled configuration, the first distributed x-ray source unit 202 may be arranged at the top of the imaging system 200, between the second detector array 210 and third detector array 212, as shown by FIGS. 2-3, while in another assembled configuration, the second distributed x-ray source unit 204 may instead be arranged at the top of the imaging system 200, between the second detector array 210 and third detector array 212, and the first distributed x-ray source unit 202 may instead be arranged vertically below the second detector array 210, between the third detector array 212 and the first detector array 208, without altering the imaging quality of the imaging system 200.

In the example shown by FIGS. 2-3, the self-supporting structure 201 formed by the coupling of the distributed x-ray source units with the detector arrays has a hexagonal profile. In particular, as shown by FIG. 3, the first distributed x-ray source unit 202 is arranged at a first side 340 of the hexagonal profile, the first detector array 208 is arranged at a second side of the hexagonal profile opposite to the first side 340 (e.g., across the central axis 266 relative to the first side 340), the second distributed x-ray source unit 204 is arranged at a third side 344 of the hexagonal profile, the second detector array 210 is arranged at a fourth side 346 of the hexagonal profile opposite to the third side 344 (e.g., across the central axis 266 relative to the third side 344), the third distributed x-ray source unit 206 is arranged at a fifth side 348 of the hexagonal profile, and the third detector array 212 is arranged at a sixth side 350 of the hexagonal profile opposite to the fifth side 348 (e.g., across the central axis 266 relative to the fifth side 348).

Each of the distributed x-ray source units and the detector arrays may be spaced approximately equally apart from the central axis 226. For example, as shown by FIG. 3, the first distributed x-ray source unit 202 is spaced apart from the central axis 226 by the length 352, the first detector array 208 is spaced apart from the central axis 226 by the length 358, the second distributed x-ray source unit 204 is spaced apart from the central axis 226 by the length 356, the second detector array 210 is spaced apart from the central axis 226 by length 362, the third distributed x-ray source unit 206 is spaced apart from the central axis 226 by the length 360, and the third detector array 212 is spaced apart from the central axis 226 by length 354. Each of the length 352, the length 354, the length 356, the length 358, the length 360, and the length 362 are arranged around the central axis 226 (e.g., the lengths extend radially from the central axis 226) and may be an equal amount of length (e.g., the length 352 may be a same amount of length as the length 358). Further, a first axis 314 extending along the centerline of the first distributed x-ray source unit 202 is parallel with a second axis 306 extending along the centerline of the first detector array 208, a third axis 304 extending along the centerline of the second distributed x-ray source unit 204 is parallel with a fourth axis 310 extending along the centerline of the second detector array 210, and a fifth axis 308 extending along the centerline of the third distributed x-ray source unit 206 is parallel with a sixth axis 302 extending along the centerline of the third detector array 212. The first axis 314 is arranged at a first angle 380 relative to the fourth axis 310 and a second angle 382 relative to the sixth axis 302, the third axis 304 is arranged at a third angle 384 relative to the sixth axis 302 and a fourth angle 386 relative to the second axis 306, and the fifth axis 308 is arranged at a fifth angle 388 relative to the second axis 306 and a sixth angle 390 relative to the fourth axis 310. In this configuration, the first detector array 208 couples to the second distributed x-ray source unit 204 at the fourth angle 386 and couples to the third distributed x-ray source unit 206 at the fifth angle 388, the second detector array 210 couples to first distributed x-ray source unit 202 at the first angle 380 and couples to the third distributed x-ray source unit 206 at the sixth angle 390, and the third detector array 212 couples to the first distributed x-ray source unit 202 at the second angle 382 and couples to the second distributed x-ray source unit 204 at the third angle 384. In some examples, the first angle 380, the second angle 382, the third angle 384, the fourth angle 386, the fifth angle 388, and the sixth angle 390 may be equal (e.g., the same amount of angle or number of degrees). The first detector array 208 is arranged at an angle 392 relative to the second detector array 210, and the first detector array 208 is arranged at an angle 394 relative to the third detector array 212. In some examples, the angle 392 and the angle 394 may be equal (e.g., the same amount of angle or number of degrees). In some examples, the angle 392 and the angle 394 may each be 60 degrees.

The distributed x-ray source units and the detector arrays are coupled together such that each of the distributed x-ray source units is arranged between two adjacent detector arrays. For example, the first distributed x-ray source unit 202 is arranged between the second detector array 210 and the third detector array 212, the second distributed x-ray source unit 204 is arranged between the third detector array 212 and the first detector array 208, and the third distributed x-ray source unit 206 is arranged between the first detector array 208 and the second detector array 210. In this configuration, the distributed x-ray source units alternate with the detector arrays in a clockwise or counterclockwise direction around the central axis 226. For example, in the clockwise direction, the first distributed x-ray source unit 202 couples to the third detector array 212, the third detector array 212 couples to the second distributed x-ray source unit 204, the second distributed x-ray source unit 204 couples to the first detector array 208, the first detector array 208 couples to the third distributed x-ray source unit 206, the third distributed x-ray source unit 206 couples to the second detector array 210, and the second detector array 210 couples to the first distributed x-ray source unit 202.

In some examples, the detector arrays and distributed x-ray source units may be configured to interlock directly with each other (e.g., features, such as teeth, projections, etc. formed on each distributed x-ray source unit may be configured to interlock with counterpart features, such as recesses, depressions, etc. formed on adjacent detector arrays). In other examples, such as the example shown by FIGS. 2-3, the distributed x-ray source units and the detector arrays may be configured to couple together via brackets. In particular, in the example shown, the first distributed x-ray source unit 202 couples to the third detector array 212 via a bracket 318 including an arm 316 and further couples to the second detector array 210 via a bracket 338 including an arm 336. The second distributed x-ray source unit 204 couples to the third detector array 212 via a bracket 322 including an arm 320 and further couples to the first detector array 208 via a bracket 326 including an arm 324. The third distributed x-ray source unit 206 couples to the first detector array 208 via a bracket 328 including an arm 330 and further couples to the second detector array 210 via a bracket 332 including an arm 334. In some examples, the brackets and/or arms may be formed integrally with the distributed x-ray source units and/or detector arrays. For example, the bracket 318 and the arm 316 may be formed together with the distributed x-ray source unit 202 as a single, unitary piece. In other examples, the brackets and/or arms may be separate components that are coupled to the distributed x-ray source units and/or detector arrays in order to fixedly couple the distributed x-ray source units with the detector arrays to form the self-supporting structure 201. The brackets may be configured to releaseably couple the distributed x-ray source units with the detector arrays such that the distributed x-ray source units and detector arrays remain coupled together for imaging of the subject 216 (shown by FIG. 2) and may be decoupled from each other for transporting the imaging system 200 from one location to another, for maintenance, etc. For example, the brackets may include one or more locking features (e.g., latches, etc.) configured to maintain the brackets in engagement with the distributed x-ray source units and detector arrays, and to unlock (e.g., decouple) the distributed x-ray source units from the detector arrays responsive to an unlocking of the locking features (e.g., actuation of a button, lever, etc. of the locking features of each bracket). By configuring the distributed x-ray source units and the detector arrays to decouple from each other when desired (e.g., via unlocking of the locking features of the brackets and/or disengagement of interlocking features of the distributed x-ray source units and detector arrays during disassembly of the imaging system 200 following an imaging of the subject 216), a portability of the imaging system 200 may be increased. The imaging system 200 may thus be assembled for imaging of subjects (e.g., the subject 216) in locations that may be difficult to accommodate larger imaging systems and/or less portable imaging systems.

Configuring the imaging system 200 to include an odd number of distributed x-ray source units (e.g., three) and an odd number of detector arrays (e.g., three) may increase an imaging quality of the imaging system 200 relative to configurations that include an even number of detector arrays and/or distributed x-ray source units. Further, by configuring the imaging system 200 to include exactly three distributed x-ray source units and exactly three detector arrays coupled together to form the self-supporting structure 201 with the hexagonal profile as described above may increase a stability, imaging quality, and/or ease of assembly of the imaging system 200. For example, the hexagonal profile provided by the configuration including exactly three distributed x-ray source units and exactly three detector units may increase a balance of the imaging system 200 and reduce a complexity of assembly of the imaging system 200. Further, the exactly three distributed x-ray source units and the exactly three detector units may provide for a complete scan of the subject 216 (e.g., 360 degrees of imaging of the subject 216) during conditions in which the subject 216 is imaged by the imaging system 200 and the image of the subject 216 is reconstructed according to the methods described herein.

In an example operation of the imaging system 200, the imaging system may image the subject 216 (e.g., acquire a scan of the subject 216) by energizing the first distributed x-ray source unit 202 to emit x-ray radiation in the vertical direction (e.g., toward the first detector array 208 arranged toward the ground surface 205), and the x-ray radiation emitted by the first distributed x-ray source unit 202 may be intercepted by the first detector array 208. Imaging the subject 216 may further include energizing the second distributed x-ray source unit 204 to emit x-ray radiation toward the second detector array 210 (e.g., in the direction of the length 356 and the length 362), and the x-ray radiation emitted by the second distributed x-ray source unit 204 may be intercepted by the second detector array 210. Imaging the subject 216 may further include energizing the third distributed x-ray source unit 206 to emit x-ray radiation toward the third detector array 212 (e.g., in the direction of length 360 and length 354), and the x-ray radiation emitted by the third distributed x-ray source unit 206 may be intercepted by the third detector array 212. Energizing the distributed x-ray source units may include providing electrical energy to the distributed x-ray source units via a portable energy source (e.g., a portable battery unit, similar to x-ray power source 145 described above with reference to FIG. 1). Throughout the imaging of the subject 216, the imaging system 200 is maintained in a stationary (e.g., non-moving) position. In particular, as the subject 216 is imaged, the distributed x-ray source units and the detector arrays are not moved (e.g., rotated, translated, etc.). In order to provide a full view of the subject 216 being imaged, the imaging system 200 may reconstruct the image of the subject 216 according to the methods described herein (e.g., via a deep learning network).

Figure 4:
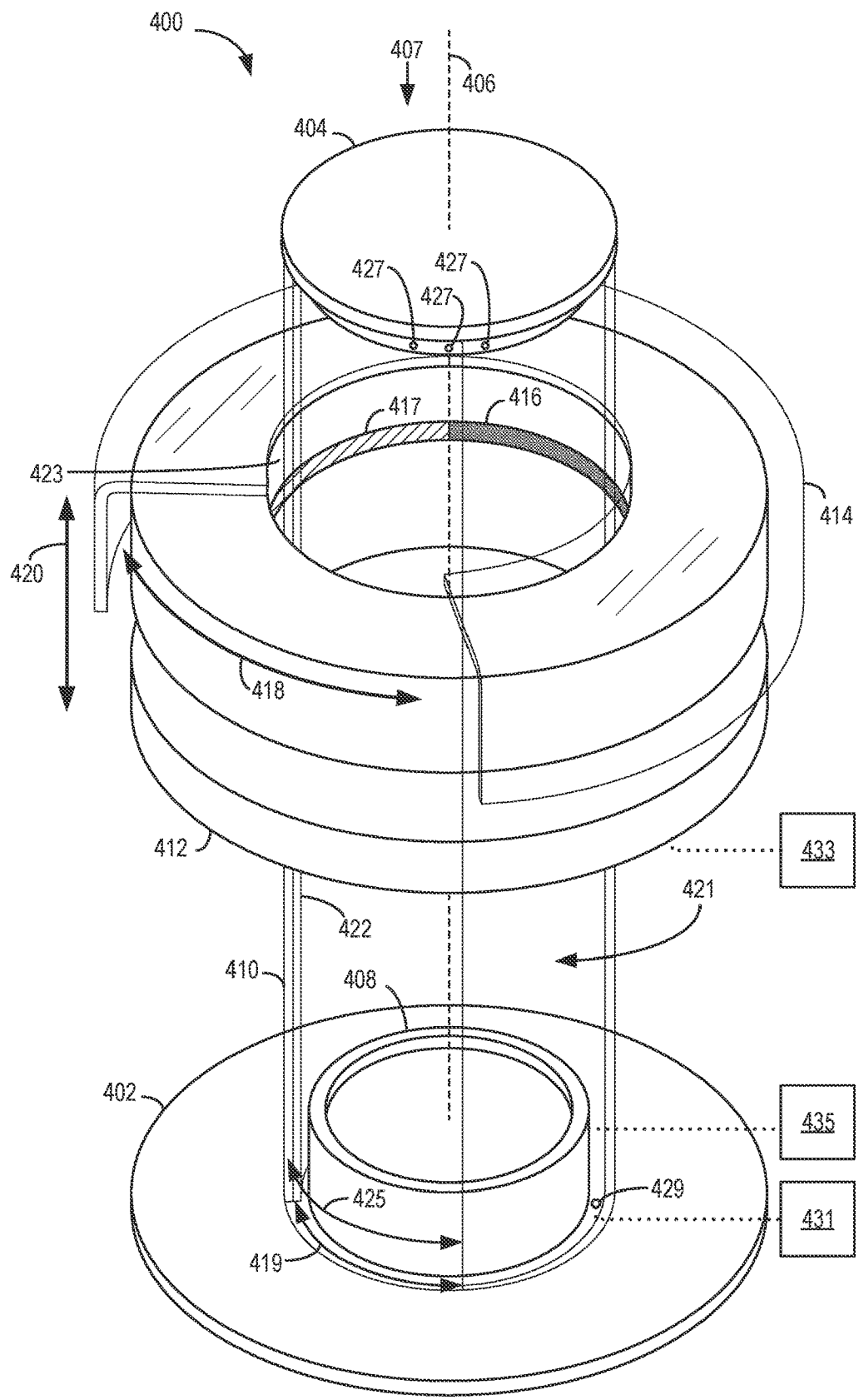
FIG. 4 shows a perspective view of an upright stationary imaging system, according to an embodiment.
Figure 5:
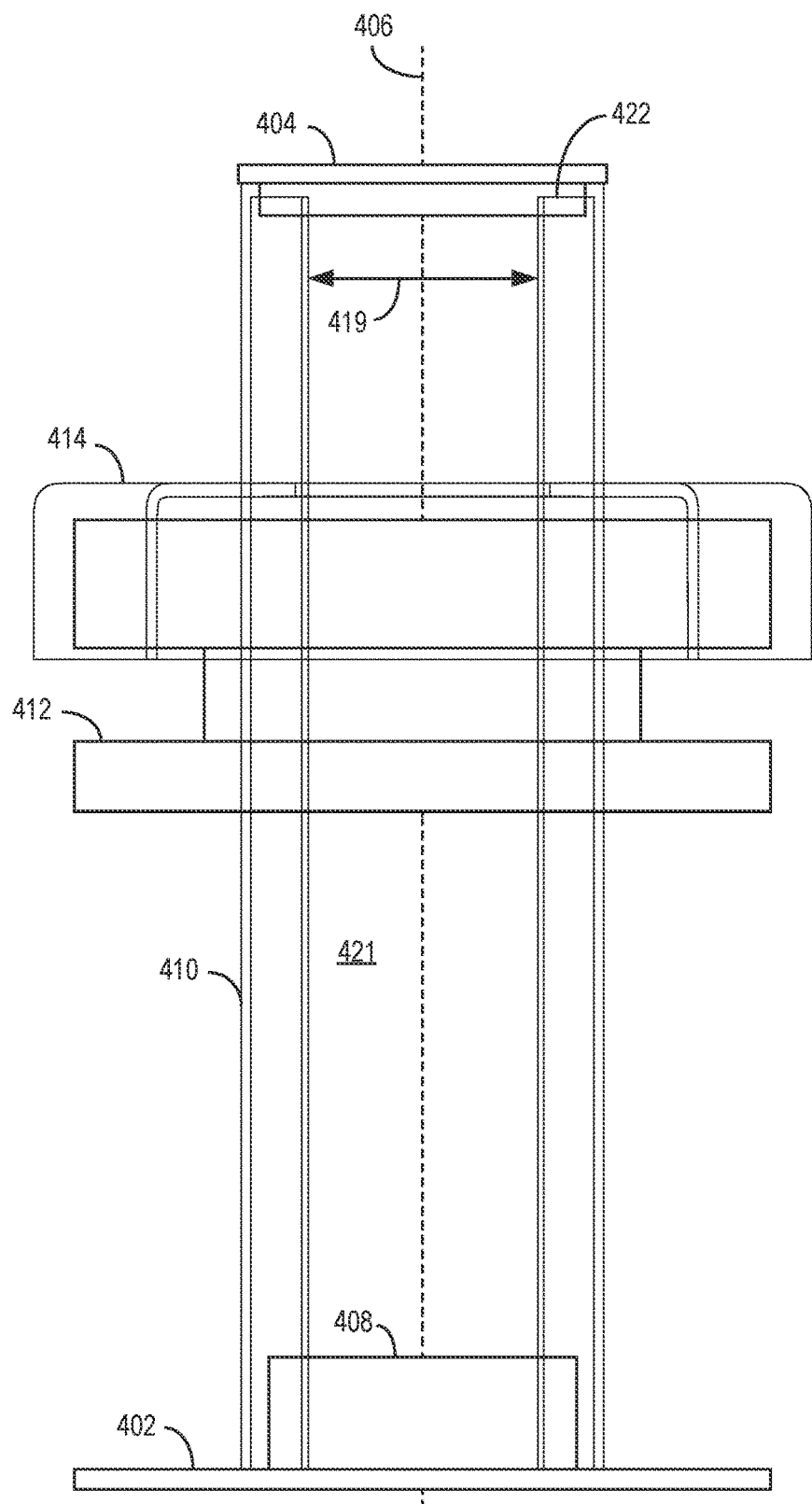
FIG. 5 shows a front view of the upright stationary imaging system of FIG. 4.

Referring to FIGS. 4-5, another imaging system 400 is shown. The imaging system 400 may be referred to herein as an upright imaging system, stationary CT system, and/or stationary CT scanner. The imaging system 400 may provide quick, automated, low-dose, low-cost chest CT scanning of a subject, in some examples. The imaging system 400 may include several components similar to those described above with reference to FIG. 1. For example, the imaging system 400 includes a distributed x-ray source unit 417. The distributed x-ray source unit 417 includes a plurality of x-ray emitters, similar to the emitters described above with reference to FIG. 1 (e.g., emitter 106, emitter 108, emitter 109, etc.). The imaging system 400 further includes a detector array 416. The detector array 416 includes a plurality of x-ray detectors, similar to the detectors described above with reference to FIG. 1 (e.g., detector 103, detector 105, detector 107, etc.). Because the multiple emitters of the distributed x-ray source unit 417 may emit x-ray radiation (e.g., x-ray beams) spanning an angular range around a central axis 406 of the imaging system 400, the imaging system 400 may image a subject (e.g., the subject 216 shown by FIG. 2) without rotation of the distributed x-ray source unit 417 and the detector array 416 around the central axis 406. For example, the emitters of the distributed x-ray source unit 417 may be arranged over an angular range of 360 degrees surrounding the subject. As another example, the emitters may be arranged over an angular range of 180 degrees surrounding the subject. Similarly, the detectors of the detector array 416 may extend over an angular range of 360 degrees, 180 degrees, etc. around the subject. The imaging system 400 may utilize the image reconstruction approaches described herein in order to provide a full image of the subject with sparse-view datasets and/or limited view angle datasets.

In some examples, the imaging system 400 may be configured as a semi-stationary imaging system in which the detector array 416 is rotatable around the subject but the distributed x-ray source unit 417 is maintained in a fixed position around the subject (e.g., the distributed x-ray source unit 417 is not rotated around the subject). The imaging system 400 may be configured such that the distributed x-ray source unit 417 and the detector array 416 may be translated vertically (e.g., moved up and down a vertical length of the imaging system 400) during imaging of the subject (e.g., in order to scan various portions of the chest of the subject, to perform a helical scan, etc.). In some examples, the imaging system 400 may translate the subject vertically relative to the distributed x-ray source unit 417 and the detector array 416 during imaging of the subject.

Because the imaging system 400 does not include a rotating gantry, a cost of the imaging system 400 may be reduced relative to conventional imaging systems that include a gantry configured to rotate around the subject to be imaged. Further, because the subject is imaged by the imaging system 400 while in an upright position, a size of the imaging system 400 may be reduced relative to imaging systems that are configured to image the subject in a prone position. Because the subject is maintained in the upright position during imaging, a flattening of the subject as a result of gravity may be reduced, which may enable the scan field of view, chamber size, and radiation dosage of the imaging system 400 to be reduced. As one example, the scan field of view may be reduced to a 30 centimeter diameter, compared to a 50 centimeter diameter often used by conventional imaging systems. If truncation of the imaging of the subject occurs, a truncation correction may be used according to the methods described herein. For example, a deep learning algorithm (e.g., a generative adversarial network) may be trained to estimate the truncated data. Training data for the deep-learning algorithm may be obtained by utilizing untruncated CT datasets as the label and truncated CT datasets as the input. In some examples, iterative reconstruction may be used. In some examples the view sampling of the subject may be non-uniform. For example, the view sampling may be locally dense, but sparse overall (e.g., with 4 detectors followed by a gap, in a repeating pattern arrangement). The spacing of the emitters within the distributed x-ray source unit 417 and/or the spacing of the detectors within the detector array 416 may be selected to increase a view sampling. For example, opposite views may be interlaced to reduce a redundancy in conjugate rays. In some examples, an odd number of x-ray emitters may be arranged uniformly within the distributed x-ray source unit to provide 360 degrees of imaging of the subject. As one example, the x-ray emitters may be arranged at positions corresponding to 0° and 8° relative to a given origin (e.g., an opening 419 of the imaging system 400 shaped to receive the subject to be imaged) and on the opposite side a focal spot may be positioned at −4°+180°, 4°+180°, and 12°+180°. As another example, segments of the x-ray emitters may be tilted to be parallel with the central axis 406 or to be at another angle to the central axis 406 (e.g., in an oblique arrangement. In some examples, a position of an electron beam directed toward the anode of each x-ray emitter (e.g., from a corresponding cathode of the emitter) may be adjusted to sweep along the anode.

In some examples, the available view range provided by the arrangement of the emitters within the distributed x-ray source unit and the detectors within the detector array may be less than 180 degrees plus the fan angle. For example, the view range may be angular range of the x-ray radiation emitted by the distributed x-ray source unit may be 160 degrees while the angular range at which the detector array may intercept x-ray radiation may be 200 degrees. In such examples, deep learning may be used according to the methods described herein to extrapolate additional views in the view angle direction. If the final reconstructed image volumes have better spatial resolution in one direction (e.g. in coronal planes) compared to another direction (e.g. in the sagittal planes), the data sets may be primarily shown as coronal images.

It is often desirable to perform a scan of the subject quickly in order to reduce a likelihood of artifacts resulting from motion of the subject (e.g., respiratory and/or cardiac motion). However, in configurations that have a lower amount of electrical power available at the emitters, scan time may be increased. In order to reduce artifacts resulting from the motion of the subject while performing longer scans, time-sequential sampling may be utilized according to the methods described herein.

The imaging system 400 includes a chamber 421 shaped to enclose the subject to be imaged. The subject may be supported in the upright position within the chamber 421 via support surface 408 (which may be referred to herein as a subject support surface). The support surface 408 may be a pedestal, as one example. In some examples, the support surface 408 may be motorized (e.g., coupled to a motor 433 controlled by a support surface motor controller, such as the support surface motor controller 126 shown by FIG. 1 and described above) such that the support surface 408 may move in the vertical direction (e.g., a vertical direction 420, parallel with central axis 406) in order to adjust the vertical position of the subject within the chamber 421.

The imaging system 400 further includes an annular imaging unit 412. The annular imaging unit 412 includes the distributed x-ray source unit 417 and the detector array 416 disposed therein, with the distributed x-ray source unit 417 and detector array 416 arranged at an inner perimeter 423 of the annular imaging unit 412. The distributed x-ray source unit 417 may be arranged opposite to the detector array 416 across the central axis 406. The annular imaging unit 412 surrounds the chamber 421 such that the inner perimeter 423 of the annular imaging unit 412 is arranged adjacent to the chamber 421. The annular imaging unit 412 may be driven by a motor to translate in the vertical direction (e.g., the direction of central axis 406) in a fixed angular orientation relative to the chamber 421 and inner enclosure 422. In particular, the annular imaging unit 412 may be configured to move in the direction parallel with the central axis 406 without rotating around the central axis 406 (e.g., without adjusting the angular position of the annular imaging unit 412 in direction 418 around the central axis 406). In some examples, the annular imaging unit 412 may include a shroud 414 partially enclosing the annular imaging unit 412.

The imaging system 400 includes an outer enclosure 410 and the inner enclosure 422. In some examples, one or both of the outer enclosure 410 and inner enclosure 422 may be formed of a material transparent and/or translucent to visible light (e.g., glass, polycarbonate, etc. transparent to light having a wavelength within a range of 400 to 750 nanometers) such that during conditions in which the subject is positioned within the chamber 421 for imaging, the subject may be visible within the chamber 421 from an exterior of the chamber 421. The outer enclosure 410, inner enclosure 422, and support surface 408 may each be supported by a base 402 of the imaging system 400 (e.g., supported in direct contact with the base 402). The inner enclosure 422 may be fixedly coupled to the base 402 such that the inner enclosure 422 does not rotate relative to the base 402. However, the outer enclosure 410 may be rotatably coupled to the base 402 such that the outer enclosure 410 may rotate relative to the base 402 and the inner enclosure 422. The inner enclosure 422 includes opening 419 and the outer enclosure includes an opening 425. During conditions in which the opening 419 and the opening 425 are aligned (e.g., arranged at a same rotational position around the central axis 406, the subject to be imaged may pass through the opening 419 and the opening 425 to enter the chamber 421. The outer enclosure 410 may then be rotated relative to the inner enclosure 422 in order to seal the opening 419 of the inner enclosure 422 via the inner surfaces of the outer enclosure 410. A length of the opening 419 around the central axis 406 (e.g., an arcuate length of the opening 419) may be less than or equal to a length of the opening 425 around the central axis 406 (e.g., an arcuate length of the opening 425).

The inner enclosure 422 and the outer enclosure 410 are each sealed at an end 407 of the imaging system 400 (e.g., a top end) opposite to the base 402 by a cap 404. The cap 404 may include a plurality of illumination elements 427 configured to emit ultraviolet radiation through the chamber 421 and in a direction of the support surface 408. For example, following imaging of the subject, the subject may be removed from the chamber 421 and the chamber 421 may be disinfected via the ultraviolet radiation emitted by the illumination elements 427. In some examples, the base 402 may include a plurality of openings, such as opening 429, which may fluidly couple the chamber 421 to a disinfectant source 431 (indicated schematically in FIG. 4). In some examples, the disinfectant source 431 may be a reservoir containing a disinfectant vapor (e.g., hydrogen peroxide), and the disinfectant vapor may flow into the chamber 421 for cleaning of the chamber 421 following imaging of the subject. In order to reduce a likelihood of spraying the disinfectant vapor outside of the chamber 421, the outer enclosure 410 may be rotated to seal the opening 419 during conditions in which a cleaning operation is commanded (e.g., conditions in which the disinfectant vapor is supplied to the chamber 421 via opening 429 and/or ultraviolet radiation is emitted via illumination elements 427).

In an example operation of the imaging system 400, a scan of the subject may be acquired while the subject is supported in the upright position within the chamber 421 by energizing the distributed x-ray source unit 417 to emit x-ray radiation through the subject and across the chamber 421, with the x-ray radiation being received at the detector array 416. While the subject is being imaged (e.g., scanned), the angular position of the distributed x-ray source unit 417 is maintained relative to the chamber 421 throughout an entire duration of the imaging (e.g., the distributed x-ray source unit 417 is not rotated around the subject). In particular, the angular position of the imaging unit 412 is maintained throughout the duration of the scan. However, the imaging unit 412 may be driven in the vertical direction 420 via the motor 433 (shown schematically by FIG. 4) during imaging of the subject in order to image a larger portion of the subject and/or to perform a helical scan. The motor 433 may be controlled by a motor controller, similar to the motor controller 112 shown by FIG. 1 and described above. Because the distributed x-ray source unit 417 and the detector array 416 are each disposed within the imaging unit 412, driving the imaging unit 412 in the vertical direction 420 moves the distributed x-ray source unit 417 and the detector array 416 in unison in the vertical direction 420. In some examples, the subject may be moved in the vertical direction 420 within the chamber 421 during imaging of the subject by driving the support surface 435 in the vertical direction 420 via the motor 433 (indicated schematically in FIG. 4).

Figure 7:
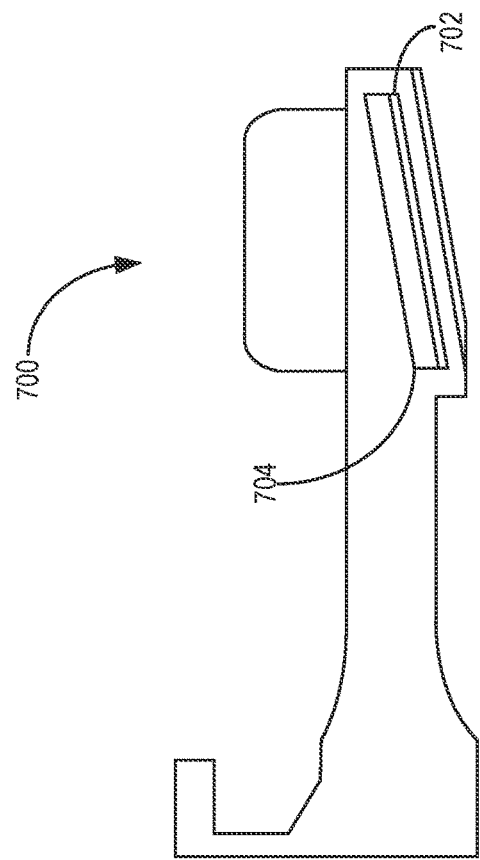
FIG. 7 shows a side view of another target of an x-ray emitter, according to an embodiment.
Figure 6:
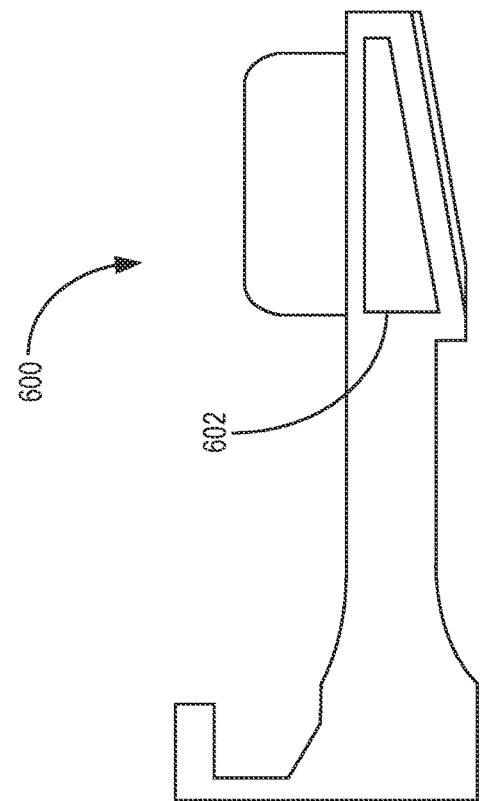
FIG. 6 shows a side view of a target of an x-ray emitter, according to an embodiment.

Referring to FIGS. 6-7, different targets (e.g., anodes) of an x-ray emitter are shown. In particular, FIG. 6 shows a side view of target 600, and FIG. 7 shows a side view of target 700. The target 600 and/or the target 700 may be included in the imaging systems described herein (e.g., the targets shown by FIGS. 6-7 may be included distributed x-ray source unit 104 shown by FIG. 1 and described above, distributed x-ray source unit 202 shown by FIG. 2 and described above, etc.). For example, anode 111, anode 115, anode 121, etc. shown by FIG. 1 and described above may be similar to, or the same as, target 600 and/or target 700. Conventional x-ray targets are often rotating targets (e.g., discs comprising molybdenum with a track of tungsten) or stationary targets (e.g., blocks of copper with tungsten brazed thereto). However, the targets contemplated herein may include diamond layers and/or phase-change materials (PCMs). As one example, layers of diamond may be included proximate to a tungsten layer at which electrons emitted by cathode (e.g., cathode 113, cathode 117, etc. shown by FIG. 1 and described above). As another example, PCMs may be included within an interior of the targets. The diamond layers and/or PCMs may decrease a rate at which the temperature of the targets increases while in operation (e.g., while electrons are intercepted by the targets).

In the example shown by FIG. 6, the target 600 includes a region 602 of PCM disposed within an interior of the target 600. The region 602 may reduce a rate at which the temperature of the target 600 increases by controlling a bulk temperature of the target 600. The region 602 of PCM may absorb a portion of heat provided to the target 600, where the heat is utilized to change the phase of the PCM (e.g., from solid to liquid, or vice versa) rather than to increase the temperature of the target 600. The trapezoidal shape of the region 602 of PCM may increase a depth or thickness of the region 602 within the target 600, which may further increase the heat absorption characteristic of the region 602 of PCM.

In the example shown by FIG. 7, the target 700 includes a diamond layer 702 in addition to a region 704 of PCM. The diamond layer 702 and region 704 of PCM may together further reduce a rate at which the temperature of the target 700 increases. In particular, the diamond layer 702 may reduce temperature increases of the target 700 at portions of the target 700 proximate to an area at which electrons are intercepted by the target 700. Further, the diamond layer 702 may increase a transfer of heat to the region 704 of PCM, which may reduce a heating of other portions of the target 700. In some examples, the diamond layer 702 and region 704 of PCM may reduce a typical operating temperature of the target 700 by 100-250 degrees Celsius.

The target 600 and/or the target 700 may include an alloy of copper, aluminum, and silicon, in some examples. The copper, aluminum, and silicon may have a higher specific heat capacity in both single (2.5×) and two-phase zones (1.1×) compared to an alloy of Copper, Zinc, and Phosphorus. Trapezoidal PCM regions and the copper, aluminum, and silicon alloy may reduce a rate of temperature increase for small targets in particular, while diamond layers may reduce the rate of temperature increase for large targets in particular. In some examples, the diamond layer may be 0.5 mm thick.

Each of the target 600 shown by FIG. 6 and the target 700 shown by FIG. 7 may include tracks formed from several materials. For example, target 600 may include a track formed from tungsten and another track formed from molybdenum to generate different energy spectrum from each track. Electron beams emitted by the respective cathode may be deflected back and forth between the tracks. In some examples, the cathode may emit two individual electron beams, with one beam directed toward the tungsten track and with one beam directed toward the molybdenum track. In some examples, each track may be formed of a same material, and the two electron beams may be deflected between the two tracks to reduce a likelihood of degradation of the target.

Figure 8:
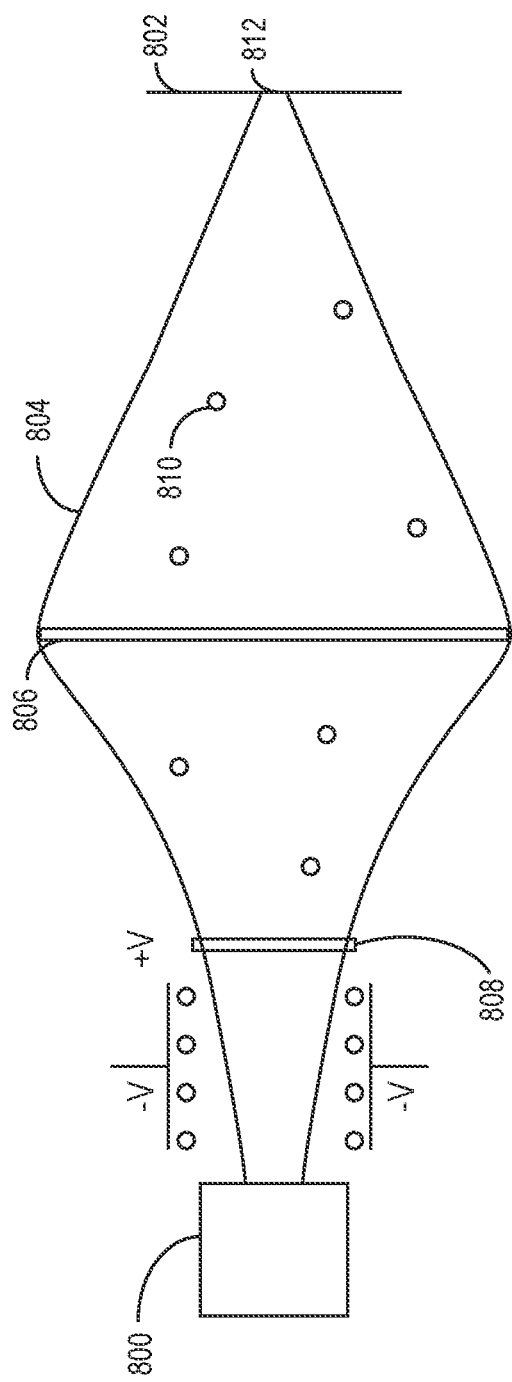
FIG. 8 shows schematically shows an electron beam, according to an embodiment.
Figure 9:
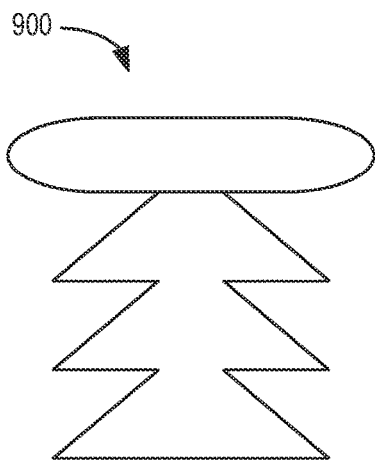
FIG. 9 shows an insulator for an x-ray emitter, according to an embodiment.
Figure 10:
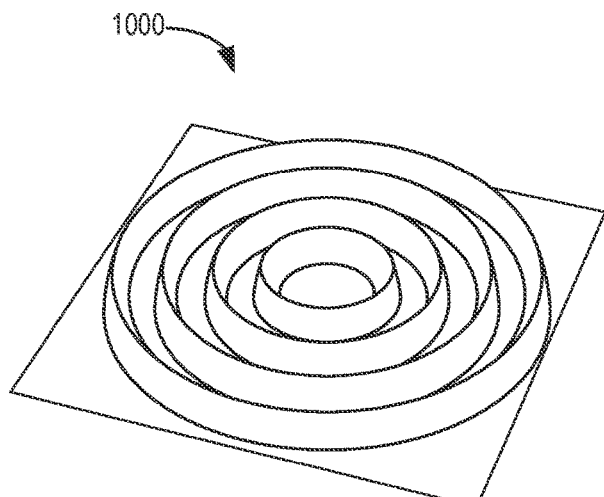
FIG. 10 shows another insulator for an x-ray emitter, according to an embodiment.
Figure 11:
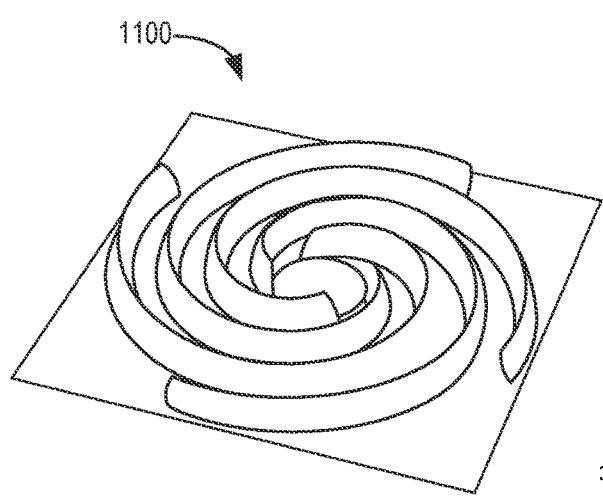
FIG. 11 shows another insulator for an x-ray emitter, according to an embodiment.
Figure 12:
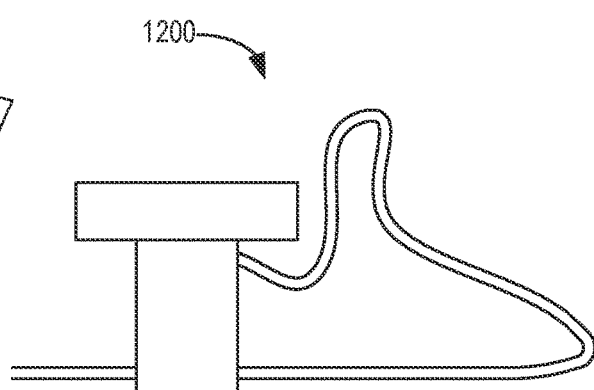
FIG. 12 shows another insulator for an x-ray emitter, according to an embodiment.

Referring to FIG. 8, an electron source 800, a target 802, an electron beam 804, a magnetic lens 806, a PIE electrode 808, a plurality of ions 810, and a small beam spot 812 are schematically shown. The electron source 800 may be a cathode similar to the anodes described above with reference to FIG. 1, and the target 802 may be an anode similar to the anodes described above with reference to FIG. 1.

In x-ray source units, it may be desirable to reduce a likelihood of spit and/or emitter degradation. Emitters can be affected by backstreaming ions and by high voltage spits. The voltage between the gate electrode and the field emitters may be constrained. To clamp the voltage, an integrated thyristor structure may be utilized. The thyristor structure may breakdown during conditions in which the voltage exceeds a threshold voltage. The structure may be integrated to control current paths and to route the spit current in desired areas away from the field emitters.

Further, the temperature increase may be constrained during spits. Heat may be produced by current flowing through electrically resistive material, with the heat dissipating through thermal conduction and irradiation. A thick gate electrode may be provided, where the electrode is coated with a high thermal conductivity material such as diamond. Areas of increased resistivity may be provided where it is desirable to dissipate the energy into heat. The areas of increased resistivity may be inside or outside of a vacuum structure. Emitters may have a reduced likelihood of degradation through utilization of an increased vacuum and/or active getters that are heated. The getters may be heated when pressure increased, and the ion collector and number of arcs may be monitored.

A back-scatter electron collector may be included. The back-scattered electron collector may collect backscatter electrons and decrease the target temperature during operation. The back-scattered electron collector may absorb a portion of the heat during a spit through radiation, and may be coated with high emissivity coating. Various other components may be coated with coatings having low secondary electron emission.

A likelihood of field emitter degradation may be decreased via active getters. If a sealed vacuum chamber is desired, active getters may increase performance.

Assembling the targets at specific angles and adding a shroud around the targets may be effective against ions. Ion traps toward the electron gun may additionally reduce a likelihood of degradation. An ion trap or barrier may be biased at one positive voltage to repel ions. Other ion control systems may include several electrodes, similar to the example shown.

Electrons emitted by a cold cathode may be utilized as a source of primary electrons that hit another plate to create secondary electron emission. Such a configuration may be a booster and may provide a reduced likelihood of degradation versus ions and arcs. The above configurations may be applied to distributed x-ray sources, such as the distributed x-ray source unit 104 shown by FIG. 1 and described above.

Referring to FIGS. 9-12, various different high voltage insulator configurations are shown. The high voltage insulators may be included within the distributed x-ray source units described herein (e.g., distributed x-ray source unit 104 shown by FIG. 1 and described above). One of the drivers for x-ray source size is the size of the high voltage insulators. Conventional insulators are often cylindrical or pancake-shaped. It may be desirable to reduce a size of the insulators for increased performance. In some examples, non-linear resistive materials may be applied as coatings to the resistors. Such coatings may include silicon carbide or titanium nitride. The coatings may reduce the field concentration and smooth out the field to reduce surface flashover and the insulator dimensions.

In some examples, machinable aluminum nitride may be used instead of alumina to provide zig-zag shaped surface to increase the surface tracking length and reduce the radial dimensions. For example, aluminum nitride may be machined to form the insulator 900 shown by FIG. 9, the insulator 1000 shown by FIG. 10, and/or the insulator 1100 shown by FIG. 11. A stress grading coating or low secondary emission coating may be applied to reduce the triple conjunction field, and the length of an insulator may be reduced by about 50% relative to conventional examples.

The triple point junction effect may be shielded by the geometric design of the electrode, with the electrode folding over the triple junction point to act as a Faraday cage. If the electrical stress is too large at the area where it is facing to the end of the electrode, a nonlinear resistive coating can be applied to lower the field further. For example, the inner ring diameter of the ceramic could be smaller, or the height could be taller to reduce the outer diameter of the ceramic disc (e.g., similar to the electrode 1200 shown by FIG. 12). The higher wall may be shaped maintain the angle at the bottom portion the same to avoid a stress concentration at the bottom portion. However, stress grading may be applied to the bottom portion as well.

In some systems, tiled emitters may be included to provide emission from specific zones to provide small or large spots and wobble. Multiple x-ray sources may be connected to a same high voltage generator. For example, one end of a connection may connect to the generator, and another end may be split to connect to multiple different x-ray sources. As another example, every odd x-ray source may be coupled to a first generator and every even x-ray source may be coupled to a second generator to provide a dual kVp. The two generators may be operated at the same voltage for arc and spit management. Further, electronics may be included in vacuum tubes to disconnect the tubes responsive to over shoot, arcs, or spit.

Figures 13, 14:
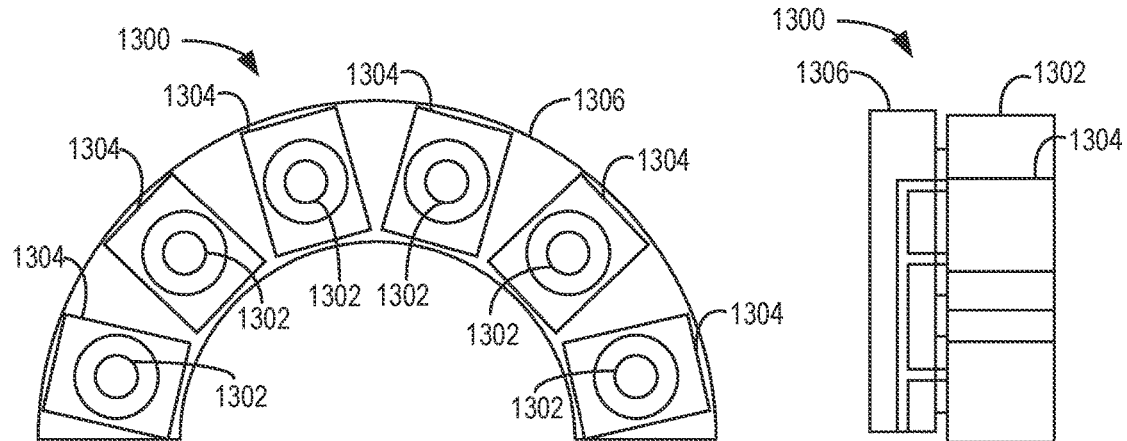
FIG. 13 shows schematically shows an interface for a high voltage generator and x-ray tubes.
FIG. 14 shows schematically shows another view of the interface of FIG. 13.

Referring to FIGS. 13-14, schematic diagrams representing connections between a high voltage generator and x-ray tubes are shown. In particular, FIG. 13 schematically shows a front view of an interface for a high voltage generator and x-ray tubes, and FIG. 14 schematically shows a side view of the interface.

In x-ray imaging systems, the high-voltage (HV) generator and the x-ray tube are often connected using a flexible HV cable. Such HV cables are point-to-point connections, e.g. between a HV generator and an x-ray tube. For some applications, the cables are flexible to account for relative movement of the interconnected devices with respect to each other. For other applications, such as different components mounted on a CT imaging system, such relative movement may not be utilized, but commonly, flexible HV cables are used, nonetheless. However, even in the case where only small distances are bridged, the cable often includes a longer length to be flexible enough to be unplugged. This is inefficient for systems with many HV devices, such as a multi-spot system using multiple x-ray tubes. Thus, FIGS. 13 and 14 schematically show a rigid support system 1300 that provides for both the mounting of the components and the distribution of the HV without cables. The rigid support system 1300 includes a plurality of connections 1302 configured to electronically couple individual x-ray tubes 1304 to a rigid support structure 1306.

Figures 15, 16:
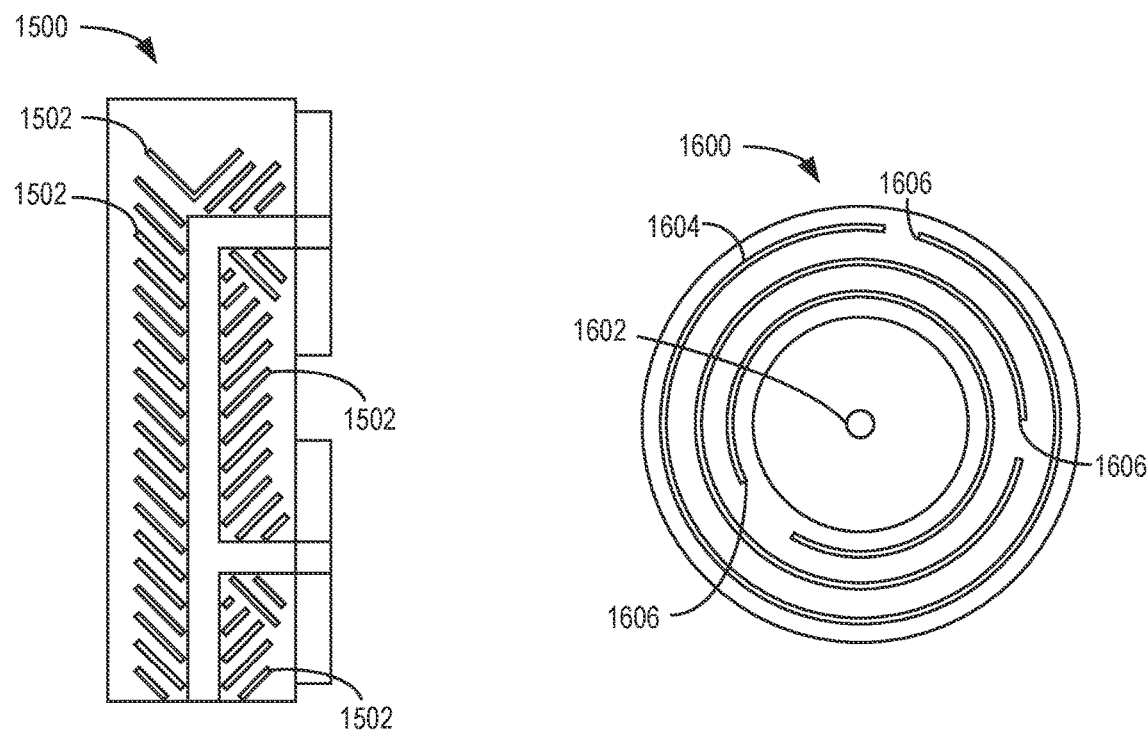
FIG. 15 shows a side view of a segment of a high voltage distribution system, according to an embodiment.
FIG. 16 schematically shows a flat connector for a high voltage distribution system, according to an embodiment.

Referring to FIG. 15, a side view of a segment of a high voltage distribution system (HVDS) 1500 is shown. The HVDS may be integrated into a rigid support structure, such as the rigid support structure 1306 shown by FIGS. 13-14. The HVDS may provide for mounting of components and distribution of the high voltage within the same support structure. In this configuration, high voltage may be supplied to the components without the use of cables (e.g., connecting cables). The HVDS may be disposed within a sealed container filled with an electrical and thermal insulating medium (e.g., oil). Because the HVDS may not include active electronics, a reliability of the HVDS may be increased. In some examples, additional insulation may be included in conjunction with the oil, such as plastic components formed from polypropylene (PP). FIG. 15 shows the insulating plastic components 1502 arranged within the HVDS. In some examples, the plastic components 1502 may have a different shape. For example, in the example shown by FIG. 15, the plastic components 1502 are shaped as cones that increase a creepage distance through the oil. However, in other examples, the plastic components 1502 may be shaped to wind around the conductor in a screw-like fashion (e.g., similar to a shape of overlapping insulating tape applied to outer surfaces of a conductor).

Referring to FIG. 16, a schematic of a flat connector 1600 for a high voltage distribution system is shown. In one example, the flat connector 1600 may be used with the HVDS described above with reference to FIG. 15. To insulate high-voltage connectors, the high-voltage connectors are often spaced apart from the live wire and the grounding. In some examples, the insulation may be achieved by shaping the connector as a long rod or with a 'candlestick' shape, or by using a flat connector where the insulation is provided on a flat surface. When many components are arranged close to each other, the 'candlestick' shape may provide a tighter spacing. However, connectors shaped as a rod or 'candlestick,' have an increased depth relative to flat connectors, which may complicate packaging conditions.

High-voltage connectors often include oil or grease to reduce an amount of air surrounding the high-voltage connectors, which may increase creepage distance. Such connectors utilizing oil may include a well arranged in a horizontal position to the connector to contain the oil. If a well is not desired, grease may be utilized. However, to simplify assembly and/or production, a connector including neither grease nor oil is contemplated, such as the flat connector 1600 shown by FIG. 16. The flat connector 1600 includes a high-voltage connection 1602 arranged at a center of the flat connector 1600 and a plurality of insulating barriers 1604 arranged circumferentially around the high-voltage connection 1602. Gaps 1606 between the insulating barriers may permit air to flow out from the flat connector 1600 during conditions in which a connection is made to the flat connector 1600.

Figure 17:
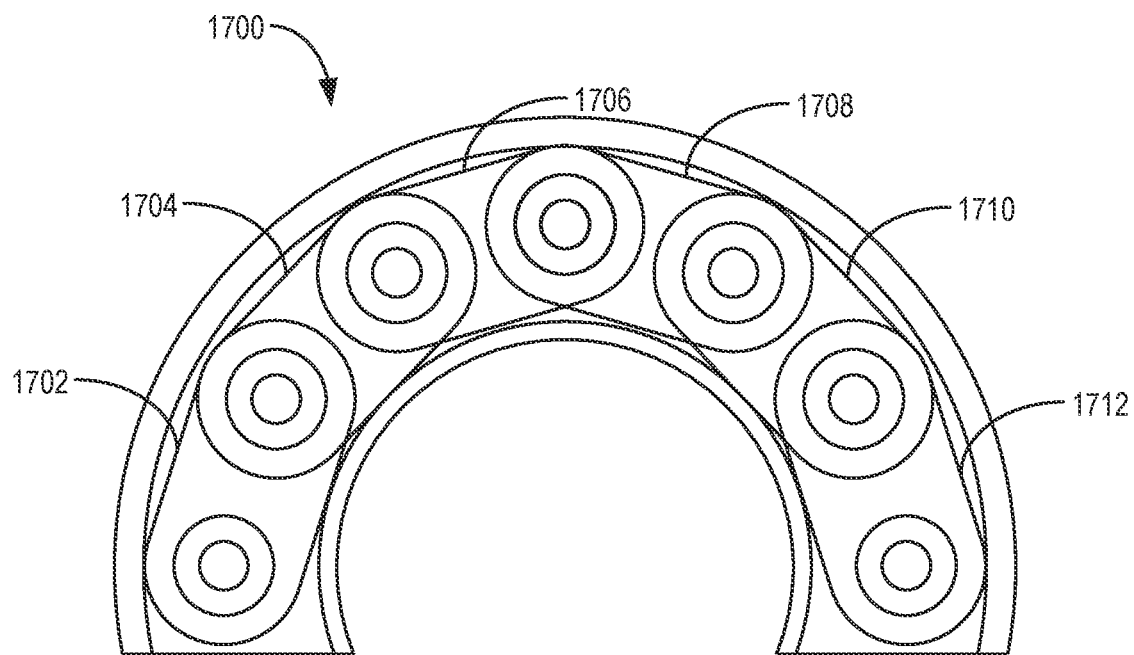
FIG. 17 shows a front view of another high voltage distribution system, according to an embodiment.
Figure 18:
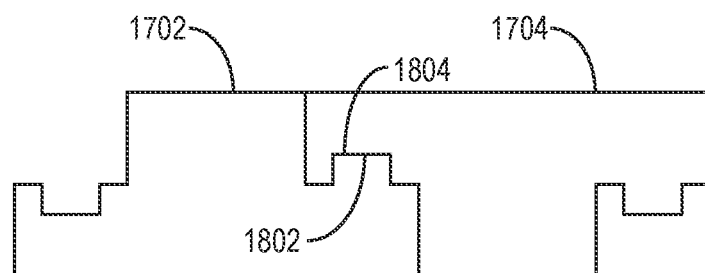
FIG. 18 shows an enlarged side view of interlocking sections of the high voltage distribution system of FIG. 17.

Referring to FIGS. 17-18, another HVDS 1700 is shown. In particular, FIG. 17 shows a front view of the HVDS 1700 and FIG. 18 shows an enlarged side view of interlocking sections of the HVDS. In the example shown, each x-ray tube is directly coupled to each adjacent x-ray tube. For example, x-ray tube 1702 is directly coupled to x-ray tube 1704, x-ray tube 1704 is directly coupled to x-ray tube 1706, x-ray tube 1706 is directly coupled to x-ray tube 1708, x-ray tube 1708 is directly coupled to x-ray tube 1710, and x-ray tube 1710 is directly coupled to x-ray tube 1712. Coupling of adjacent x-ray tubes may be performed by interlocking features of the adjacent x-ray tubes, as shown by FIG. 18 (e.g., with protrusion 1802 of x-ray tube 1702 interlocking directly with recess 1804 of x-ray tube 1704). As the number of x-ray tubes increases, the number of high-voltage connections also increases. For example, the number of high-voltage connections may be a function of the number of x-ray tubes (e.g., two high-voltage connections per x-ray tube). By connecting the x-ray tubes directly to each other without cables, the amount of cables may be greatly reduced or eliminated, which may reduce a cost of the system, increase an ease of assembly of the system, and/or reduce a size of the system.

The rigid high-voltage distribution systems described above may provide for space savings by significantly reducing the number of high-voltage connectors used (e.g., from 2 per x-ray tube in the case with cables, to 1 per x-ray tube). Additionally, a single connector (e.g., flat connector 1600) may supply the power to the HV distribution systems. The overall high-voltage capacitance may be significantly reduced, which may increase performance during dynamic voltage adjustments, such as during recovery of HV instabilities or during HV switching.

Figure 19:
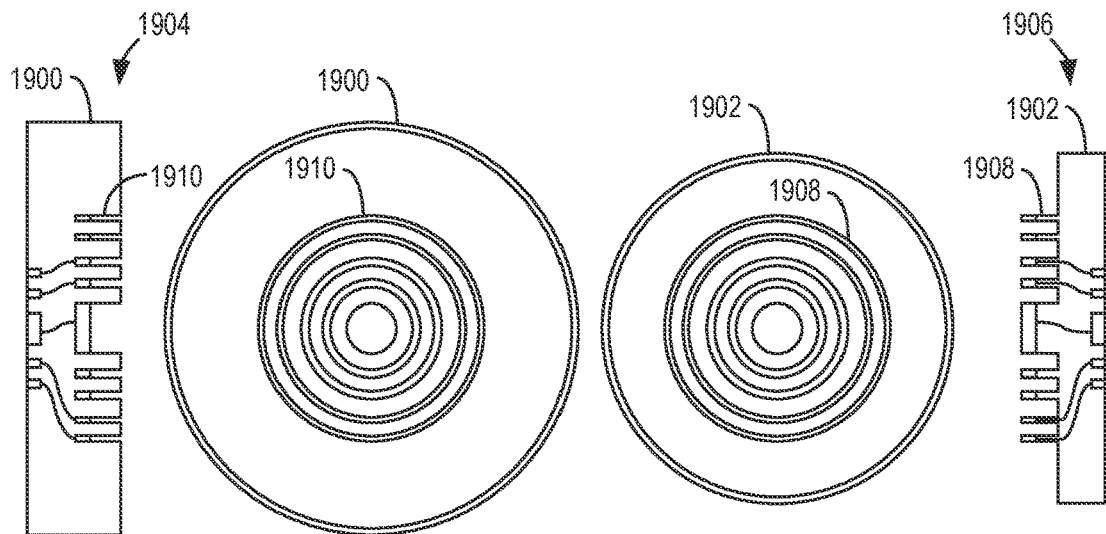
FIG. 19 shows a connector and a connection of a high voltage distribution system in an uncoupled configuration, according to an embodiment.
Figure 20:
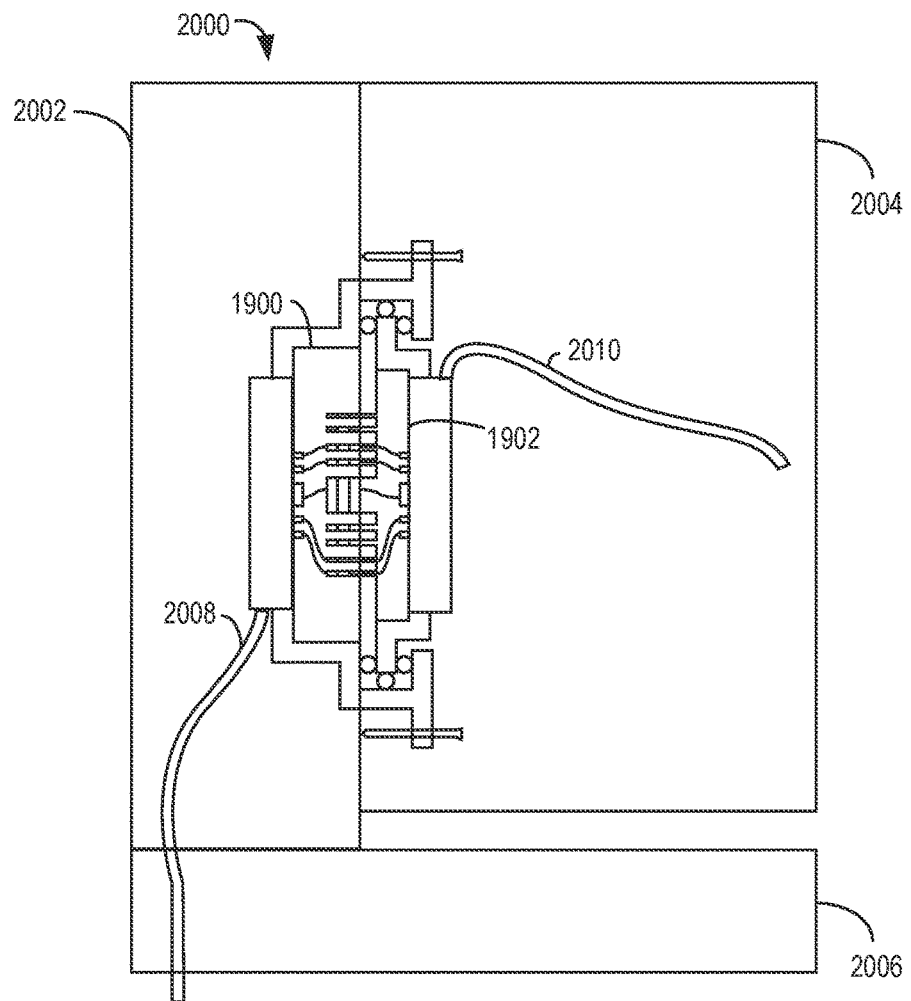
FIG. 20 shows the connector and connection of FIG. 19 in a coupled configuration.
Figure 21:
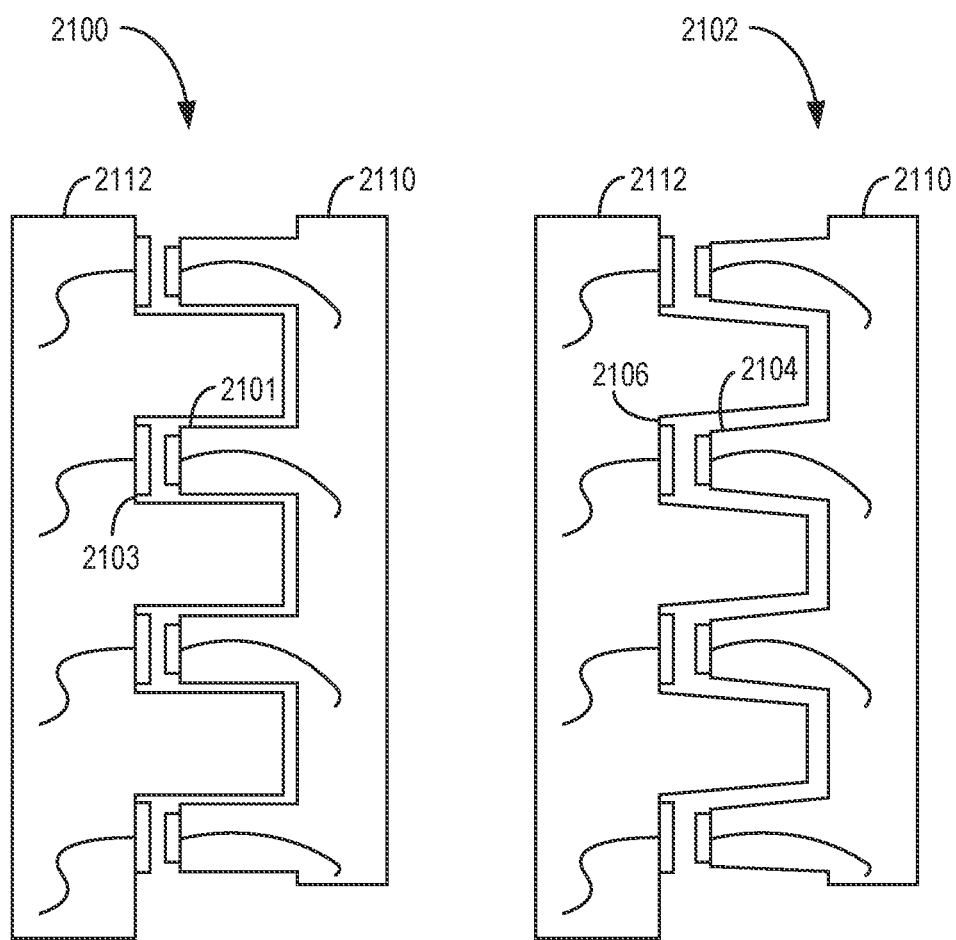
FIG. 21 shows various connection geometries of connectors and connections of a high voltage distribution system, according to an embodiment.

Referring to FIGS. 19-21, different views of components of another HVDS 2000 are shown. In particular, FIG. 19 shows connectors and connections of the HVDS 2000 in an uncoupled configuration, FIG. 20 shows the connectors and connections of the HVDS 2000 in the coupled configuration, and FIG. 21 shows example connection geometries of the connectors and connections of the HVDS 2000.

FIG. 19 shows connector 1920 configured to couple with connection 1900. The connector 1920 may be arranged at a first portion of the HVDS 2000 and the connection 1900 may be arranged at an adjacent, second portion of the HVDS 2000. A side profile 1906 of the connector 1902 and a side profile 1904 of the connection 1900 are included by FIG. 19 for illustrative purposes. Each of the connection 1900 and the connector 1902 may be relatively flat (e.g., mostly planar or disc-shaped). The connector 1902 includes a plurality of annular protrusions 1908 that may engage with counterpart annular recesses 1910 of the connection 1900.

As shown by FIG. 20, the annular protrusions 1908 may be inserted into the annular recesses 1910 in order to couple the connector 1902 with the connection 1900. Because the annular recesses 1910 and annular protrusions 1908 have radial symmetry, the connector 1902 and the connection 1900 may rotate relative to each other without disengaging the annular protrusions 1908 from the annular recesses 1910. The annular protrusions 1908 and annular recesses 1910 may be electrically conductive such that electrical energy (e.g., electrical current) may be transmitted between the connector 1902 and the connection 1900 during conditions in which the connector 1902 is engaged with the connection 1900. In this configuration, electrical energy may flow between a first section 2002 of the HVDS 2000 and a second section 2004 of the HVDS 2000 while providing for a relative rotational movement between the first section 2002 and the second section 2004. In one example, the first section 2002 may be a stationary portion of an imaging system (e.g., a rigid support) and the second section 2004 may be a movable portion of the imaging system (e.g., an imaging unit). In some examples, the connection 1900 at the first section 2002 may receive electrical power via a cable 2008, and the cable 2008 may extend through the first section 2002 and into a ground surface 2006 on which the imaging system sits. The cable 2008 may additionally extend through the ground surface 2006 and electrically couple to an electrical power source. Further, the connector 1902 may be electrically coupled to one or more other components of the imaging system and may provide electrical energy from the electrical power source to the other components via cable 2010.

Example interfaces between a connector 2110 and a connection 2112 are shown by FIG. 21. In one example, the connector 2110 may be similar to the connector 1902 described above, and the connection 2112 may be similar to the connection 1900 described above. A first interface 2100 is shown in which the connector 2110 includes annular protrusions 2101 having a square or rectangular profile, and the connection 2112 includes annular recesses 2103 having a counterpart square or rectangular profile. A second interface 2102 is shown in which the connector 2110 includes annular protrusions 2104 having a tapered profile, and the connection 2112 includes annular recesses 2106 having a counterpart tapered profile. The profile of the protrusions and recesses may provide a desired coupling quality (e.g., strength) of the connection 2112 and the connector 2110.

Figure 24:
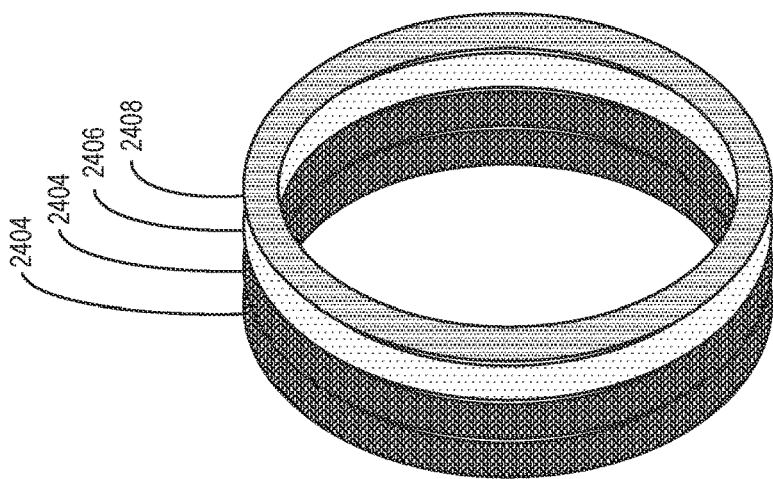
FIG. 24 shows a third configuration of a multi-modal imaging system, according to an embodiment.
Figure 23:
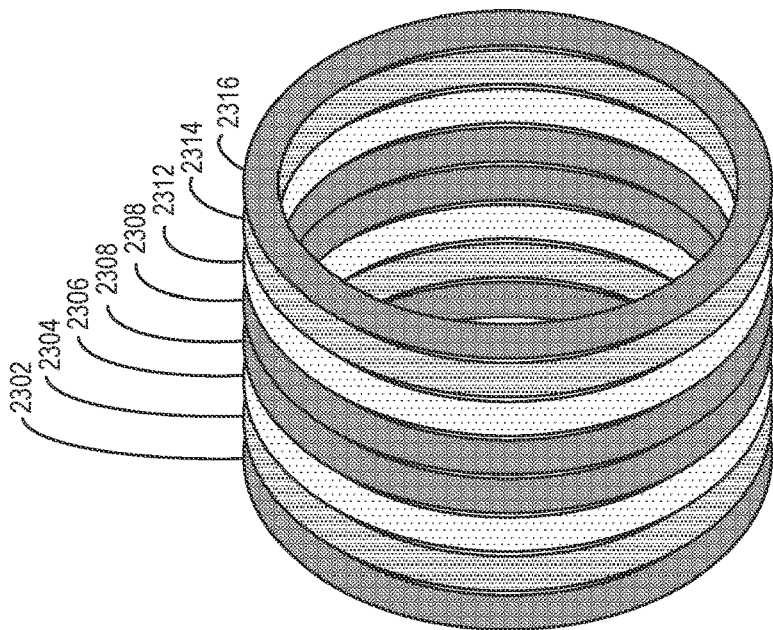
FIG. 23 shows a second configuration of a multi-modal imaging system, according to an embodiment.
Figure 22:
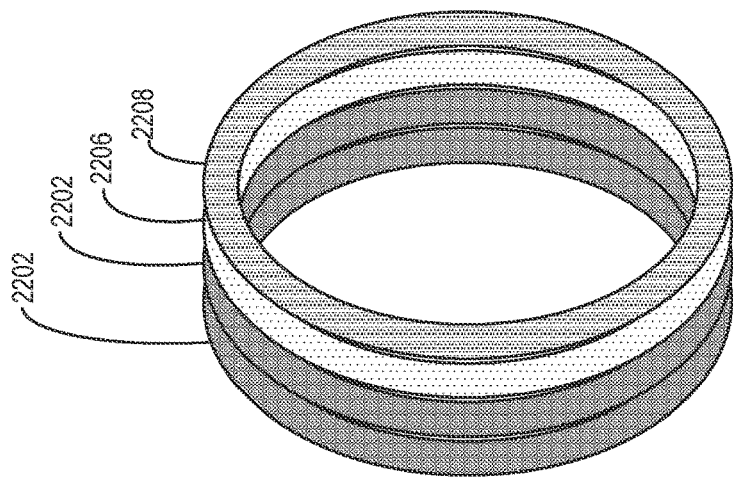
FIG. 22 shows a first configuration of a multi-modal imaging system, according to an embodiment.

Referring to FIGS. 22-24, various multi-modal imaging system configurations are shown. FIG. 22 shows a first configuration including an x-ray source 2208 (e.g., a distributed x-ray source unit, similar to the distributed x-ray source units described above), an x-ray detector array 2206 (e.g., similar to the detector arrays described above), and a positron emission tomography (PET) detector 2202.

FIG. 23 shows a second multi-modal imaging system configuration including a first PET detector 2302, a second PET detector 2316, a third PET detector 2308, a first x-ray source 2304, a second x-ray source 2314, a first x-ray detector array 2306, and a second x-ray detector array 2312.

FIG. 24 shows a third multi-modal imaging system configuration including a first x-ray source 2408, a second x-ray detector array 2406, and a magnetic resonance detector 2404.

In some examples, the imaging systems described herein may include the multi-modal configurations described above with reference to FIGS. 22-24.

As mentioned above, a stationary CT imaging system may include multiple stationary x-ray focal spots, which may be included in a distributed x-ray source with multiple emitters in a vacuum enclosure, as multiple x-ray sources, or a combination of both. In some examples, the x-ray sources or focal spots may extend over an angular range of 360 degrees surrounding a subject or object being imaged (e.g., the subject 127 shown in FIG. 1). In another example, the x-ray sources or focal spots may extend over a range that is approximately 180 degrees. Further, the stationary CT imaging system may include one or more x-ray detectors (e.g., detector arrays) positioned directly opposite the x-ray sources in order to measure x-rays after they penetrate through the subject. The x-ray detectors may also extend over 360 degrees, 180 degrees, or less, depending on the configuration of the x-ray sources or focal spots and the configuration of the detector. Further still, single energy or multi-energy x-ray sources may be used.

As such, FIGS. 25-36 show exemplary embodiments of distributed x-ray source and x-ray detector configurations that may be utilized in an imaging unit of a stationary CT imaging system (e.g., the imaging unit 123 of the imaging system 100 of FIG. 1). Letters (e.g., "a," "b," and the like) designate multiples of a functionally equivalent component, when included. Further, it may be understood that each distributed x-ray source and x-ray detector configuration may include anti-scatter grids, multiple aperture devices, and/or collimators, examples of which are described herein, at least in some examples. Additionally, it may be understood that although the x-ray sources and x-ray detectors are schematically shown as continuous surfaces, it may be understood that distinct emitters and/or detector cells may be distributed in arrays across the surfaces, such as coupled to one or more substrates.

In the examples described below, multiple sources may be activated simultaneously. As will be elaborated below, the configurations may be such that the primary beam of two simultaneously activated sources do not coincide on any detector to avoid confounding or multiplexing. To minimize scattered radiation, the scan field of view may be reduced, and ROI scanning and reconstruction may be performed, such as will be described herein with respect to FIGS. 51-55.

FIGS. 25-30 each show single energy configurations, while FIGS. 31-36 each show multi-energy configurations. The multi-energy configurations include operating different x-ray sources, which may be different focal spots or different x-ray tubes, at different voltages. The term "low energy" corresponds to an x-ray source operated at a low voltage relative to "medium energy" and "high energy" x-ray sources. The term "high energy" corresponds to an x-ray source that is operated at a higher voltage than both the medium energy and low energy x-ray sources. During a scan, the voltage for each x-ray source may not change for a given x-ray source. Instead, the given x-ray source may be switched on (e.g., powered) or off (e.g., unpowered) as desired, such as described above with respect to FIG. 1. It also may be understood that although the following embodiments show configurations having x-ray sources with two (e.g., dual-energy) or three different energy levels, the embodiments may include more than two or more than three different energies in some examples.

Referring first to FIG. 25, a first exemplary embodiment of a single energy x-ray source and detector configuration 2500 is schematically shown in a transaxial view 2501 and a lateral view 2503. The x-ray source and detector configuration 2500 includes a distributed x-ray source 2504 and an x-ray detector 2508, which each have a 360 degree range centered on a central axis 2516, which may be parallel with a z-axis that extends directed into the page and directly out of the page. The distributed x-ray source 2504 may be the distributed x-ray source unit 104 shown in FIG. 1, for example, and the x-ray detector 2508 may be the detector array of FIG. 1. The distributed x-ray source 2504 and the x-ray detector 2508 are both rotationally fixed with respect to the central axis 2516. For example, neither the distributed x-ray source 2504 nor the x-ray detector 2508 rotates about the central axis 2516. Further, in some examples, neither the distributed x-ray source 2504 nor the x-ray detector 2508 translates along the central axis 2516, while in other examples, the distributed x-ray source 2504 and the x-ray detector 2508 are translated in tandem to obtain different scan views.

The distributed x-ray source 2504 and the x-ray detector 2508 each include curved, non-planar arrangements in the x-ray source and detector configuration 2500. In the example shown, the distributed x-ray source 2504 and the x-ray detector 2508 are both circular in shape, although other curved shapes are possible (e.g., oval). Elongated shapes such as the oval may allow the distributed x-ray source 2504 and the x-ray detector 2508 to better conform to a contour of the subject and increase an angular coverage. Although the schematic representation shows the distributed x-ray source 2504 and the x-ray detector 2508 having different diameters in the transaxial view 2501, it may be understood that the distributed x-ray source 2504 and the x-ray detector 2508 may have a same diameter and may be offset along the central axis 2516 so that the distributed x-ray source 2504 and the x-ray detector 2508 do not coincide, as shown in the lateral view 2503. For example, the distributed x-ray source 2504 and the x-ray detector 2508 may have different z-axis positions.

Next, FIG. 26 schematically shows a second exemplary embodiment of a single energy x-ray source and detector configuration 2600 in a transaxial view 2601 and a lateral view 2603. The x-ray source and detector configuration 2600 includes a distributed x-ray source 2604 and an x-ray detector 2608, which each have a 180 degree range centered on a central axis 2616 that is parallel to a z-axis, as described above with respect to FIG. 25. The distributed x-ray source 2604 may be the distributed x-ray source unit 104 shown in FIG. 1, for example, and the x-ray detector 2608 may be the detector array of FIG. 1. The distributed x-ray source 2604 and the x-ray detector 2608 are both rotationally fixed with respect to the central axis 2616. For example, neither the distributed x-ray source 2604 nor the x-ray detector 2608 rotates about the central axis 2616. Further, in some examples, neither the distributed x-ray source 2604 nor the x-ray detector 2608 may translate along the central axis 2616, while in other examples, the distributed x-ray source 2604 and the x-ray detector 2608 are translated in tandem to obtain different scan views.

The distributed x-ray source 2604 and the x-ray detector 2608 each include curved, non-planar arrangements in the x-ray source and detector configuration 2600. In the example shown, the distributed x-ray source 2604 and the x-ray detector 2608 are each semi-circular in shape, although other curved shapes are possible that include a varying radial distance from the central axis 2616 (e.g., half-ovals). The distributed x-ray source 2604 and the x-ray detector 2608 have an overlapping z-axis position, as shown in the lateral view 2603, and are angularly non-overlapping with respect to the central axis 2616, as shown in the transaxial view 2601. For example, the distributed x-ray source 2604 may extend from 0 to 180 degrees with respect to the central axis 2616, and the x-ray detector 2608 may extend from 180 to 360 degrees with respect to the central axis 2616. As such, the distributed x-ray source 2604 and the x-ray detector 2608 do not coincide.

Continuing to FIG. 27, a third exemplary embodiment of a single energy x-ray source and detector configuration 2700 is schematically shown in a transaxial view 2701 and a lateral view 2703. The x-ray source and detector configuration 2700 includes a central axis 2716 surrounded by two distributed x-ray sources 2704a and 2704b and two x-ray detectors 2708a and 2708b. Each distributed x-ray source 2704a and 2704b may be one example of the distributed x-ray source unit 104 shown in FIG. 1, and each x-ray detector 2708a and 2708b may be one example of the detector array 147 of FIG. 1. The distributed x-ray sources 2704a and 2704b and the x-ray detectors 2708a and 2708b are rotationally fixed with respect to the central axis 2716. For example, none of the distributed x-ray sources 2704a and 2704b and the x-ray detectors 2708a and 2708b rotates about the central axis 2716. Further, in some examples, none of the distributed x-ray sources 2704a and 2704b and the x-ray detectors 2708a and 2708b may translate along the central axis 2716, while in other examples, the distributed x-ray sources 2704a and 2704b and the x-ray detectors 2708a and 2708b are translated in concert to obtain different scan views.

The distributed x-ray sources 2704a and 2704b and the x-ray detectors 2708a and 2708b each include planar arrangements in the x-ray source and detector configuration 2700. The distributed x-ray sources 2704a and 2704b and the x-ray detectors 2708a and 2708b are shown having a same length (e.g., longest dimension) in the present example, giving the x-ray source and detector configuration 2700 a square shape. However, in other examples, the x-ray source and detector configuration 2700 may be rectangular in shape. For example, the distributed x-ray source 2704a and the x-ray detector 2708a may each have a first length that is greater than a second length of the distributed x-ray source 2704b and the x-ray detector 2708b (or vice versa). Such elongated shapes may allow the x-ray source and detector configuration 2700 to better conform to a contour of the subject and increase an angular coverage.

In the x-ray source and detector configuration 2700, each distributed x-ray source 2704a and 2704b and each x-ray detector 2708a and 2708b has a 90 degree range. Thus, the distributed x-ray sources 2704a and 2704b have a combined 180 degree range, and the x-ray detectors 2708a and 2708b have a combined 180 degree range that is angularly non-overlapping with the 180 degree range for the distributed x-ray sources 2704a and 2704b. For example, the distributed x-ray source 2704a is positioned parallel to and directly opposite the x-ray detector 2708a, and the distributed x-ray source 2704b is positioned parallel to and directly opposite the x-ray detector 2708b. As such, the x-ray detector 2708a is positioned to measure x-rays emitted by the distributed x-ray source 2704a, and the x-ray detector 2708b is positioned to measure x-rays emitted by the distributed x-ray source 2704b. Further, as shown in the lateral view 2703, the distributed x-ray source 2704a and the x-ray detector 2708a have an overlapping z-axis position. It may be understood that the distributed x-ray source 2704b and the x-ray detector 2708b also have an overlapping z-axis position with respect to each other and with respect to the distributed x-ray source 2704a and the x-ray detector 2708a. Including planar distributed x-ray sources 2704a and 2704b and planar x-ray detectors 2708a and 2708b may enable a post-patient anti-scatter collimator with septa between detector rows to be used. As a result, scatter rejection may be performed efficiently.

Referring now to FIG. 28, a fourth exemplary embodiment of a single energy x-ray source and detector configuration 2800 is schematically shown in a transaxial view 2801 and a lateral view 2803. The x-ray source and detector configuration 2800 includes a central axis 2816 surrounded by three x-ray sources 2804a 2804b, and 2804c and three x-ray detectors 2808a, 2808b, and 2808c. Each x-ray source 2804a, 2804b, and 2804c may be one example of the distributed x-ray source unit 104 shown in FIG. 1, and each x-ray detector 2808a, 2808b, and 2808c may be one example of the detector array of FIG. 1. The x-ray sources 2804a, 2804b, and 2804c and the x-ray detectors 2808a, 2808b, and 2808c are rotationally fixed with respect to the central axis 2816. For example, none of the x-ray sources 2804a, 2804b, and 2804c and the x-ray detectors 2808a, 2808b, and 2808c rotates about the central axis 2816.

Further, in some examples, none of the x-ray sources 2804a, 2804b, and 2804c and the x-ray detectors 2808a, 2808b, and 2808c may translate along the central axis 2816, while in other examples the x-ray sources 2804a, 2804b, and 2804c and the x-ray detectors 2808a, 2808b, and 2808c are translated in concert to obtain different scan views.

The x-ray sources 2804a, 2804b, and 2804c and the x-ray detectors 2808a, 2808b, and 2808c each include curved arrangements such that the x-ray source and detector configuration 2800 is circular in shape. However, in other examples, x-ray source and detector configuration 2800 may be oval in shape, for example. In the x-ray source and detector configuration 2800, each x-ray source 2804a, 2804b, and 2804c and each x-ray detector 2808a, 2808b, and 2808c has a 60 degree range. Thus, the x-ray sources 2804a, 2804b, and 2804c have a combined 180 degree range, and the x-ray detectors 2808a, 2808b, and 2808c have a combined 180 degree range that is angularly non-overlapping with the 180 degree range for the x-ray sources 2804a and 2804b. Further, in some examples, there may be more than three x-ray detector portions and more than three x-ray source portions.

The x-ray sources 2804a, 2804b, and 2804c alternate with the x-ray detectors 2808a, 2808b, and 2808c about the central axis 2816. For example, the x-ray source 2804a is positioned directly opposite to the x-ray detector 2808a, the x-ray source 2804b is positioned directly opposite the x-ray detector 2808b, and the x-ray source 2804c is positioned directly opposite the x-ray detector 2808c. As such, the x-ray detector 2808a is positioned to measure x-rays emitted by the x-ray source 2804a, the x-ray detector 2808b is positioned to measure x-rays emitted by the x-ray source 2804b, and the x-ray detector 2808c is positioned to measure x-rays emitted by the x-ray source 2804c. Further, each x-ray source 2804a, 2804b, and 2804c is directly adjacent to two of the x-ray detectors 2808a, 2808b, and 2808c such that the x-ray sources and the x-ray detectors alternate about the central axis 2816. Further still, as shown in the lateral view 2803, the x-ray sources and the x-ray detectors have an overlapping z-axis position (e.g., along the central axis 2816).

Next, FIG. 29 schematically shows a fifth exemplary embodiment of a single energy x-ray source and detector configuration 2900 in a transaxial view 2901 and a lateral view 2903. The x-ray source and detector configuration 2900 includes a central axis 2916 surrounded by three distributed x-ray sources 2904a 2904b, and 2904c and three x-ray detectors 2908a, 2908b, and 2908c. Each distributed x-ray source 2904a, 2904b, and 2904c may be one example of the distributed x-ray source unit 104 shown in FIG. 1, and each x-ray detector 2908a, 2908b, and 2908c may be one example of the detector array of FIG. 1. The distributed x-ray sources 2904a, 2904b, and 2904c and the x-ray detectors 2908a, 2908b, and 2908c are rotationally fixed with respect to the central axis 2916. For example, none of the distributed x-ray sources 2904a, 2904b, and 2904c and the x-ray detectors 2908a, 2908b, and 2908c rotates about the central axis 2916. Further, in some examples, none of the distributed x-ray sources 2904a, 2904b, and 2904c and the x-ray detectors 2908a, 2908b, and 2908c may translate along the central axis 2916, while in other examples the distributed x-ray sources 2904a, 2904b, and 2904c and the x-ray detectors 2908a, 2908b, and 2908c are translated in concert to obtain different scan views.

The distributed x-ray sources 2904a, 2904b, and 2904c and the x-ray detectors 2908a, 2908b, and 2908c each include planar arrangements such that the x-ray source and detector configuration 2900 is hexagonal in shape. Although an aspect ratio of the hexagonal shape is 1 in the example shown, the hexagonal shape may have other aspect ratios in other examples. For example, a height of the x-ray source and detector configuration 2900 may be greater than the width. The planar configuration of each x-ray detector 2908a, 2908b, and 2908c may enable an anti-scatter collimator with septa between detector rows to be used, such as mentioned above with respect to FIG. 27. Further, in some examples, there may be more than three x-ray detector portions and more than three x-ray source portions.

In the x-ray source and detector configuration 2900, each distributed x-ray source 2904a, 2904b, and 2904c and each x-ray detector 2908a, 2908b, and 2908c has a 60 degree range. Thus, the distributed x-ray sources 2904a, 2904b, and 2904c have a combined 180 degree range, and the x-ray detectors 2908a, 2908b, and 2908c have a combined 180 degree range that is angularly non-overlapping with the 180 degree range for the distributed x-ray sources 2904a and 2904b. For example, the distributed x-ray source 2904a is positioned directly opposite to the x-ray detector 2908a, the distributed x-ray source 2904b is positioned directly opposite the x-ray detector 2908b, and the distributed x-ray source 2904c is positioned directly opposite the x-ray detector 2908c. As such, the x-ray detector 2908a is positioned to measure x-rays emitted by the distributed x-ray source 2904a, the x-ray detector 2908b is positioned to measure x-rays emitted by the distributed x-ray source 2904b, and the x-ray detector 2908c is positioned to measure x-rays emitted by the distributed x-ray source 2904c. Further, each distributed x-ray source 2904a, 2904b, and 2904c is directly adjacent to two of the x-ray detectors 2908a, 2908b, and 2908c such that the x-ray sources and the x-ray detectors alternate about the central axis 2916. Further still, as shown in the lateral view 2903, the x-ray sources and the x-ray detectors have an overlapping z-axis position (e.g., along the central axis 2916).

FIG. 30 schematically shows a sixth exemplary embodiment of a single energy x-ray source and detector configuration 3000 in a transaxial view 3001 and a lateral view 3003. The x-ray source and detector configuration 3000 includes a distributed x-ray source 3004 having a 360 degree range and an x-ray detector 3008 having a 60 degree range. The distributed x-ray source 3004 may be the distributed x-ray source unit 104 shown in FIG. 1, for example, and the x-ray detector 3008 may be the detector array of FIG. 1. The distributed x-ray source 3004 and the x-ray detector 3008 are both centered on a central axis 3016 that is parallel to a z-axis, as described above with respect to FIG. 25. The distributed x-ray source 3004 and is rotationally fixed with respect to the central axis 3016, but the x-ray detector 3008 rotates about the central axis 3016, making x-ray source and detector configuration 3000 "semi-stationary." Further, in some examples, neither the distributed x-ray source 3004 nor the x-ray detector 3008 translates along the central axis 3016, while in other examples, the distributed x-ray source 3004 and the x-ray detector 3008 are translated in tandem to obtain different scan views.

The distributed x-ray source 3004 and the x-ray detector 3008 each include curved, non-planar arrangements in the x-ray source and detector configuration 3000. In the example shown, the distributed x-ray source 3004 is circular in shape, and the x-ray detector 3008 is a curve having a smaller radial distance from the central axis 3016. The distributed x-ray source 3004 and the x-ray detector 3008 have an overlapping z-axis position, as shown in the lateral view 3003. Although the x-ray source and detector configuration 3000 includes the rotating x-ray detector 3008, detector costs may be decreased and scatter rejection may be increased compared with systems that include a rotating x-ray source and x-ray detector. Further, the CT imaging system may be more compact than systems that include a rotating x-ray source and x-ray detector.

Referring now to FIG. 31, a first exemplary embodiment of a multi-energy x-ray source and detector configuration 3100 is schematically shown in a transaxial view 3101. The x-ray source and detector configuration 3100 includes a high energy distributed x-ray source 3104, a low energy distributed x-ray source 3105, and an x-ray detector 3108, which each have a 360 degree range centered on a central axis 3116. The high energy distributed x-ray source 3104 and the low energy distributed x-ray source 3105 each may be one example of the distributed x-ray source unit 104 shown in FIG. 1, and the x-ray detector 3108 may be the detector array of FIG. 1. The central axis 3116 may be parallel with a z-axis that extends directed into the page and directly out of the page. The high energy distributed x-ray source 3104, the low energy distributed x-ray source 3105, and the x-ray detector 3108 are each rotationally fixed with respect to the central axis 3116. For example, the high energy distributed x-ray source 3104, the low energy distributed x-ray source 3105, and the x-ray detector 3108 do not rotate about the central axis 3116. Further, in some examples, the high energy distributed x-ray source 3104, the low energy distributed x-ray source 3105, and the x-ray detector 3108 do not translate along the central axis 3116, while in other examples, the high energy distributed x-ray source 3104, the low energy distributed x-ray source 3105, and the x-ray detector 3108 are translated in concert to obtain different scan views. Multi-energy x-ray source and detector configuration 3100 includes a highest amount of source redundancy compared with the configurations that will be described with respect to FIGS. 32-36. However, including such as high amount of source redundancy increases a cost and complexity of the system.

The high energy distributed x-ray source 3104, the low energy distributed x-ray source 3105, and the x-ray detector 3108 each include curved, non-planar arrangements in the x-ray source and detector configuration 3100. In the example shown, the high energy distributed x-ray source 3104, the low energy distributed x-ray source 3105, and the x-ray detector 3108 are all circular in shape, although other curved shapes are possible (e.g., oval). Although the schematic representation shows the high energy distributed x-ray source 3104, the low energy distributed x-ray source 3105, and the x-ray detector 3108 having different diameters in the transaxial view 3101, it may be understood that the high energy distributed x-ray source 3104, the low energy distributed x-ray source 3105, and the x-ray detector 3108 may have a same diameter and may be offset along the central axis 3116 so that the high energy distributed x-ray source 3104, the low energy distributed x-ray source 3105, and the x-ray detector 3108 do not coincide, such as described with respect to FIG. 25. For example, each of the high energy distributed x-ray source 3104, the low energy distributed x-ray source 3105, and the x-ray detector 3108 may have different z-axis positions.

Multi-energy x-ray source and detector configuration 3100 includes a highest amount of source redundancy compared with the configurations that will be described with respect to FIGS. 32-36. However, including such as high amount of source redundancy increases a cost and complexity of the system. Therefore, other embodiments that include less source redundancy while still providing high quality reconstructed images may be desirable.

Referring next to FIG. 32, a second exemplary embodiment of a multi-energy x-ray source and detector configuration 3200 is schematically shown in a transaxial view 3201. The x-ray source and detector configuration 3200 includes a high energy distributed x-ray source 3204, a low energy distributed x-ray source 3205, and an x-ray detector 3208. The high energy distributed x-ray source 3204 and the low energy distributed x-ray source 3205 each may be one example of the distributed x-ray source unit 104 shown in FIG. 1, and the x-ray detector 3208 may be the detector array of FIG. 1. The high energy distributed x-ray source 3204 and the low energy distributed x-ray source 3205 each have a 180 degree range centered on a central axis 3216 that is parallel to a z-axis, as described above with respect to FIG. 31, while the x-ray detector 3208 has a 360 degree range about the central axis 3216. The high energy distributed x-ray source 3204, the low energy distributed x-ray source 3205, and the x-ray detector 3208 are each rotationally fixed with respect to the central axis 3216. For example, none of the high energy distributed x-ray source 3204, the low energy distributed x-ray source 3205, and the x-ray detector 3208 rotates about the central axis 3216. Further, in some examples, the high energy distributed x-ray source 3204, the low energy distributed x-ray source 3205, and the x-ray detector 3208 may not translate along the central axis 3216, while in other examples, the high energy distributed x-ray source 3204, the low energy distributed x-ray source 3205, and the x-ray detector 3208 are translated in concert to obtain different scan views.

The high energy distributed x-ray source 3204, the low energy distributed x-ray source 3205, and the x-ray detector 3208 each include curved, non-planar arrangements in the x-ray source and detector configuration 3200. In the example shown, the high energy distributed x-ray source 3204 and the low energy distributed x-ray source 3205 are each semi-circular in shape, although other curved shapes are possible that include a varying radial distance from the central axis 3216 (e.g., half-ovals). Further, the x-ray detector 3208 is circular in the example shown, but may be an oval in other examples. The high energy distributed x-ray source 3204 and the low energy distributed x-ray source 3205 may have an overlapping z-axis position and are angularly non-overlapping with respect to the central axis 3216. For example, the high energy distributed x-ray source 3204 may extend from 0 to 180 degrees with respect to the central axis 3216, and the low energy distributed x-ray source 3205 may extend from 180 to 360 degrees with respect to the central axis 3216. As such, the high energy distributed x-ray source 3204 and the low energy distributed x-ray source 3205 do not coincide. Further, the x-ray detector 3208 may have a different z-axis position from the high energy distributed x-ray source 3204 and the low energy distributed x-ray source 3205, at least in some examples.

Continuing to FIG. 33, a third exemplary embodiment of a multi-energy x-ray source and detector configuration 3300 is schematically shown in a transaxial view 3301. The x-ray source and detector configuration 3300 includes a central axis 3316 surrounded by a high energy x-ray sources 3304, a low energy distributed x-ray source 3305, and two x-ray detectors 3308a and 3308b. The high energy distributed x-ray source 3304 and the low energy distributed x-ray source 3305 each may be one example of the distributed x-ray source unit 104 shown in FIG. 1, and the x-ray detectors 3308a and 3308b each may be one example of the detector array of FIG. 1. The high energy distributed x-ray source 3304, the low energy distributed x-ray source 3305, and the x-ray detectors 3308a and 3308b are rotationally fixed with respect to the central axis 3316. For example, none of the high energy distributed x-ray source 3304, the low energy distributed x-ray source 3305, and the x-ray detectors 3308a and 3308b rotates about the central axis 3316. Further, in some examples, the high energy distributed x-ray source 3304, the low energy distributed x-ray source 3305, and the x-ray detectors 3308a and 3308b do not translate along the central axis 3316, while in other examples, the high energy distributed x-ray source 3304, the low energy distributed x-ray source 3305, and the x-ray detectors 3308a and 3308b are translated in concert to obtain different scan views.

The high energy distributed x-ray source 3304, the low energy distributed x-ray source 3305, and the x-ray detectors 3308a and 3308b each include planar arrangements in the x-ray source and detector configuration 3300. The high energy distributed x-ray source 3304, the low energy distributed x-ray source 3305, and the x-ray detectors 3308a and 3308b are shown having a same length (e.g., longest dimension) in the present example, giving the x-ray source and detector configuration 3300 a square shape. However, in other examples, the x-ray source and detector configuration 3300 may be rectangular in shape. For example, the high energy distributed x-ray source 3304 and the x-ray detector 3308a may each have a first length that is greater than a second length of the low energy distributed x-ray source 3305 and the x-ray detector 3308b (or vice versa). Such elongated shapes may allow the x-ray source and detector configuration 3300 to better conform to a contour of the subject and increase an angular coverage.

In the x-ray source and detector configuration 3300, each of the high energy distributed x-ray source 3304, the low energy distributed x-ray source 3305, the x-ray detector 3308a, and the x-ray detector 3308b has a 90 degree range. Thus, the high energy distributed x-ray source 3304 and the low energy distributed x-ray source 3305 have a combined 180 degree range, and the x-ray detectors 3308a and 3308b have a combined 180 degree range that is angularly non-overlapping with the 180 degree range for the high energy distributed x-ray source 3304 and the low energy distributed x-ray source 3305. For example, the high energy distributed x-ray source 3304 is positioned parallel to and directly opposite the x-ray detector 3308a, and the low energy distributed x-ray source 3305 is positioned parallel to and directly opposite the x-ray detector 3308b. As such, the x-ray detector 3308a is positioned to measure x-rays emitted by the high energy distributed x-ray source 3304, and the x-ray detector 3308b is positioned to measure x-rays emitted by the low energy distributed x-ray source 3305. Further, the high energy distributed x-ray source 3304, the low energy distributed x-ray source 3305, the x-ray detector 3308a, and the x-ray detector 3308b may have an overlapping z-axis position due to their non-overlapping angular positions, such as described above with respect to FIG. 27.

Referring now to FIG. 34, a fourth exemplary embodiment of a multi-energy x-ray source and detector configuration 3400 is schematically shown in a transaxial view 3401. The x-ray source and detector configuration 3400 includes a central axis 3416 surrounded by three x-ray sources, including a high energy x-ray source 3404, a low energy x-ray source 3405, and a medium energy x-ray source 3407, and three x-ray detectors 3408a, 3408b, and 3408c. The high energy x-ray source 3404, the low energy x-ray source 3405, and the medium energy x-ray source 3407 each may be one example of the distributed x-ray source unit 104 shown in FIG. 1, and the x-ray detectors 3408a, 3408b, and 3408c each may be one example of the detector array of FIG. 1. The x-ray sources and the x-ray detectors 3408a, 3408b, and 3408c are rotationally fixed with respect to the central axis 3416. For example, the high energy x-ray source 3404, the low energy x-ray source 3405, the medium energy x-ray source 3407, and the x-ray detectors 3408a, 3408b, and 3408c may not rotate about the central axis 3416. Further, in some examples, the high energy x-ray source 3404, the low energy x-ray source 3405, the medium energy x-ray source 3407, and the x-ray detectors 3408a, 3408b, and 3408c may not translate along the central axis 3416, while in other examples the x-ray sources and the x-ray detectors are translated in concert to obtain different scan views.

The high energy x-ray source 3404, the low energy x-ray source 3405, the medium energy x-ray source 3407, and the x-ray detectors 3408a, 3408b, and 3408c each include curved arrangements such that the x-ray source and detector configuration 3400 is circular in shape. However, in other examples, x-ray source and detector configuration 3400 may be oval in shape, for example. In the x-ray source and detector configuration 3400, each of the high energy x-ray source 3404, the low energy x-ray source 3405, the medium energy x-ray source 3407 and each x-ray detector 3408a, 3408b, and 3408c has a 60 degree range. Thus, the high energy x-ray source 3404, the low energy x-ray source 3405, and the medium energy x-ray source 3407 have a combined 180 degree range, and the x-ray detectors 3408a, 3408b, and 3408c have a combined 180 degree range that is angularly non-overlapping with the 180 degree range of the x-ray sources. Further, in some examples, there may be more than three x-ray detector portions and more than three x-ray source portions.

The x-ray sources and the x-ray detectors alternate about the central axis 3416. For example, the high energy x-ray source 3404 is positioned directly opposite to the x-ray detector 3408a, the low energy x-ray source 3405 is positioned directly opposite the x-ray detector 3408b, and the medium energy x-ray source 3407 is positioned directly opposite the x-ray detector 3408c. As such, the x-ray detector 3408a is positioned to measure x-rays emitted by the high energy x-ray source 3404, the x-ray detector 3408b is positioned to measure x-rays emitted by the low energy x-ray source 3405, and the x-ray detector 3408c is positioned to measure x-rays emitted by the medium energy x-ray source 3407. Further, each x-ray source is directly adjacent to two of the x-ray detectors 3408a, 3408b, and 3408c such that the x-ray sources and the x-ray detectors alternate about the central axis 3416. Further still, the x-ray sources and the x-ray detectors may have an overlapping z-axis position (e.g., along the central axis 3416) because they are angularly non-overlapping and therefore do not coincide.

Next, FIG. 35 schematically shows a fifth exemplary embodiment of a multi-energy x-ray source and detector configuration 3500 in a transaxial view 3501. The x-ray source and detector configuration 3500 includes a central axis 3516 surrounded by three x-ray sources, including a high energy distributed x-ray source 3504, a low energy distributed x-ray source 3505, and a medium energy distributed x-ray source 3507, and three x-ray detectors 3508a, 3508b, and 3508c. The high energy distributed x-ray source 3504, the low energy distributed x-ray source 3505, and the medium energy distributed x-ray source 3507 each may be one example of the distributed x-ray source unit 104 shown in FIG. 1, and the x-ray detectors 3508a, 3508b, and 3508c each may be one example of the detector array of FIG. 1. The high energy distributed x-ray source 3504, the low energy distributed x-ray source 3505, and the medium energy distributed x-ray source 3507 and the x-ray detectors 3508a, 3508b, and 3508c are rotationally fixed with respect to the central axis 3516. For example, none of the x-ray sources and the x-ray detectors 3508a, 3508b, and 3508c may rotate about the central axis 3516. Further, in some examples, the high energy distributed x-ray source 3504, the low energy distributed x-ray source 3505, the medium energy distributed x-ray source 3507, and the x-ray detectors 3508a, 3508b, and 3508c may not translate along the central axis 3516, while in other examples the x-ray sources and the x-ray detectors are translated in concert to obtain different scan views.

The high energy distributed x-ray source 3504, the low energy distributed x-ray source 3505, the medium energy distributed x-ray source 3507, and the x-ray detectors 3508a, 3508b, and 3508c each include planar arrangements such that the x-ray source and detector configuration 3500 is hexagonal in shape. Although an aspect ratio of the hexagonal shape is 1 in the example shown, the hexagonal shape may have different aspect ratios in other examples. For example, a height of the x-ray source and detector configuration 3500 may be greater than the width. The planar configuration of each x-ray detector 3508a, 3508b, and 3508c may enable an anti-scatter collimator with septa between detector rows to be used, such as mentioned above with respect to FIG. 27. Further, in some examples, there may be more than three x-ray detector portions and more than three x-ray source portions.

In the x-ray source and detector configuration 3500, each of the high energy distributed x-ray source 3504, the low energy distributed x-ray source 3505, and the medium energy distributed x-ray source 3507 and each x-ray detector 3508a, 3508b, and 3508c has a 60 degree range. Thus, the high energy distributed x-ray source 3504, the low energy distributed x-ray source 3505, and the medium energy distributed x-ray source 3507 have a combined 180 degree range, and the x-ray detectors 3508a, 3508b, and 3508c have a combined 180 degree range that is angularly non-overlapping with the 180 degree range of the x-ray sources. For example, the high energy distributed x-ray source 3504 is positioned directly opposite to the x-ray detector 3508a, the low energy distributed x-ray source 3505 is positioned directly opposite the x-ray detector 3508b, and the medium energy distributed x-ray source 3507 is positioned directly opposite the x-ray detector 3508c. As such, the x-ray detector 3508a is positioned to measure x-rays emitted by the high energy distributed x-ray source 3504, the x-ray detector 3508b is positioned to measure x-rays emitted by the low energy distributed x-ray source 3505, and the x-ray detector 3508c is positioned to measure x-rays emitted by the medium energy distributed x-ray source 3507. Further, each x-ray source is directly adjacent to two of the x-ray detectors 3508a, 3508b, and 3508c such that the x-ray sources and the x-ray detectors alternate about the central axis 3516. Further still, the x-ray sources and the x-ray detectors may have an overlapping z-axis position (e.g., along the central axis 3516) because they are angularly non-overlapping.

FIG. 36 schematically shows a sixth exemplary embodiment of a multi-energy x-ray source and detector configuration 3600 in a transaxial view 3601. The x-ray source and detector configuration 3600 includes a three high energy x-ray sources 3604a, 3604b, and 3604c and three low energy x-ray sources 3605a, 3605b, and 3605c that each have a 60 degree range with respect to a central axis 3616. Thus, the high energy x-ray sources 3604a, 3604b, and 3604c have a combined range of 180 degrees, and the low energy x-ray sources 3605a, 3605b, and 3605c also have a combined range of 180 degrees. The high energy x-ray sources 3604a, 3604b, and 3604c and the low energy x-ray sources 3605a, 3605b, and 3605c each may be one example of the distributed x-ray source unit 104 shown in FIG. 1. Further, x-ray source and detector configuration 3600 includes an x-ray detector 3608 having a 60 degree range. The x-ray detector 3608 may be the detector array of FIG. 1, for example. The high energy x-ray sources 3604a, 3604b, and 3604c and the low energy x-ray sources 3605a, 3605b, and 3605c are rotationally fixed with respect to the central axis 3616, but the x-ray detector 3608 rotates about the central axis 3616, making x-ray source and detector configuration 3600 "semi-stationary." Further, in some examples, the high energy x-ray sources 3604a, 3604b, and 3604c, the low energy x-ray sources 3605a, 3605b, and 3605c, and the x-ray detector 3608 do not translate along the central axis 3616, while in other examples, the x-ray sources and the x-ray detector 3608 are translated in concert to obtain different scan views.

In the example shown, the high energy x-ray sources 3604a, 3604b, and 3604c and the low energy x-ray sources 3605a, 3605b, and 3605c together form a circular shape, and the x-ray detector 3608 is a curve having a smaller radial distance from the central axis 3616. In the example shown, each high energy x-ray source is directly adjacent to two of the low energy x-ray sources such that the high energy x-ray sources and the low energy x-ray sources alternate about the central axis 3616. For example, the high energy distributed x-ray source 3604a is adjacent to the low energy x-ray sources 3650c and 3605a, the high energy distributed x-ray source 3604b is adjacent to the low energy x-ray sources 3650a and 3605b, and the high energy distributed x-ray source 3604c is adjacent to the low energy x-ray sources 3650b and 3605c. Further, the high energy x-ray sources 3604a, 3604b, and 3604c, the low energy x-ray sources 3605a, 3605b, and 3605c, and the x-ray detector 3608 all may have an overlapping z-axis position. Although the x-ray source and detector configuration 3600 includes the rotating x-ray detector 3608, detector costs may be decreased and scatter rejection may be increased compared with systems that include both a rotating x-ray source and x-ray detector. Further, the CT imaging system may be more compact than systems that include a rotating x-ray source and x-ray detector.

Still other multi-energy x-ray source arrangements are possible that use the general geometry of the embodiments shown in FIGS. 31-36. For example, each x-ray source may have two targets (anodes) at different voltages, such as described above with respect to FIG. 1. FIGS. 37-39B show additional exemplary embodiments of a multi-energy x-ray source and x-ray detector configuration that each may be utilized in a stationary CT imaging system (e.g., the imaging system 100 of FIG. 1). For example, each embodiment shown in FIGS. 37-39B includes 360 degree x-ray source and x-ray detector coverage and further includes different energy x-ray sources, such as described above with respect to FIG. 31. Thus, FIG. 37 particularly highlights the relative arrangement of high energy and low energy x-ray sources with respect to each other, and FIGS. 38A-39B show embodiments where the x-ray sources are otherwise controlled or modulated. Throughout FIGS. 37-39B, components that are similar to, or the same as, components introduced with respect to FIG. 1 are numbered similarly and may function as previously described.

Figure 37:
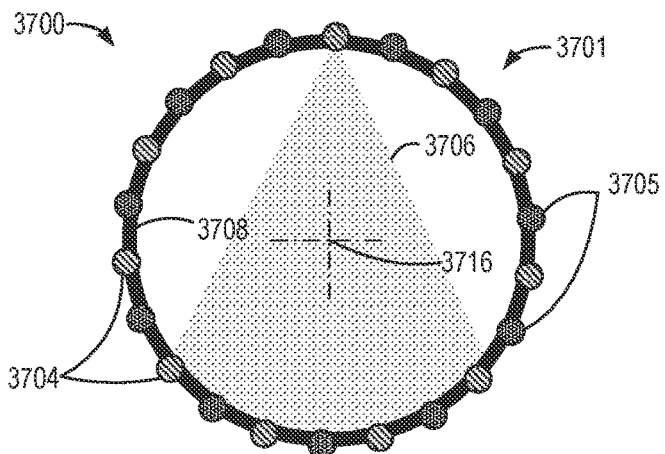
FIG. 37 schematically shows a seventh exemplary multi-energy distributed x-ray source and detector configuration for an imaging unit, according to an embodiment.

Referring first to FIG. 37, a seventh exemplary embodiment of a multi-energy x-ray source and detector configuration 3700 is schematically shown in a transaxial view 3701. The x-ray source and detector configuration 3700 includes a plurality of high energy x-ray sources 3704, a plurality of low energy x-ray sources 3705, and an x-ray detector 3708, which each have a 360 degree range centered on a central axis 3716, such as described above with respect to FIG. 31. For example, the plurality of high energy x-ray sources 3704 and the plurality of low energy x-ray sources 3705 are radially distributed with respect to the central axis 3716 in an alternating fashion. Each high energy distributed x-ray source 3704 and each low energy distributed x-ray source 3705 may be a separate tube having one or more focal spots, for example. Further, there is an odd number of both of the high energy x-ray sources 3704 and the low energy x-ray sources 3705 so that diametrically opposed tubes have different voltages. For example, each of the high energy x-ray sources 3704 is directly opposite one of the low energy x-ray sources 3705 across a diameter of the multi-energy x-ray source and detector configuration 3700. Although there are eleven high energy x-ray sources 3704 and eleven low energy x-ray sources 3705 illustrated in the example shown in FIG. 37, note that in other examples, there may be more or fewer than eleven of each. Further, FIG. 37 shows an x-ray beam 3706 being emitted from one of the high energy x-ray sources 3704, although multiple sources may be activated simultaneously, such as mentioned above.

Figure 38A:
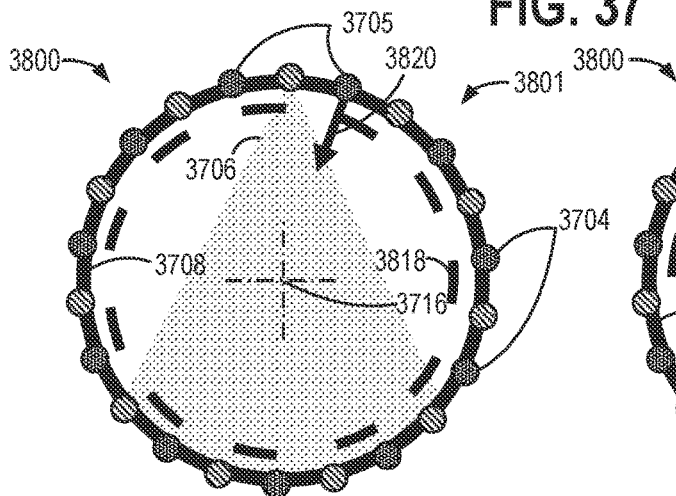
FIGS. 38A and 38B schematically show an eighth exemplary multi-energy distributed x-ray source and detector configuration for an imaging unit, according to an embodiment.
Figure 38B:
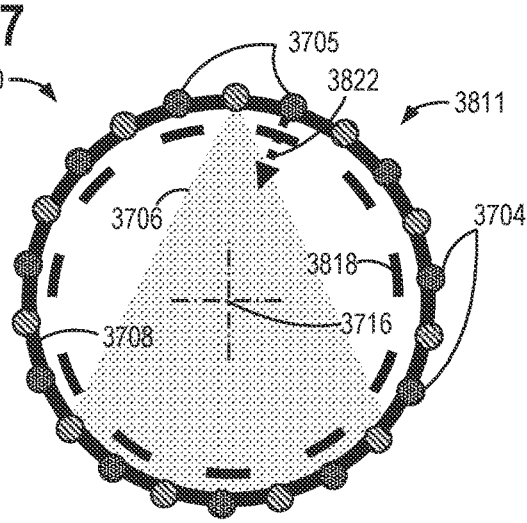

Next, FIGS. 38A and 38B show an eighth exemplary embodiment of a multi-energy x-ray source and detector configuration 3800. The multi-energy x-ray source and detector configuration 3800 is similar to the multi-energy x-ray source and detector configuration 3700 of FIG. 37 except for the addition of a filter 3818. As such, components previously introduced with respect to FIG. 37 are numbered the same and will not be reintroduced. The filter 3818 is organized on a ring-like structure, which rotates with respect to the central axis 3716 to achieve different filtration for different x-ray sources. In the example shown, the low energy x-ray sources 3705 switch between a "no filtration" state shown in a first transaxial view 3801 of FIG. 38A and a "filtration" state shown in a second transaxial view 3811 of FIG. 38B. For example, FIG. 38A shows an unfiltered beam represented by a solid arrow 3820, which does not pass through filter 3818, while FIG. 38B shows a filtered beam represented by a dashed arrow 3822, which passes through the filter 3818, due a change in the rotational position of the filter 3818. The filter 3818 may remove or attenuate low-energy x-ray photons from the resulting x-ray spectrum, which may decrease an overall x-ray dose provided to the imaging subject and reduce scatter while not reducing image quality. For example, the filtered beam represented by the dashed arrow 3822 may have a lower x-ray intensity and a different beam shape compared with the unfiltered beam represented by the solid arrow 3820.

By varying a frequency of "filtration" and "no filtration" sections relative to the total number of x-ray sources, various source positions may not include filtration while other source positions include filtration at a given rotational position of the filter 3818. This may produce a beat pattern in the acquired x-ray spectra. By slowly rotating the filter 3818 with respect to the central axis 3716, the locations of the filtered and unfiltered x-ray source positions can be modulated achieve a particular imaging goal.

Further, in some examples, dynamic filtration (that switches between filters for a given x-ray source position) may be used, particularly because there is substantial repeat time for a given x-ray source. For example, the filter 3818 may include a single filtration material or a plurality of different filtration materials. Each different filtration material may include one or more of a different composition (e.g., a different metal), a different thickness, a different filtered x-ray spectrum, etc. For example, a first filtration section may include a first filtration material (e.g., aluminum), and a second filtration section that is adjacent to the first filtration section may include a second, different filtration material (e.g., copper). Rotating the filter 3818 clockwise may place the first filtration section in front of a given source, while rotating the filter 3818 counterclockwise may place the second filtration section in front of the source, for example. It may be understood that although the filter 3818 is shown with respect to multi-energy configuration, the filter 3818 also may be used in a single energy x-ray source and detector configuration, such as the x-ray source and detector configuration 2500 shown in FIG. 25.

Figure 39A:
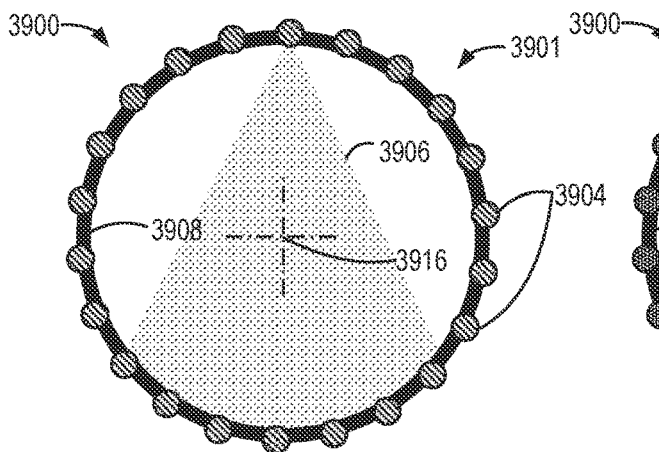
FIGS. 39A and 39B schematically show a ninth exemplary multi-energy distributed x-ray source and detector configuration for an imaging unit, according to an embodiment.
Figure 39B:
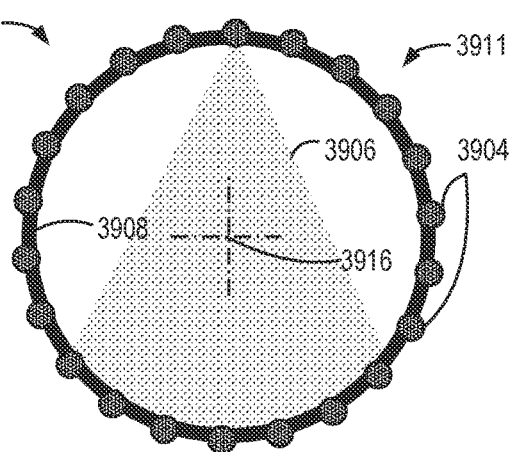

Next, FIGS. 39A and 39B show a ninth exemplary embodiment of a multi-energy x-ray source and detector configuration 3900. The multi-energy x-ray source and detector configuration 3900 includes a plurality of x-ray sources 3904 and an x-ray detector 3908 that are arranged about a central axis 3916, such as described above with respect to FIG. 25. Further, FIGS. 39A and 39B show an x-ray beam 3906 being emitted from one of the plurality of x-ray sources 3904, although multiple sources may be activated simultaneously, such as mentioned above. The plurality of x-ray sources 3904 are switched between a high energy state shown in transaxial view 3901 of FIG. 39A and a low energy state shown in transaxial view 3911 shown in FIG. 39B. In some examples, all of the plurality of x-ray sources 3904 may be adjusted between the high energy state and the low energy state at the same time, such as the example shown in FIGS. 39A and 39B. For example, each of the plurality of x-ray sources 3904 may be coupled to a voltage switcher and a dynamic resonance energy recovery generator, such as the voltage switcher 137 and the generator array 139 of FIG. 1. In other examples, a first portion of the plurality of x-ray sources 3904 may be operated with a fixed voltage while a second portion of the plurality of x-ray sources 3904 may be undergo voltage switching.

In addition to or as an alternative to including different energy x-ray sources and/or filtration, a stationary CT imaging system may include a plurality of different x-ray detector types or modules. The selection and orientation of the different source and detector segments (detector type, detector width and coverage, detector resolution, source width, source resolution, etc.) may be optimized based on an anatomy to be imaged. For example, the combinations can be adjusted based on typical motion patterns (chest wall movement, head movement), an amount of power used in the imaging (e.g., more power used laterally due to longer path lengths), and a radiation dose used in the imaging (e.g., lower power desired anterior to avoid breast, eyes and thyroid). Further, the precise spacing and positioning of focal spots and detector cells can be designed such that conjugate rays are interlaced to increase a sampling density.

Figure 40:
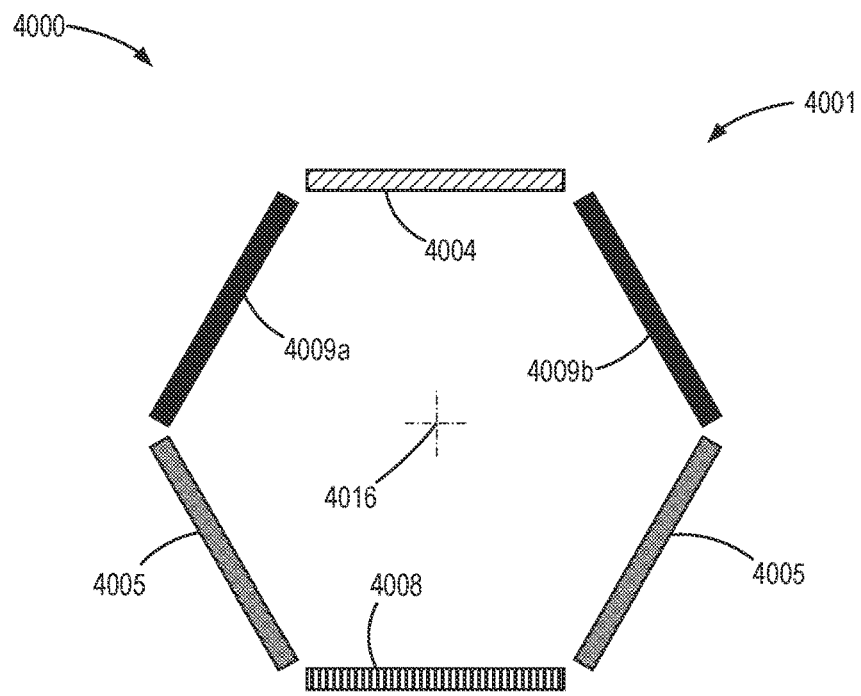
FIG. 40 schematically shows a first exemplary distributed x-ray source and detector configuration for an imaging unit that includes multiple different detector types, according to an embodiment.
Figure 41:
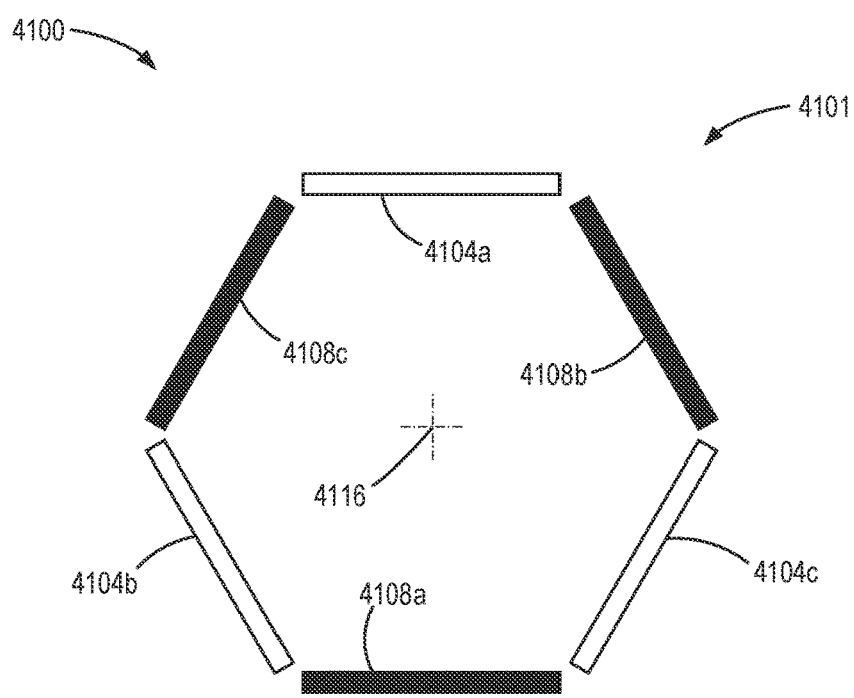
FIG. 41 schematically shows a second exemplary multi-detector type distributed x-ray source and detector configuration for an imaging unit that includes multiple different detector types, according to an embodiment.

As such, FIGS. 40-41 show exemplary embodiments of an x-ray source and x-ray detector configuration that utilize different x-ray detector types, either by including separate detector types in a single configuration (e.g., FIG. 40) or by including hybrid detectors that combine different detector modules (e.g., FIG. 41). Each of the configurations shown in FIGS. 40-41 may be utilized in a stationary CT imaging system (e.g., imaging system 100 of FIG. 1). Letters (e.g., "a," "b," and the like) designate multiples of a functionally equivalent component, when included. Further, it may be understood that each x-ray source and x-ray detector configuration may include anti-scatter grids, multiple aperture devices, and/or collimators, examples of which are further described herein, at least in some examples. Additionally, it may be understood that although the x-ray sources and x-ray detectors are schematically shown as continuous surfaces, it may be understood that distinct focal spots and detector cells may be distributed across the surfaces.

Turning now to FIG. 40, a first exemplary embodiment of a multi-detector type x-ray source and detector configuration 4000 is shown in a transaxial view 4001. The x-ray source and detector configuration 4000 includes a central axis 4016 surrounded by three x-ray sources and three x-ray detectors. In particular, the multi-detector type x-ray source and detector configuration 4000 includes a high resolution distributed x-ray source 4004, two low resolution x-ray sources 4005a and 4005b, a high resolution x-ray detector 4008, and two low resolution x-ray detectors 4009a and 4009b. Each x-ray source may be one example of the distributed x-ray source unit 104 shown in FIG. 1, and each x-ray detector may be one example of the detector array of FIG. 1. "Resolution" refers to how far apart two structures must be before they are observed as separate structures in the resulting image (e.g., spatial resolution). The two structures may be closer together while still being observed as two structures in the resulting image in high resolution compared with low resolution. The high resolution distributed x-ray source 4004, the low resolution x-ray sources 4005a and 4005b, the high resolution x-ray detector 4008, and the low resolution x-ray detectors 4009a and 4009b are all rotationally fixed with respect to the central axis 4016 and have a geometry similar to that described above with respect to FIGS. 29 and 35.

The high resolution distributed x-ray source 4004 is positioned directly opposite to the high resolution x-ray detector 4008 so that the high resolution x-ray detector 4008 is positioned to detect x-rays emitted by the high resolution distributed x-ray source 4004. Similarly, the low resolution distributed x-ray source 4005a is positioned directly opposite to the low resolution x-ray detector 4009a, and the low resolution distributed x-ray source 4005b is positioned directly opposite to the low resolution x-ray detector 4009b. In this way, the resolution of each x-ray detector is positioned to detect x-rays from a source having a matched resolution. Further, the low resolution x-ray sources 4005a and 4005b and the low resolution x-ray detectors 4009a and 4009b may comprise larger coverage or wider segments and the high resolution distributed x-ray source 4004 and the high resolution x-ray detector 4008 may comprise narrower or smaller coverage segments. For example, the high resolution distributed x-ray source 4004 may have smaller focal spots (e.g., 0.7 mm focal spots) compared with the low resolution x-ray sources 4005a and 4005b (e.g., 1.2 mm focal spots). The smaller focal spots provide good spatial resolution, while the larger focal spots of the low resolution x-ray sources 4005a and 4005b provide an increased signal-to-noise ratio compared with the smaller focal spots of the high resolution distributed x-ray source 4004. Similarly, the high resolution x-ray detector 4008 may include smaller detector cells with larger gaps (e.g., partitions) in between compared with the low resolution x-ray detectors 4009a and 4009b. In some examples, the high resolution x-ray detector 4008 is a photon counting detector module, while the low resolution x-ray detectors 4009a and 4009b are each a scintillator-based detector module, such as discussed above with respect to FIG. 1 and elaborated below with respect to FIG. 41.

As such, the multi-detector type x-ray source and detector configuration 4000 includes lower resolution and higher resolution segments to vary an image quality produced during imaging. For example, the high resolution x-ray detector 4008 paired with the high resolution distributed x-ray source 4004 may have increased resolution but a reduced overall detection efficiency compared with the low resolution x-ray detectors 4009a and 4009b due to the larger gaps between the smaller detector cells. Conversely, the low resolution x-ray detectors 4009a and 4009b paired with the low resolution x-ray sources 4005a and 4005b may produce images with a lower resolution but a higher detection efficiency due to the smaller gaps between detector cells. In some examples, the higher resolution images and lower resolution images may be combined using a deep learning network to produce an overall composite diagnostic image with an increased signal-to-noise ratio (from the lower resolution images generated from measurements of beams produced by the low resolution x-ray sources 4005a and 4005b by the low resolution x-ray detectors 4009a and 4009b) and an increased spatial resolution (from the higher resolution images generated from measurements of beams produced by the high resolution distributed x-ray source 4004 by the high resolution x-ray detector 4008), such as according to the methods of FIGS. 53 and 55.

However, instead of having dedicated x-ray source and detector segments for high resolution and low resolution imaging, higher resolution and lower resolution components may be distributed throughout the x-ray source and detector segments. Continuing to FIG. 41, a second exemplary embodiment of a multi-detector type x-ray source and detector configuration 4100 is shown in a transaxial view 4101. The x-ray source and detector configuration 4100 includes a central axis 4116 surrounded by three distributed x-ray sources 4104a 4104b, and 4104c and three x-ray detectors 4108a, 4108b, and 4108c. Each distributed x-ray source 4104a, 4104b, and 4104c may be one example of the distributed x-ray source unit 104 shown in FIG. 1, and each x-ray detector 4108a, 4108b, and 4108c may be one example of the detector array of FIG. 1. The distributed x-ray sources 4104a, 4104b, and 4104c and the x-ray detectors 4108a, 4108b, and 4108c are rotationally fixed with respect to the central axis 4116 and have a geometry similar to that described above with respect to FIGS. 29 and 35.

In the multi-detector type x-ray source and detector configuration 4100, each distributed x-ray source 4104a, 4104b, and 4104c comprises alternating smaller (higher resolution) and larger (lower resolution) focal spots, and each x-ray detector 4108a, 4108b, and 4108c comprises alternating scintillator-based detector modules (or cells) and photon counting (or direct conversion) modules (or cells). The photon counting modules are energy-resolving x-ray detectors that count the number of incoming photons and directly measure photon energy. The scintillator-based detector modules are energy-integrating detectors that convert x-rays into visible light and then then measure the amount of incident light. The two detector types may have a different spatial resolution, sensitivity, and/or signal-to-noise ratio. For example, the photon counting modules may have an increased spatial resolution compared with the scintillator-based detector modules. As such, measurements from the photon counting modules may produce higher resolution images, particularly when measuring beams produced by the smaller focal spots, and measurements from the scintillator-based detector modules may produce lower resolution, lower noise images, particularly when measuring beams produced by the larger focal spots. The higher and lower resolution images may be combined using a deep learning network, such as mentioned above with respect to FIG. 40. As such, the multi-detector type x-ray source and detector configuration 4100 may have high flexibility for the quality of images produced.

In conventional x-ray and non-stationary CT imaging systems, primary x-rays are produced from a single focal point, transmitted through an imaging subject (e.g., a patient), and detected by a detector. In contrast, scattered radiation is secondary radiation produced by the deflection of x-rays by the imaging subject. In such systems, it is effective to use an anti-scatter grid or post-patient collimator to reject x-rays that have a different incidence angle than the primary x-rays, thereby rejecting scattered radiation. However, all of the above x-ray source and detector configurations described with respect to FIGS. 25-41 include distributed x-ray sources and/or multiple x-ray sources, and each detector cell is positioned to detect primary x-rays originating from multiple x-ray focal spots. Hence, the primary x-rays may have a wide range of incidence angles, making it difficult to use traditional stationary anti-scatter grids or collimators. Further, as the amount of tissue or other substance that is being penetrated by the primary beam(s) increases, the greater the incidence of scattered radiation. Therefore, approaches that mitigate scattered radiation (e.g., prevent, reject, and/or correct for the scattered radiation) in stationary CT imaging systems are desired.

As such, FIGS. 42A-50 show exemplary embodiments of x-ray source and x-ray detector configurations that may be utilized in an imaging unit of a stationary CT imaging system (e.g., the imaging unit 123 of the imaging system 100 of FIG. 1). Letters (e.g., "a," "b," and the like) designate multiples of a functionally equivalent component, when included. Additionally, it may be understood that although x-ray detectors are schematically shown as continuous surfaces, it may be understood that distinct detector cells may be distributed in arrays across the surfaces, such as coupled to one or more substrates. Further, it may be understood that the following embodiments may be combined with various filters and/or post-patient collimators or anti-scatter grids, examples of which are described herein.

Figure 42A:
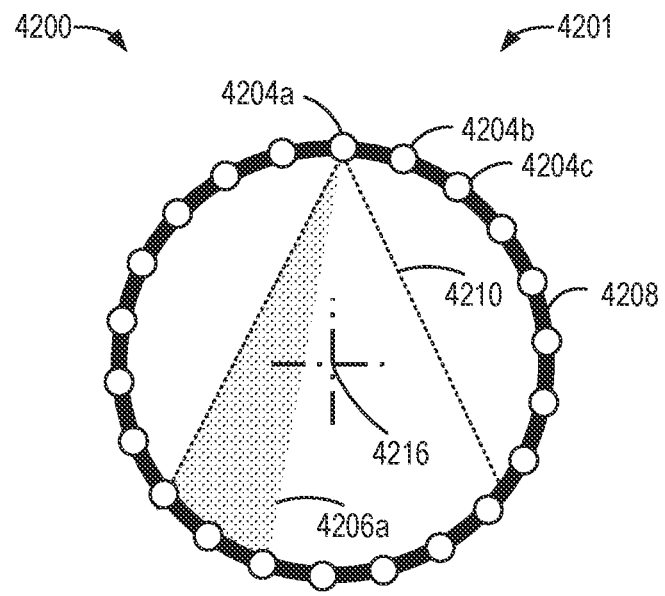
FIGS. 42A and 42B schematically show x-ray beam truncation for an imaging unit, according to an embodiment.
Figure 42B:
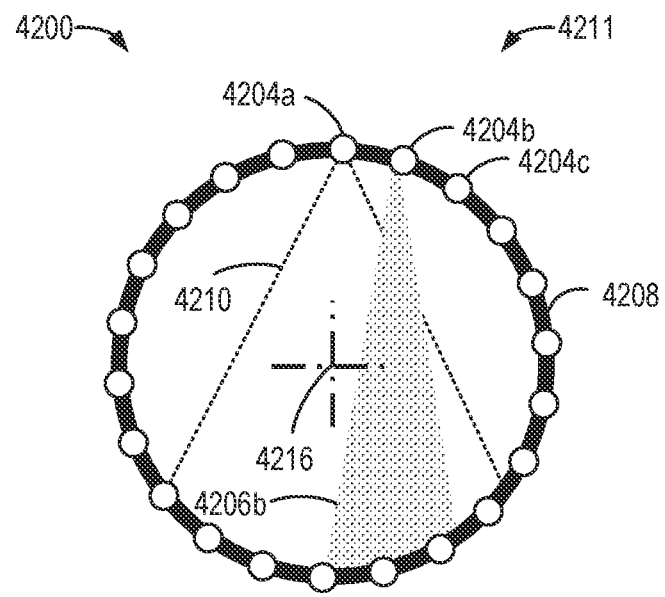
Figure 43:
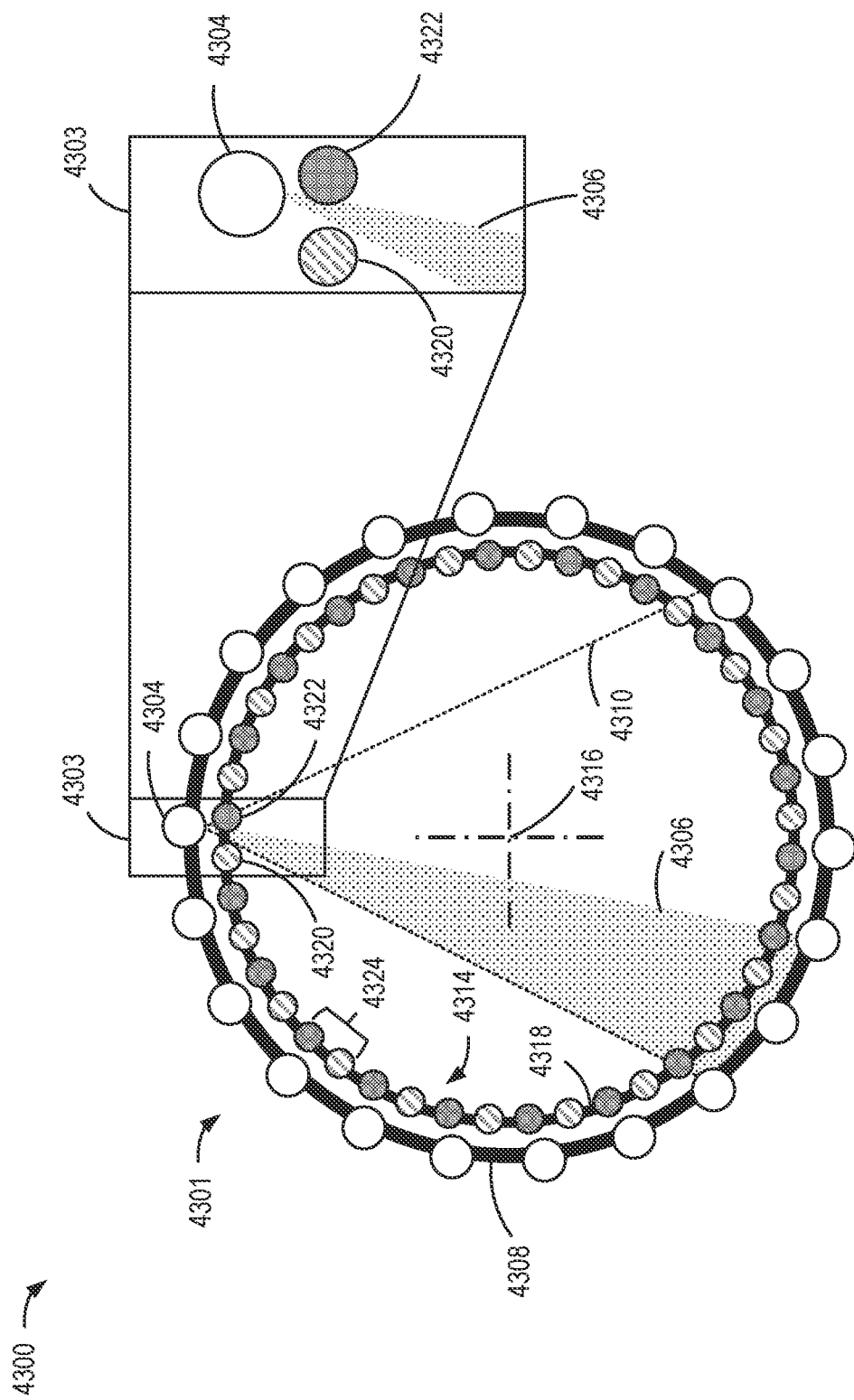
FIG. 43 schematically shows an x-ray source and detector configuration for an imaging unit that includes a first exemplary pre-patient collimator, according to an embodiment.

In one approach, a solid angle of an incident x-ray beam may be reduced to reduce a scatter-to-primary ratio. The scatter-to-primary ratio refers to an energy of scattered radiation divided by an energy of primary x-ray beam energy striking a same location on a detector. Turning to FIGS. 42A and 42B, x-ray beam truncation is schematically shown in an exemplary embodiment of a distributed x-ray source and detector configuration 4200. The distributed x-ray source and detector configuration 4200 includes a plurality of focal spots of a distributed x-ray source (e.g., the distributed x-ray source unit 104) and detector cells arranged about a central axis 4216. In the example shown, only three of the focal spots—a first focal spot 4204*a*, a second focal spot 4204*b*, and a third focal spot 4204*c*—are labeled for illustrative clarity, and the detector cells are represented schematically by a detector array 4208, which may be the detector array 147 of FIG. 1, for example.

FIG. 42A shows a first transaxial view 4201, where the first focal spot 4204*a* is emitting a partial fan beam 4206*a*. A range of a full fan beam 4210 is shown for comparison by dashed lines. FIG. 42B shows a second transaxial view 4211, where the second focal spot 4204*b* is emitting a partial fan beam 4206*b*. Because scattered radiation is proportional to a portion of the imaging subject being irradiated at a given moment, by truncating the x-ray beam, such as by using only the partial fan beam 4206*a* in FIG. 42A and the partial fan beam 4206*b* in FIG. 42B, the scatter-to-primary ratio may be reduced. For example, different focal spots can be collimated in different ways, such that the combination of all of the partial fan beams still provides relatively complete data. For example, the first focal spot 4204*a* may be collimated to emit a relative angular range of −30 to −10 degrees, the second focal spot 4204*b* may be collimated to emit a relative angular range of −10 to +10 degrees, and the third focal spot 4204*c* may be collimated to emit a relative angular range of +10 to +30 degrees. Further, by reducing the angular range emitted from each focal spot relative to the full fan beam 4210, the focal spots may have a larger thermal length and still preserve a small optical focal spot size.

In some examples, the collimation for each focal spot may be adjustable. Continuing to FIG. 43, an exemplary embodiment of a distributed x-ray source and detector configuration 4300 including an adjustable collimator 4314 is shown in a transaxial view 4301. The distributed x-ray source and detector configuration 4300 includes a plurality of focal spots 4304, a detector array 4308, and the adjustable collimator 4314 arranged about a central axis 4316. The adjustable collimator 4314 is a pre-patient (e.g., imaging subject) collimator and includes a plurality of collimator portions 4320 and 4322 arranged in pairs 4324 with respect to each focal spot 4304 and distributed on an actuator 4318 about the central axis 4316. An inset box 4303 particularly shows one pair 4324 of collimator portions 4320 and 4322 with respect to one focal spot 4304. For example, the collimator portions 4320 may shape (e.g., narrow) an x-ray beam 4306 emitted from the corresponding focal spot 4304 in a first direction, and the collimator portions 4322 may shape the x-ray beam 4306 emitted from the corresponding focal spot 4304 in a second direction, different than the first direction. For example, the second direction may be opposite to the first direction. For example, the first direction may be to the right side of the imaging subject, while the second direction is to the left side of the imaging subject. The collimator portions 4320 and 4322 may each be comprised of an x-ray absorbing material, such as lead or tungsten. Further, the adjustable collimator 4314 is positioned to block a portion of the x-ray beam 4306 emitted from each focal spot 4304 before passing through the imaging subject, unlike post-patient, pre-detector collimators, which may block or reduce scatter radiation detection at the detector array 4308.

The actuator 4318 may rotate with respect to the central axis 4316 to move each pair 4324 with respect to the corresponding focal spot 4304 in order to adjust a relative angular range of the x-ray beam 4306. In some examples, the actuator 4318 may comprise a first ring-shaped actuator coupled to the collimator portions 4320, and not to the collimator portions 4322, and a second ring-shaped actuator coupled to the collimator portions 4322, and not the collimator portions 4320. An operator may adjust the first ring-shaped actuator to move the collimator portions 4320 relative to the focal spots 4304 and adjust the second ring-shaped actuator to move the collimator portions 4322 relative to the focal spots 4304. In this way, the collimator portions 4320 and the collimator portions 4322 may be separately controlled to adjust the relative angular range of the x-ray beam 4306 emitted from each focal spot 4304. Further, the adjustable collimator 4314 may reduce the relative angular range of the x-ray beam 4306 relative to that of a full x-ray beam 4310 represented by dashed lines, thereby reducing the scatter-to-primary ratio.

As will be elaborated below with respect to FIG. 52, in some examples, narrow x-ray beam measurements may be alternated with wide beam measurements from the same focal spot 4304. Narrow beam projections having less scatter, such as those obtained by measuring x-ray beam 4306, may be subtracted from wide beam projections having more scatter, such as those obtained from measuring full x-ray beam 4310, to obtain an estimate of the scatter from portions outside of the narrow x-ray beam.

Figure 44:
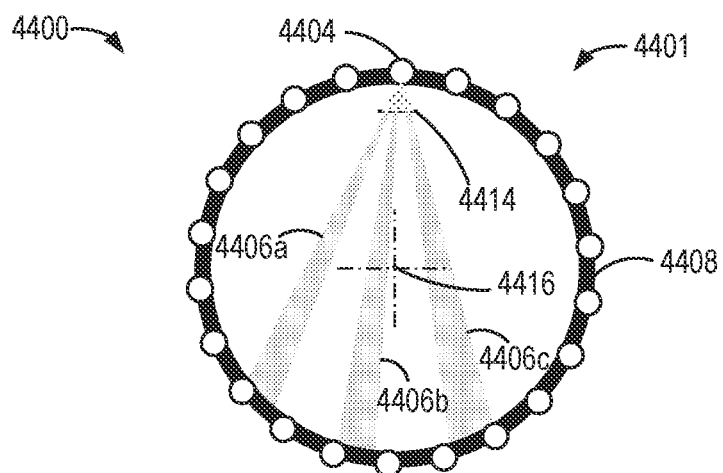
FIG. 44 schematically shows an x-ray source and detector configuration for an imaging unit that includes a second exemplary pre-patient collimator, according to an embodiment.

In a further example, the pre-patient collimator may instead break each x-ray beam into a series of narrow fan beams. Turning now to FIG. 44, an exemplary embodiment of a distributed x-ray source and detector configuration 4400 including a collimator 4414 is shown in a transaxial view 4401. The distributed x-ray source and detector configuration 4400 includes a plurality of focal spots 4404 (only one of which is labeled for illustrative clarity), a detector array 4408, and the collimator 4414 arranged about a central axis 4416. The collimator 4414 is a pre-patient (e.g., imaging subject) collimator that includes a plurality of openings that divide an x-ray beam emitted from one focal spot 4404 into a plurality of narrow fan beams 4406a, 4406b, and 4406c. Although the collimator 4414 is shown with respect to one focal spot 4404, it may be understood that all or some of the focal spots 4404 may include similar collimators. Further, although three narrow fan beams 4406a, 4406b, and 4406c are shown, the collimator 4414 may break the x-ray beam into more or fewer than three narrow fan beams. However, breaking the x-ray beam into a plurality of narrow fan beams may increase penumbra (e.g., a zone of partial intensity x-rays around a central zone of full intensity x-rays), which may affect a dose delivery accuracy.

Figure 45:
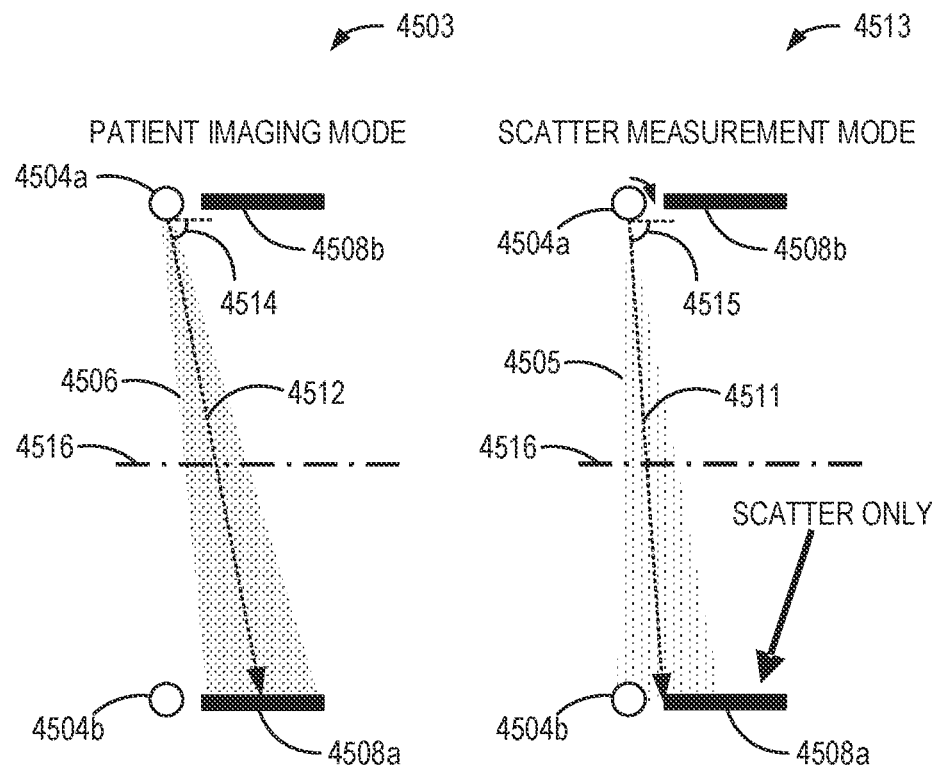
FIG. 45 schematically shows adjusting a fan angle of a focal spot for scatter measurements in an imaging unit, according to an embodiment.

As still another example, a focal spot itself may be moved to change a fan angle or angular range of an x-ray beam. FIG. 45 schematically shows performing scatter measurements while adjusting a fan angle of an x-ray beam emitted from a focal spot of a stationary CT imaging system. FIG. 45 shows a first lateral view 4503 and a second lateral view 4513, which may correspond to different times and operational modes of the stationary CT imaging system. For example, the first lateral view 4503 includes operating the stationary CT imaging system in a patient imaging mode, and the second lateral view 4513 includes operating the stationary CT imaging system in a scatter measurement mode. The lateral views show a first focal spot 4504a, a second focal spot 4504b, a first detector cell 4508a, and a second detector cell 4508b distributed about a central axis 4516. The first focal spot 4504a, the second focal spot 4504b, the first detector cell 4508a, and the second detector cell 4508b may be arranged in any of the x-ray source and detector configurations described with respect to FIGS. 25-36, for example.

While operating in the patient imaging mode shown in first lateral view 4503, the first focal spot 4504a emits a higher energy x-ray beam 4506 that has a beam center (e.g., isocenter) 4512 directed to a central point of the first detector cell 4508a. For example, the beam center 4512 has a first angle 4514 with respect to an axis that is parallel to the central axis 4516 and extends from the focal spot 4504a. Because the beam center 4512 is centered on the first detector cell 4508a, substantially all of the first detector cell 4508a measures primary radiation from the higher energy x-ray beam 4506.

While operating in the scatter measurement mode shown in second lateral view 4513, the first focal spot 4504a emits a lower energy x-ray beam 4505 that has a beam center 4511 directed to an end of the first detector cell 4508a. For example, the beam center 4511 has a second angle 4515 with respect to the axis extending from the focal spot 4504a in the direction of the central axis 4516. The second angle 4515 is greater than the first angle 4514. The first focal spot 4504a is rotated in the second lateral view 4513 compared with the first lateral view 4503 in order to direct the beam center 4511 of the lower energy x-ray beam 4505 at the second angle 4515. Because the beam center 4511 is directed at the edge of the first detector cell 4508a, a portion of the first detector cell 4508a does not measure primary radiation from the lower energy x-ray beam 4505 and may instead measure scatter radiation. The lower energy x-ray beam 4505 may be used during the scatter measurement mode (instead of the higher energy x-ray beam 4506 used in the patient imaging mode) in order to reduce a radiation dose delivered to an imaging subject. Further, only a subset of focal spots, such as the first focal spot 4504a and not the second focal spot 4504b, may be used to perform the scatter measurement in order to further decrease the radiation dose. Note that although FIG. 45 includes an example of moving the focal spot, a collimator may be similarly used to change the fan angle of the x-ray beam in the longitudinal direction along the central axis 4516 between the patient imaging mode and the scatter measurement mode.

As still another example, an imaging unit may additionally or alternatively include post-patient, pre-detector component to attenuate scatter. Turning to FIG. 46, a schematic illustration of a multi-layer aperture device (MAD) 4614 is shown with respect to a detector array 4608, a first focal spot 4604a, a second focal spot 4604b, and a third focal spot 4604c at three different positions. For example, the first focal spot 4604a, the second focal spot 4604b, and the third focal spot 4604c may be included in a distributed x-ray source (e.g., the distributed x-ray source unit 104 of FIG. 1), and the detector array 4608 may be the detector array 147. The MAD 4614 may be the multi-layer aperture device 133 of FIG. 1, for example. The MAD 4614 is comprised of a plurality of layers (e.g., rows) 4614a, 4614b, 4614c, 4614d, and 4614e. Although five layers are shown, in other examples, there may be more or fewer than five layers. Each layer includes a plurality of apertures or openings separated by an x-ray blocking material, such as an x-ray absorbing metal (e.g., lead). The openings of each layer are aligned with each other in an adjustable manner. For example, each layer 4614a, 4614b, 4614c, 4614d, and 4614e translates relative to the other layers to adjust an angle of the openings. Adjusting the alignment of the openings may adjust an incident angle of x-ray radiation that may pass through the MAD 4614.

FIG. 46 shows the MAD 4614 in a first position 4601, a second position 4611, and a third position 4621. For example, the first position 4601 may be a left-slanted position having openings positioned at a first angle (e.g., −30 degrees) relative to an axis extending between a given focal spot and a directly opposite detector cell of the detector array 147, the second position 4611 may be a vertical position having the openings positioned at a second angle (e.g., 0 degrees) relative to the axis, and the third position 4621 may be a right-slanted position having the openings positioned at a third angle (e.g., 30 degrees) relative to the axis. For example, the plurality of layers 4614a, 4614b, 4614c, 4614d, and 4614e may be moved in concert to adjust the incident angle of radiation that is received by the detector array 4608.

For example, a first x-ray beam 4606a emitted from the first focal spot 4604a is aligned with the slant (e.g., angle) of the MAD 4614 while the MAD 4614 is in the first position 4601. As a result, the first x-ray beam 4606a reaches the detector array 4608 and is not blocked by the MAD 4614. In contrast, a second x-ray beam 4606b emitted from the second focal spot 4604b and a third x-ray beam 4606c emitted from the third focal spot 4604c are not aligned with the slant of the MAD 4614 in the first position 4601. As a result, the second x-ray beam 4606b and the third x-ray beam 4606c are both blocked by the MAD 4614, which also blocks scattered radiation 4605. Because the second x-ray beam 4606b, the third x-ray beam 4606c, and the scattered radiation 4605 are blocked by the MAD 4614 in the first position 4601, they are not detected by the detector array 4608.

While the MAD 4614 is in the second position 4611, the second x-ray beam 4606b is aligned with the slant of the MAD 4614, while the first x-ray beam 4606a and the third x-ray beam 4606c are not. As a result, the second x-ray beam 4606b emitted from the second focal spot 4604b reaches the detector array 4608 and is not blocked by the MAD 4614. In contrast, the first x-ray beam 4606a, the third x-ray beam 4606c, and the scattered radiation 4605 are blocked by the MAD 4614 and are not detected by the detector array 4608.

While the MAD 4614 is in the third position 4621, the third x-ray beam 4606c is aligned with the slant of the MAD 4614, while the first x-ray beam 4606a and the second x-ray beam 4606b are not. As a result, the third x-ray beam 4606c emitted from the third focal spot 4604c reaches the detector array 4608 and is not blocked by the MAD 4614. In contrast, the first x-ray beam 4606a, the second x-ray beam 4606b, and the scattered radiation 4605 are blocked by the MAD 4614 and are not detected by the detector array 4608.

Still other approaches may be used for measuring scatter. An exemplary embodiment of a distributed x-ray source and detector configuration 4700 is shown in a transaxial view 4701. The distributed x-ray source and detector configuration 4700 comprises a plurality of focal spots, which may be included in a distributed x-ray source (e.g., the distributed x-ray source unit 104 of FIG. 1), and a detector array 4708 arranged about a central axis 4716. Only one focal spot 4704 is labeled for illustrative clarity. The distributed x-ray source and detector configuration 4700 further comprises a plurality of modulators 4714a, 4714b, and 4714c. The plurality of modulators 4714a, 4714b, and 4714c each comprise a spatially variant x-ray attenuating material and are positioned between the distributed x-ray source and an imaging subject (e.g., the subject 127 of FIG. 1). For example, the x-ray attenuating material may be a semi-transparent blocker that is arranged in the modulator in a known geometric fashion, such as in a grid, a stipe, or a checkerboard pattern, for example. As such, selective portions of an x-ray beam are hardened by passing through the attenuating materials in one of the plurality of modulators 4714a, 4714b, and 4714c, which selectively filter out lower energy photons.

Figure 47:
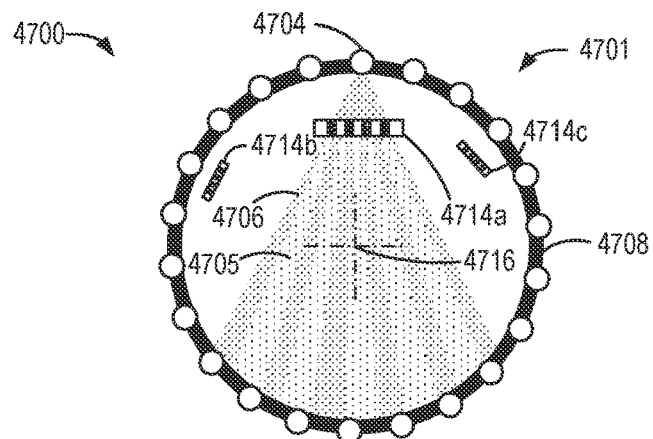
FIG. 47 schematically shows using primary beam modulation for scatter measurements in an x-ray source and detector configuration of an imaging unit, according to an embodiment.
Figure 48:
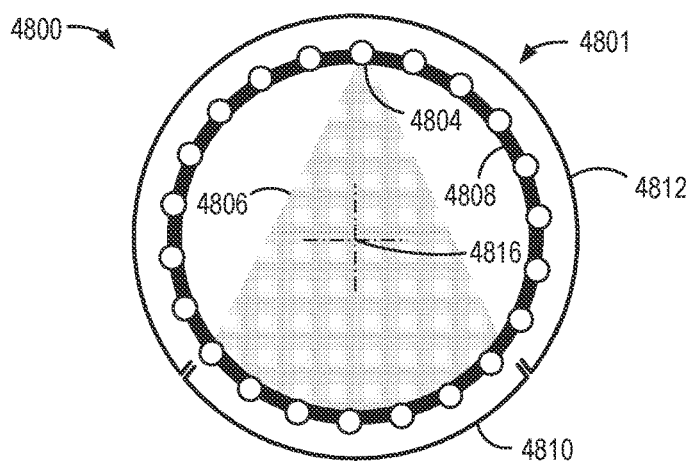
FIG. 48 schematically shows scatter measurements in an x-ray source and detector configuration of an imaging unit, according to an embodiment.

In the example shown in FIG. 47, after passing through the modulator 4714a, an x-ray beam 4706 emitted from the focal spot 4704 has hardened beam portions 4705, only one of which is labeled for illustrative clarity. The hardened beam portions 4705 have an increased average photon energy due to the lower energy photons being filtered out by the attenuating materials, which is detected at distinct detector cells and/or pixel locations of the detector array 4708. This results in a primary radiation detection pattern that is more strongly separated from scatter than when the x-ray beam 4706 does not pass through the modulator 4714a. For example, the scattered radiation may have a lower energy than the hardened beam portions 4705, making it easier to identify scattered radiation from the primary beam signal.

The primary beam signal from the x-ray beam 4706 may be separated from the scatter signal via demodulation principles, for example.

Further, the plurality of modulators 4714a, 4714b, and 4714c may be positioned in front of a portion of the focal spots for an accurate scatter measurement at those focal spots. For other views or primary beams that do no undergo modulation, the scatter may be estimated by interpolation or using the accurate scatter measurements from nearby focal spots. By including modulators in front of a portion of the focal spots, a cost and complexity of the distributed x-ray source and detector configuration 4700 may be decreased.

However, in other examples, scatter measurements may be performed at detector areas that are not receiving primary x-rays. For example, turning to FIG. 48, an exemplary embodiment of a distributed x-ray source and detector configuration 4800 is shown in a transaxial view 4801. The distributed x-ray source and detector configuration 4800 comprises a plurality of focal spots, which may be included in a distributed x-ray source (e.g., the distributed x-ray source unit 104 of FIG. 1), and a detector array 4808 arranged about a central axis 4816. Only one focal spot 4804 is labeled for illustrative clarity. In the example shown in FIG. 48, an x-ray beam 4806 is emitted from the focal spot 4804 and is directed to a first region 4810 of the detector array 4808. Thus, detector cells within the first region 4810 of the detector array 4808 measure the primary radiation of the x-ray beam 4806.

Detector cells within a second region 4812 of the detector array 4808, which is outside of the first region 4810, do not receive the primary radiation of the x-ray beam 4806. For example, the second region 4812 may comprise any portion of the detector array 4808 that is outside of the x-ray beam 4806. Instead, the detector cells within the second region 4812 may detect scattered radiation. Therefore, the detector cells within the second region 4812 may perform scatter measurements, which may be processed with analytic, Monte Carlo, and/or deep learning scatter estimation/correction algorithms. For example, a deep learning scatter estimation algorithm may use both the primary and scatter transmission profiles, a corresponding attenuation profile, and adjacent scatter measurements as inputs and may output an estimated scatter profile. Similarly, a deep learning scatter correction algorithm may use both the primary and scatter transmission profiles, the corresponding attenuation profile, and the adjacent scatter measurements as inputs and may output an estimate of a scatter-corrected primary profile. Such deep learning networks use ground truth data for training. A specialized scatter measurement acquisition protocol (e.g., using smaller cone or fan angles) may be used to reduce scatter when acquiring such data.

Further, because scatter profiles change slowly from one view to the next, regularization can be performed in the view direction, or scatter can be estimated for only a few view angles and interpolated. In addition, those scatter measurements can also be used to perform scatter imaging, such as for reconstructing images representing the (primarily Compton) scatter cross-section in the imaging subject. Similarly, the detector cells in the second region 4812 that are not receiving the (primary) x-ray beam 4806 can be used for fluorescence imaging when photon-counting detectors are used.

However, because the scatter measurements are only measured outside of the x-ray beam 4806, there could be an inaccurate scatter estimation closer to a center of the beam. Therefore, in some examples, x-ray blockers may be used to measure scatter at additional sample points closer to a center of the x-ray beam, and using the additional sample points may increase an accuracy of the estimation or interpolation discussed above.

For example, an exemplary embodiment of a distributed x-ray source and detector configuration 4900 is shown in a transaxial view 4901. The distributed x-ray source and detector configuration 4900 comprises a plurality of focal spots, which may be included in a distributed x-ray source (e.g., the distributed x-ray source unit 104 of FIG. 1), and a detector array 4908 arranged about a central axis 4916. Only one focal spot 4904 is labeled for illustrative clarity. The distributed x-ray source and detector configuration 4900 further comprises x-ray blockers 4914. The x-ray blockers 4914 are positioned between the distributed x-ray source and an imaging subject (e.g., the subject 127 of FIG. 1) and fully block primary x-ray beams. In the example shown in FIG. 49, the x-ray blockers 4914 are arranged in an arc in front of a portion of the focal spots. However, in other examples, the x-ray blockers 4914 may be positioned in front of all of the focal spots. Although five x-ray blockers 4914 are shown, there may be more than five or fewer than five x-ray blockers 4914 in other examples. The x-ray blockers 4914 may be comprised of lead, for example, or another material that absorbs and scatters x-ray radiation without letting it pass through.

Figure 49:
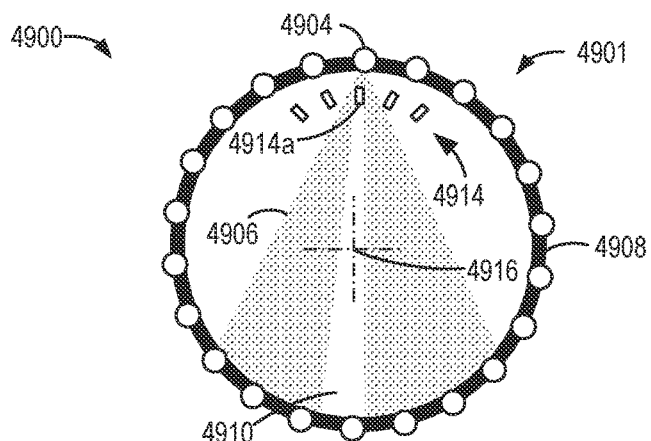
FIG. 49 schematically shows using lead blockers for scatter measurements in an x-ray source and detector configuration of an imaging unit, according to an embodiment.

In the example shown in FIG. 49, an x-ray beam 4906 emitted from the focal spot 4904 contacts one x-ray blocker 4914a of the x-ray blockers 4914. As a result, the x-ray beam 4906 is divided into two portions with a primary beam-free region 4910 positioned there between. Scatter measurements may be obtained in the primary beam-free region 4910 in addition to or as an alternative to acquiring scatter measurements in a region of the detector array 4908 outside of the x-ray beam 4906 (e.g., the second region 4812 described above with respect to FIG. 48). However, the primary beam-free region 4910 produced by the x-ray blocker 4914a results in some missing primary beam measurements, which may be recovered by using deep learning interpolation or iterative reconstruction, an example of which is described herein with respect to FIG. 57.

Because a complexity of a stationary CT imaging system increases with a number of focal spots, it may be desirable to reduce the number of focal spots compared with a traditional CT imaging system. For example, the stationary CT imaging system may have tens or hundreds of focal spots, resulting in sparse view sampling compared to conventional CT imaging (e.g., approximately 1,000 views). Although FIGS. 42A-44 and 49-47 show the focal spots uniformly distributed about a central axis of each x-ray source and detector configuration, in some examples, the view sampling may be non-uniform.

Figure 50:
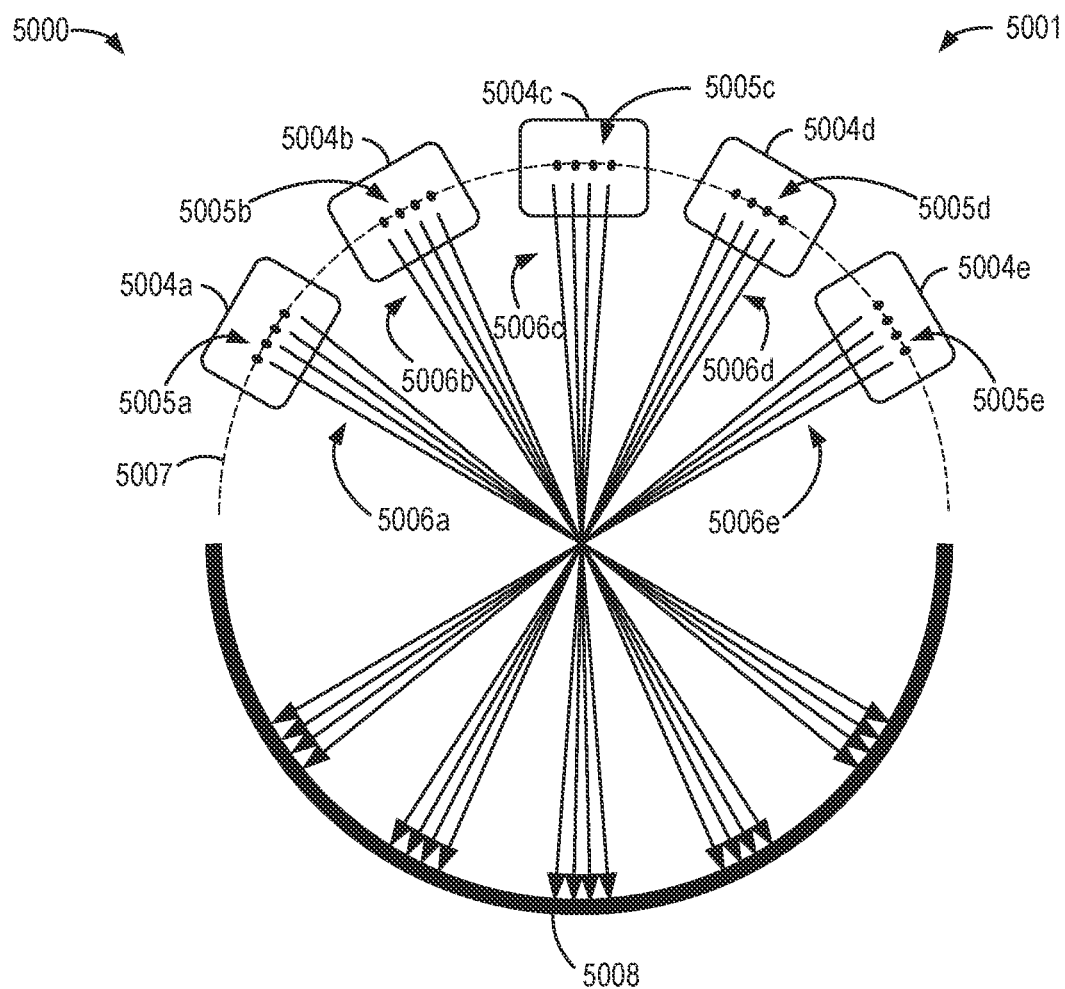
FIG. 50 schematically shows non-uniform view sampling in an imaging unit, according to an embodiment.

Referring to FIG. 50, a transaxial view 5001 schematically shows an exemplary embodiment of an x-ray source and detector configuration 5000 that may be included in an imaging unit of a stationary CT imaging system (e.g., the imaging unit 123 of the imaging system 100 of FIG. 1). The x-ray source and detector configuration 5000 includes an x-ray detector 5008 and a distributed x-ray source 5007. The distributed x-ray source 5007 may be the distributed x-ray source unit 104 of FIG. 1, for example, and the x-ray detector 5008 may be the detector array 147 of FIG. 1. The distributed x-ray source 5007 and the x-ray detector 5008 are shown as each having a semi-circular, arched arrangement, similar to the geometry described with respect to the x-ray source and detector configuration 2600 of FIG. 26. However, in other examples, the distributed x-ray source 5007 and the x-ray detector 5008 may each have a 360 degree range, such as described with respect to the x-ray source and detector configuration 2500 of FIG. 25. The distributed x-ray source 5007 includes plurality of x-ray sources 5004a, 5004b, 5004c, 5004d, and 5004e, and each x-ray source includes a multiple focal spots. For example, each of the x-ray sources 5004a, 5004b, 5004c, 5004d, and 5004e may be a separate x-ray tube. In the example shown in FIG. 50, each x-ray source 5004a, 5004b, 5004c, 5004d, and 5004e includes four focal spots, but the number of focal spots may be greater than four or less than four.

The x-ray source 5004a includes focal spots 5005a that produce views 5006a. For example, each focal spot 5005a produces one of the views 5006a. Similarly, x-ray source 5004b includes focal spots 5005b that produce views 5006b, x-ray source 5004c includes focal spots 5005c that produce a set of views 5006c, x-ray source 5004d includes focal spots 5005d that produce a set of views 5006d, and x-ray source 5004e includes focal spots 5005e that produce a set of views 5006e. As such, the view sampling is locally dense, but sparse overall. For example, the set of views 5006a includes four views that are locally close to each other, but spaced apart from the set of views 5006b.

The focal spot spacing may be optimized for optimal view sampling. For example, opposite views may be interlaced such that the redundancy in conjugate rays is minimized. This may be achieved, for example, by using an odd number of focal spots (or tubes) uniformly spread across 360 degrees. For instance, focal spots may be positioned at 0° and 8° and on the opposite side a focal spot may be positioned at −4°+180°, 4°+180°, and 12°+180°. Optionally, the tube of each x-ray source 5004a, 5004b, 5004c, 5004d, and 5004e may be oriented such that the segments of focal spots in each tube do not line up along the arch of the distributed x-ray source 5007, but can be tilted to be parallel to a longitudinal axis or somewhere in between (oblique). In some examples, the position of the focal spots within each x-ray source 5004a, 5004b, 5004c, 5004d, and 5004e may vary continuously by steering an electron beam and sweeping along the target.

Figure 51:
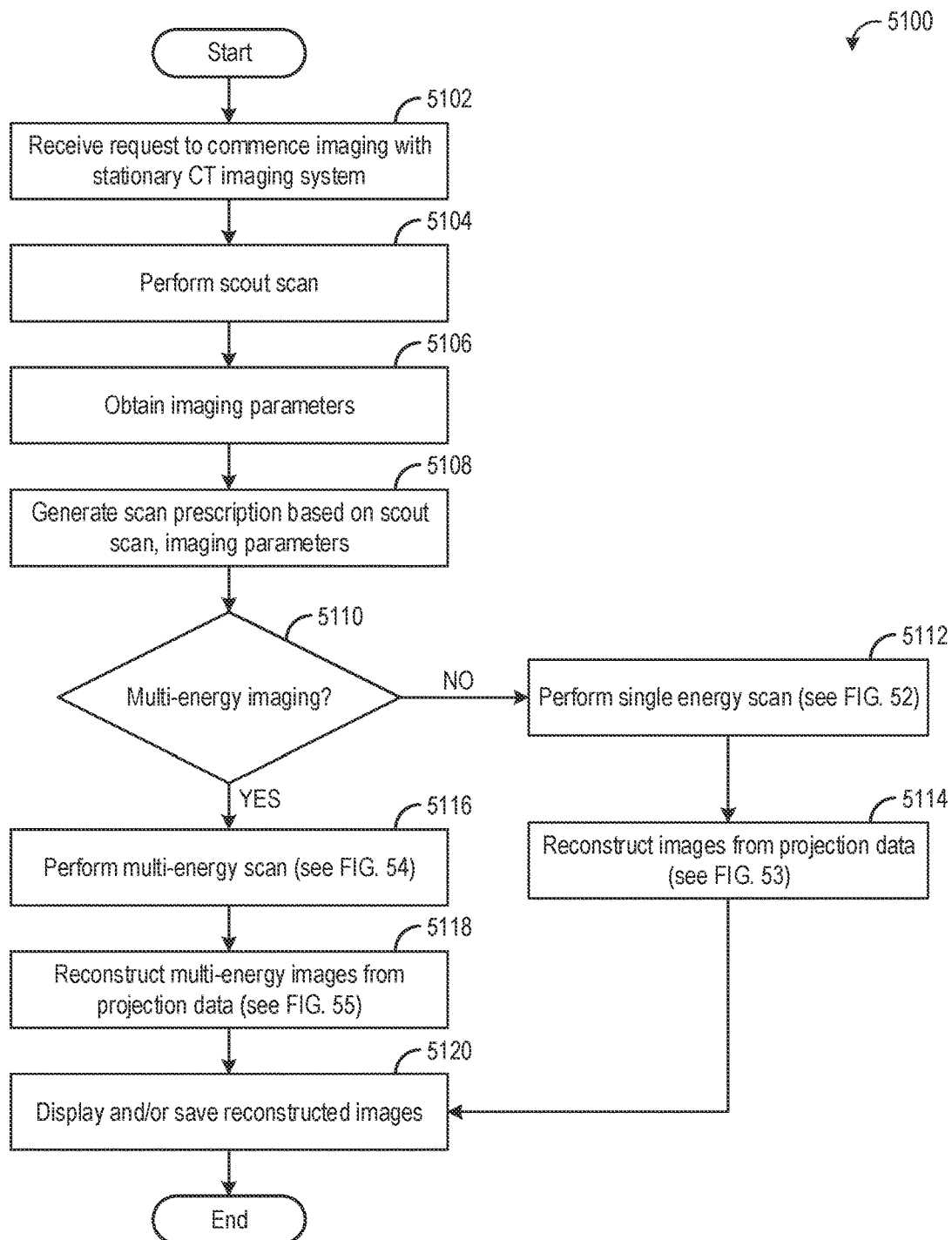
FIG. 51 is a high-level flow chart illustrating a method for performing CT scans using a stationary CT imaging system, according to an embodiment.

FIG. 51 shows a flow chart illustrating a method 5100 for carrying out a CT scan using a stationary CT imaging system, which may be the imaging system 100 shown in FIG. 1. The stationary CT imaging system may include any of the x-ray source and detector configurations described with respect to FIGS. 25-50, for example. The method 5100 and other methods included herein may be carried out according to instructions stored in non-transitory memory of one or more computing devices (e.g., the computing device 116, the image processor unit 151, and/or the x-ray controller 110 of FIG. 1).

At 5102, the method 5100 includes receiving a request to commence imaging with the stationary CT imaging system. For example, an operator may input a command or otherwise indicate to the computing system that a diagnostic scan will be performed. Further, a subject (such as a patient) may be prepared for the diagnostic scan. One or more anatomies of the subject (such as body parts or systems including brain, heart, respiratory system, etc.) may be identified to be a region of interest (ROI) to be scanned. The subject (such as the subject 127 of FIG. 1) may be positioned on a support surface (such as the support surface 135 of FIG. 1). In some examples, a support surface motor controller (e.g., the support surface motor controller 126 of FIG. 1) may move the support surface so that a desired anatomy of the subject is within an imaging field of view. In other examples, an imaging unit of the stationary CT imaging system may be moved with respect to the subject, such as the motor controller 112 of FIG. 1.

At 5104, the method 5100 includes performing a scout scan. The scout scan provides a projection view along a longitudinal axis of the imaging subject and generally provides aggregations including internal structures of the subject. A scout scan may be used to image the ROI of the subject for the subsequent diagnostic scan. The scout scan may be an ultra-low dose CT scan, a tomosynthesis scan, or one or more traditional scout scans.

At 5106, the method 5100 includes obtaining imaging parameters. For example, the operator may input or select the imaging parameters according to a scanning protocol or a menu. The imaging parameters may include setting a scan timing, a starting location, an ending location, etc. As one example, the scan timing may include a start time and a duration for imaging each section. As another example, the imaging parameters may include a total radiation dose to be delivered to the subject, whether multi-energy imaging or single energy imaging is desired, a type of x-ray blocking, modulation, or filtering that will be performed (if any), etc.

At 5108, the method 5100 includes generating a scan prescription based on the scout scan and the imaging parameters. As an example, a series of diagnostic scans may be carried out for a desired anatomy or ROI, and the scan prescription may determine a number of views to obtain at each scan location, an energy for operating each x-ray source and/or emitter, slice thickness, helical pitch (e.g., when the CT system is an upright system as explained above with respect to FIG. 4), etc.

At 5110, the method 5100 includes determining if multi-energy imaging is requested. Multi-energy imaging enables the interrogation of materials that have different attenuation properties at different energies and produces more image types than single energy imaging. For example, multi-energy imaging may produce weighted average images that are similar to single energy spectra, monochromatic (e.g., monoenergetic) images of attenuation at a single photon energy rather than a spectrum, basis material images, and/or electron density maps. As an illustrative example, the multi-energy imaging may enable bone to be removed from vascular scans so that vascular structures and pathologies may be more easily identified.

If multi-energy imaging is not requested, the method 5100 proceeds to 5112 and includes performing a single energy scan, as will be described below with respect to FIG. 52. For example, each x-ray source of the stationary CT imaging system may be operated at a same energy.

At 5114, the method 5100 includes reconstructing imaging from projection data, as will be described below the respect to FIG. 53. For example, x-ray detectors (e.g., of the detector array 147 of FIG. 1) may measure attenuated x-rays emitted by the x-ray sources after they pass through the subject, and an image reconstructor (e.g., the image reconstructor 130 of FIG. 1) may use one or a combination of different reconstruction techniques to correct or compensate for scatter, motion, and/or the sparse views afforded by the stationary CT imaging system.

At 5120, the method 5100 includes displaying and/or saving the reconstructed images. For example, the reconstructed images may be displayed on a display device, such as the display device 132 of FIG. 1, in addition to being saved to a memory (e.g., the mass storage 118 and/or the PACS 124 of FIG. 1). In other examples, the reconstructed images may be saved and accessed at a later time for display. In some examples, the operator may interact with or annotate the reconstructed images, and the annotations may also be saved, such as a separate image file. The method 5100 may then end.

Figure 54:
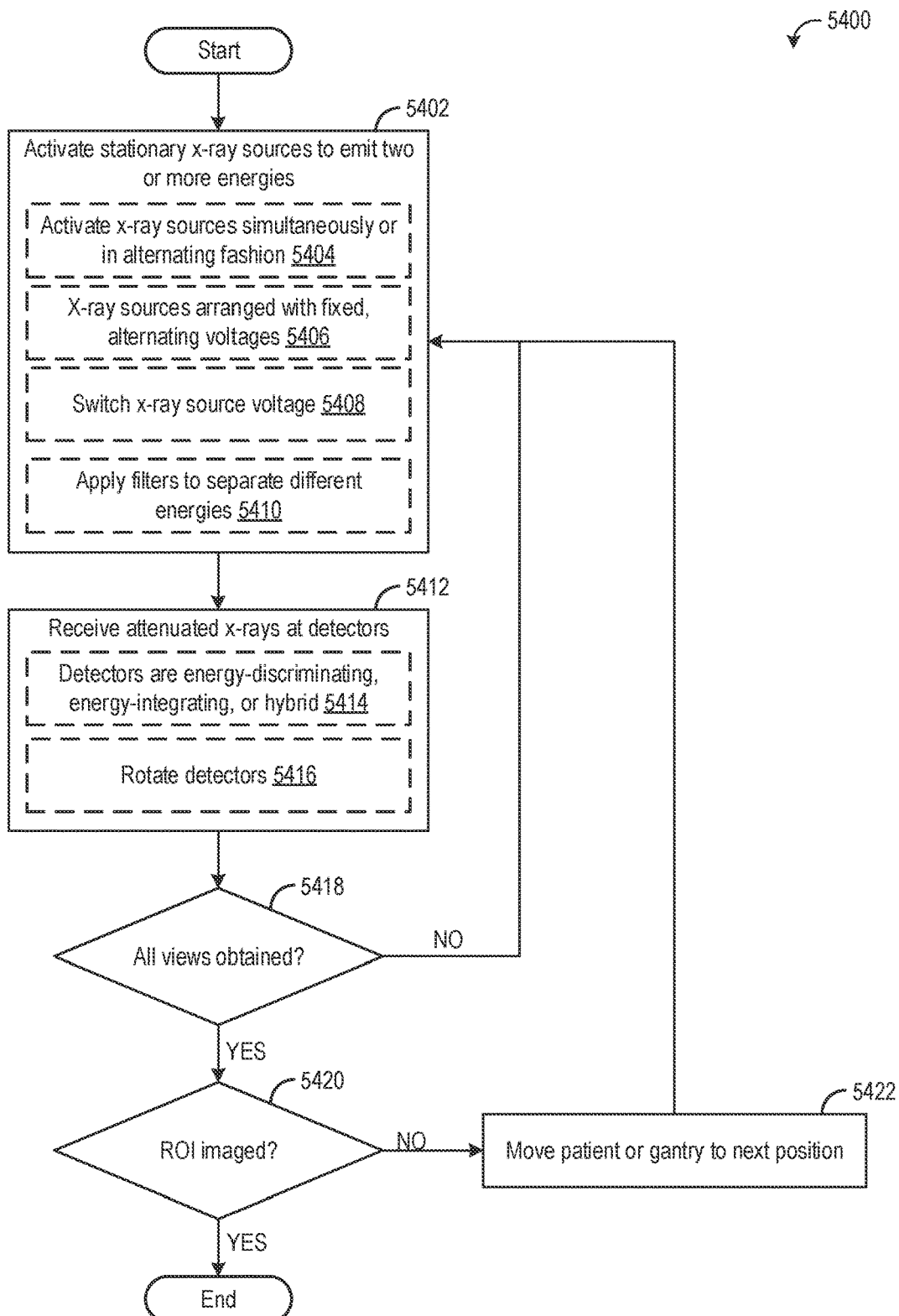
FIG. 54 is a flow chart illustrating a method for performing a multi-energy CT scan using a stationary CT imaging system, according to an embodiment.

Returning to 5110, if multi-energy imaging is requested, the method 5100 proceeds to 5116 and includes performing the multi-energy scan, as will be elaborated with respect to FIG. 54. For example, the x-ray sources may be operated at different energies or may be switched between different energies throughout the scan.

At 5118, the method 5100 includes reconstructing multi-energy images from the projection data, as will be elaborated below with respect to FIG. 55. Similar to the single energy reconstruction, the image reconstructor may use one or a combination of different reconstruction techniques to correct or compensate for scatter, motion, and/or sparse views and may additionally separately reconstruct high energy images and low energy images, at least in some examples. For example, the high energy images and the low energy images may be blended for a final diagnostic image.

Figure 52:
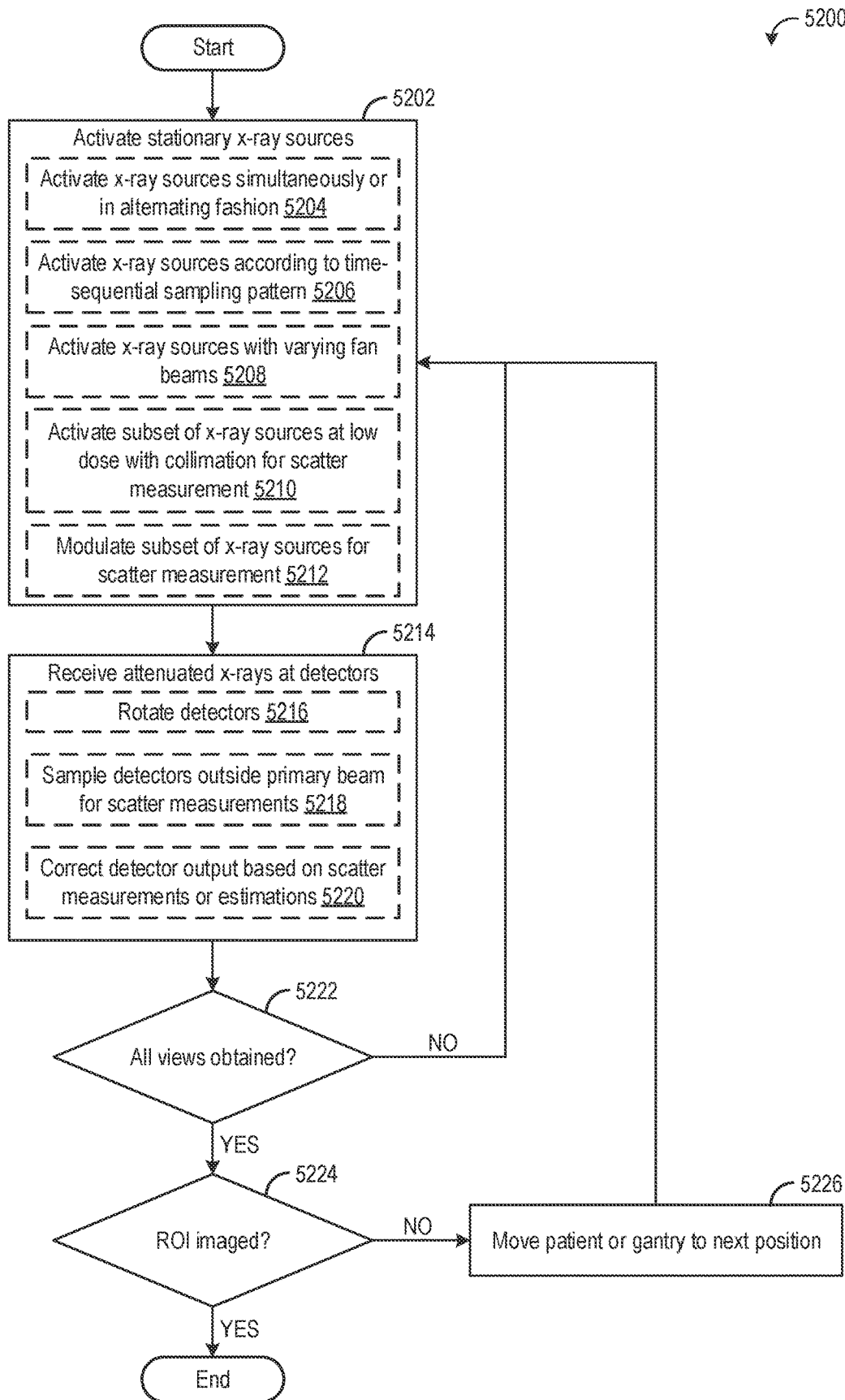
FIG. 52 is a flow chart illustrating a method for performing a single energy CT scan using a stationary CT imaging system, according to an embodiment.

Continuing to FIG. 52, a flow chart of a method 5200 for performing a single energy scan is shown. For example, the method 5200 may be performed as a part of the method 5100 of FIG. 51 (e.g., at 5112).

At 5202, the method 5200 includes activating stationary x-ray sources. The stationary x-ray sources may be included in one or more distributed x-ray source units (e.g., the distributed x-ray source unit 104 of FIG. 1) and may include a plurality of focal spots from which beams of x-ray radiation are emitted. In order to image a relatively large field of view of the subject, the stationary x-ray sources may be arranged in any of the configurations described with respect to FIGS. 25-30, for example.

In some examples, activating the stationary x-ray sources includes activating the x-ray sources simultaneously or in an alternating fashion, as optionally indicated at 5204. By energizing the x-ray sources simultaneously or in an alternating fashion, "virtual rotation" of the x-ray source is achieved to generate a sinogram of x-ray projection data. For example, a first x-ray source (e.g., a first emitter) may be energized at a first time, and a second x-ray source that is adjacent to the first x-ray source may be energized at a second time, after the first time, etc., until all of the x-ray sources have been energized in sequence. As another example, a first portion of the x-ray sources may be energized at the first time, a second portion of the x-ray sources may be energized at the second time, etc. When multiple x-ray sources are activated simultaneously, the x-ray sources that are activated simultaneously may be spaced apart from one another such that x-ray energy from two emitters do not coincide on the same detector elements.

In some examples, activating the stationary x-ray sources additionally or alternatively includes activating the x-ray sources according to a time-sequential sampling pattern, as optionally indicated at 5206. For example, the time-sequential sampling pattern may ensure that there is only one projection acquired at any time instant. As such, the projection data may be acquired in angular (e.g., a sampling range of view angles) and temporal space. For example, the time-sequential sampling pattern may specify the angular position of the view to collect at any given time to maximize the temporal inter-projection interval while reducing or eliminating motion artifacts. In some examples, multiple sources may be activated simultaneously during the time-sequential sampling pattern. For example, a first emitter from each x-ray source unit may activated simultaneously, followed by a second emitter from each x-ray source unit, then a third emitter from each x-ray source, etc. Alternatively, a first set of emitters (e.g., spaced apart by equidistant amounts) may be activated simultaneously, then a second set of emitters (also spaced apart by equidistant amounts) may be activated, etc.

In some examples, activating the stationary x-ray sources additionally or alternatively includes activating the x-ray sources with varying fan beams, as optionally indicated at 5208. For example, different focal spots may emit partial fan beams of different relative angular ranges to provide relatively complete coverage of the field of view, such as described with respect to FIGS. 42A and 42B. As another example, an x-ray beam may be split into a plurality of narrow fan beams through collimation, such as described with respect to FIG. 44. In some examples, narrow fan beam measurements may be alternated with wide beam measurements from the same x-ray source.

In some examples, activating the stationary x-ray sources additionally or alternatively includes activating a subset of the x-ray sources at a low dose with collimation for scatter measurements, as optionally indicated at 5210. As one example, the collimation may be achieved through an adjustable pre-subject collimator, such as described with respect to FIG. 43. The collimation may reduce a fan angle of the x-ray beam emitted by each x-ray source, for example. Further, the fan angle of the x-ray beam may be adjusted so that the x-ray beam is directed to a portion of the detector, enabling a remaining portion of the detector to measure scatter, such as described with respect to FIG. 45.

In some examples, activating the stationary x-ray sources additionally or alternatively includes modulating a subset of the x-ray sources for scatter measurement, as optionally indicated at 5212. For example, a modulator may be positioned in front of one or more of the x-ray sources, and the x-ray beam emitted by the one or more x-ray sources may pass through the modulator. As described with respect to FIG. 47, the modulator may comprise a spatially variant x-ray attenuating material so that low energy photons are selectively filtered out of portions of the x-ray beam in a known geometric pattern.

At 5214, the method 5200 includes receiving attenuated x-rays at detectors. For example, the detectors may include detector cells of a same or varying size and of a same or different detector type, such as described with respect to FIGS. 40 and 41. The detectors may be photon-counting, scintillation-based, or a combination of the two, for example.

In some examples, receiving the attenuated x-rays at the detectors includes rotating the detectors, as optionally indicated at 5216. For example, certain embodiments may include a smaller angular coverage detector array that rotates with respect to the subject and with respect to the stationary x-ray sources, such as described with respect to FIGS. 30 and 36. As such, the detector array may be rotated about a central axis in order to measure different view angles.

In some examples, receiving the attenuated x-rays at the detectors additionally or alternatively includes sampling the detectors outside of the primary beam for scatter measurements, as optionally indicated at 5218. As particularly described with respect to FIG. 45 and FIGS. 48-49, a portion of the detector array that is outside of the primary x-ray beam may be used to detect scattered radiation, and the scatter measurements may be processed with analytic, Monte Carlo, and/or deep learning scatter estimation/correction algorithms.

In some examples, receiving the attenuated x-rays at the detectors additionally or alternatively includes correcting the detector output based on the scatter measurements or estimations, as optionally indicated at 5220. As one example, a deep learning scatter estimation algorithm may use both the primary and scatter transmission profiles, a corresponding attenuation profile, and adjacent scatter measurements as inputs and may output an estimated scatter profile. Similarly, a deep learning scatter correction algorithm may use both the primary and scatter transmission profiles, the corresponding attenuation profile, and the adjacent scatter measurements as inputs and may output an estimate of a scatter-corrected primary profile. Such deep learning networks use ground truth data for training, which may include scatter-corrupted data (e.g., using full fan-beams such that a maximum/typical amount of scatter is present) and scatter-reduced data (e.g., using partial fan-beams so that less scatter is present). The primary and scatter transmission profiles may also be referred to as a total transmission profile, and may be generated from detector output from each detector element of the plurality of detector elements (including detector elements that intercept a primary x-ray beam and detector elements that do not intercept the primary x-ray beam). The attenuation profile may be generated from output from only the subset of detector elements that intercept the primary x-ray beam, and the scatter measurement may be generated from output from only one or more detector elements of the plurality of detector elements outside the primary x-ray beam. Further, because narrow beams produce less scatter, narrow beam projections may be subtracted from wide beam projections having more scatter, such as those obtained from measuring full x-ray beams, to obtain an estimate of the scatter from portions outside of the narrow x-ray beam, such as mentioned above with respect to FIG. 43. Additionally, scatter may be estimated or measured at one view or a subset of views and the scatter estimation may be applied to remaining views via interpolation.

At 5222, the method 5200 includes determining if all views are obtained. For example, each view may refer to x-ray radiation attenuation measurements (e.g., projection data) acquired by a given detector and associated with a given beam of x-ray radiation intercepted by the detector at a given angle. It may be determined that all views are obtained when all of the views in the prescription generated at 5108 of FIG. 51 are obtained. If all of the views are not obtained, the method 5200 returns to 5202 and includes continuing to activate the stationary x-ray sources. In contrast, if all of the views are obtained, the method 5200 proceeds to 5224 and includes determining if the ROI has been imaged. If the ROI has been imaged, the method 5200 ends. If the ROI has not been imaged, the method 5200 proceeds to 5226 and includes moving the patient or gantry (e.g., the imaging unit supporting the x-ray sources and detector arrays) to a next position so that additional views may be obtained at the next position (e.g., by activating the stationary x-ray sources at 5202). In some examples, such as in the upright configuration explained above with respect to FIG. 4, the gantry/imaging unit may be translated vertically with respect to ground (e.g., up or down) along a patient axis (e.g., the longitudinal axis of the patient) during imaging (e.g., while the x-ray sources are activated) at a speed that may be based on the selected helical pitch.

Figure 53:
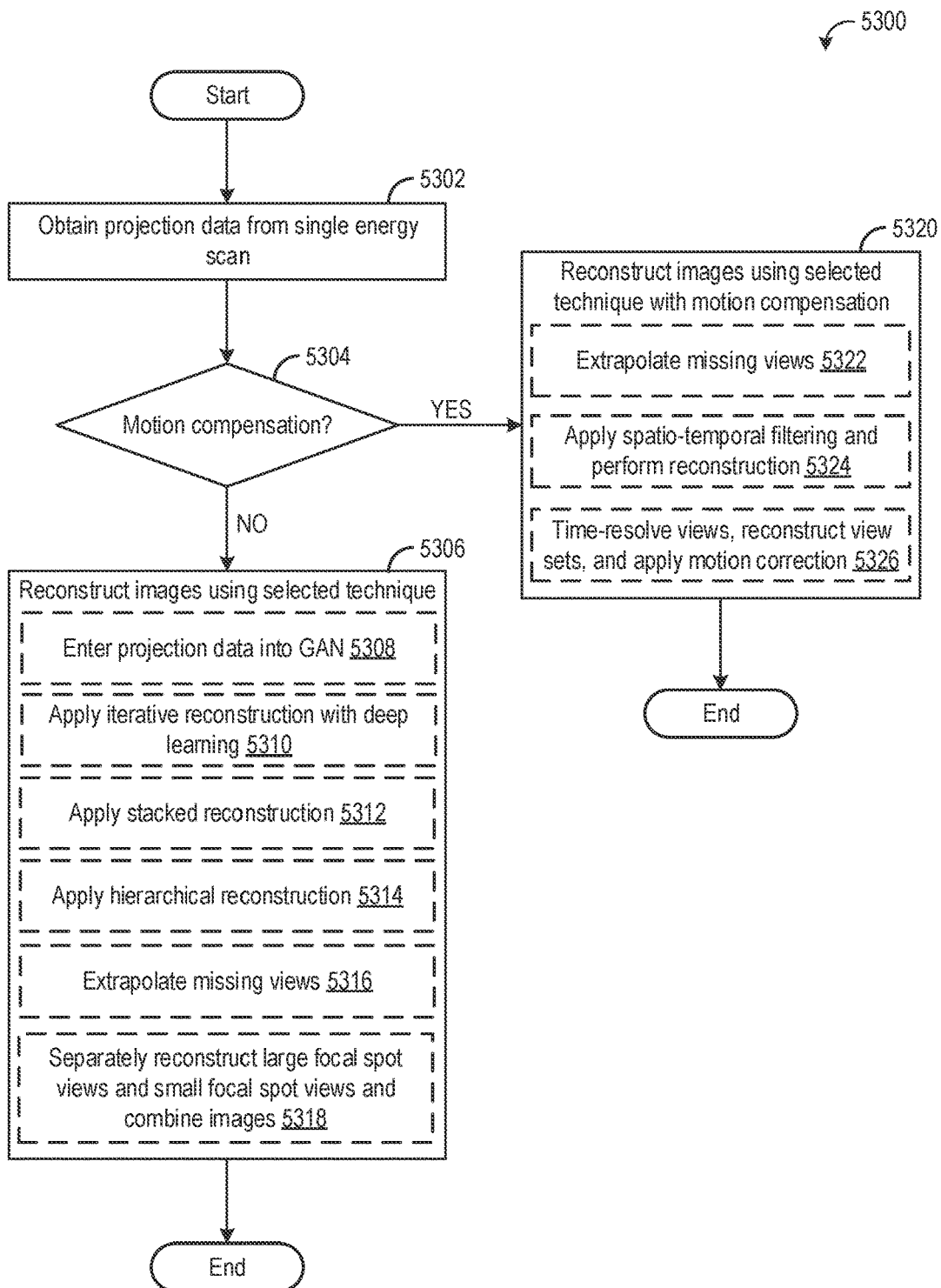
FIG. 53 is a flow chart illustrating a method for reconstructing images from a single energy CT scan performed on a stationary CT imaging system, according to an embodiment.

Next, FIG. 53 shows a flow chart of a method 5300 for reconstructing images based on measurements during a single energy scan. For example, the method 5300 may be performed as a part of the method 5100 of FIG. 51 (e.g., at 5114).

At 5302, the method 5300 includes obtaining projection data from the single energy scan, such as the single energy scan described above with respect to FIG. 52.

At 5304, the method 5300 includes determining if motion compensation is desired. For example, motion artifacts may be introduced through respiratory and cardiac motion during the single energy scan. As one example, motion compensation may be desired during chest imaging.

If motion compensation is not desired, the method 5300 proceeds to 5306 and includes reconstructing the images using a selected technique. In some examples, the selected technique includes entering projection data into a generative adversarial network (GAN), as optionally indicated at 5308. For example, the GAN may be a deep learning network that is used to generate densely sampled sinograms and includes a discriminator that operates in the reconstructed image domain. The discriminator estimates whether the reconstructed image was generated from a real densely-sampled dataset versus from a real sparsely-sampled view dataset. The projection data that is entered into the GAN may be a sparse view projection dataset (e.g., having a reduced number of views than those typically obtained with conventional CT imaging systems, such as 100 views rather than 1000 views). The sparse view projection dataset may be entered as input to the generator of the GAN, which may output a dense-view dataset (e.g., filling in the missing views), where the generator is trained to output the dense-view dataset by the discriminator. The dense-view dataset may be reconstructed to form a reconstructed image using a suitable reconstruction technique such as filtered backprojection.

Figure 56:
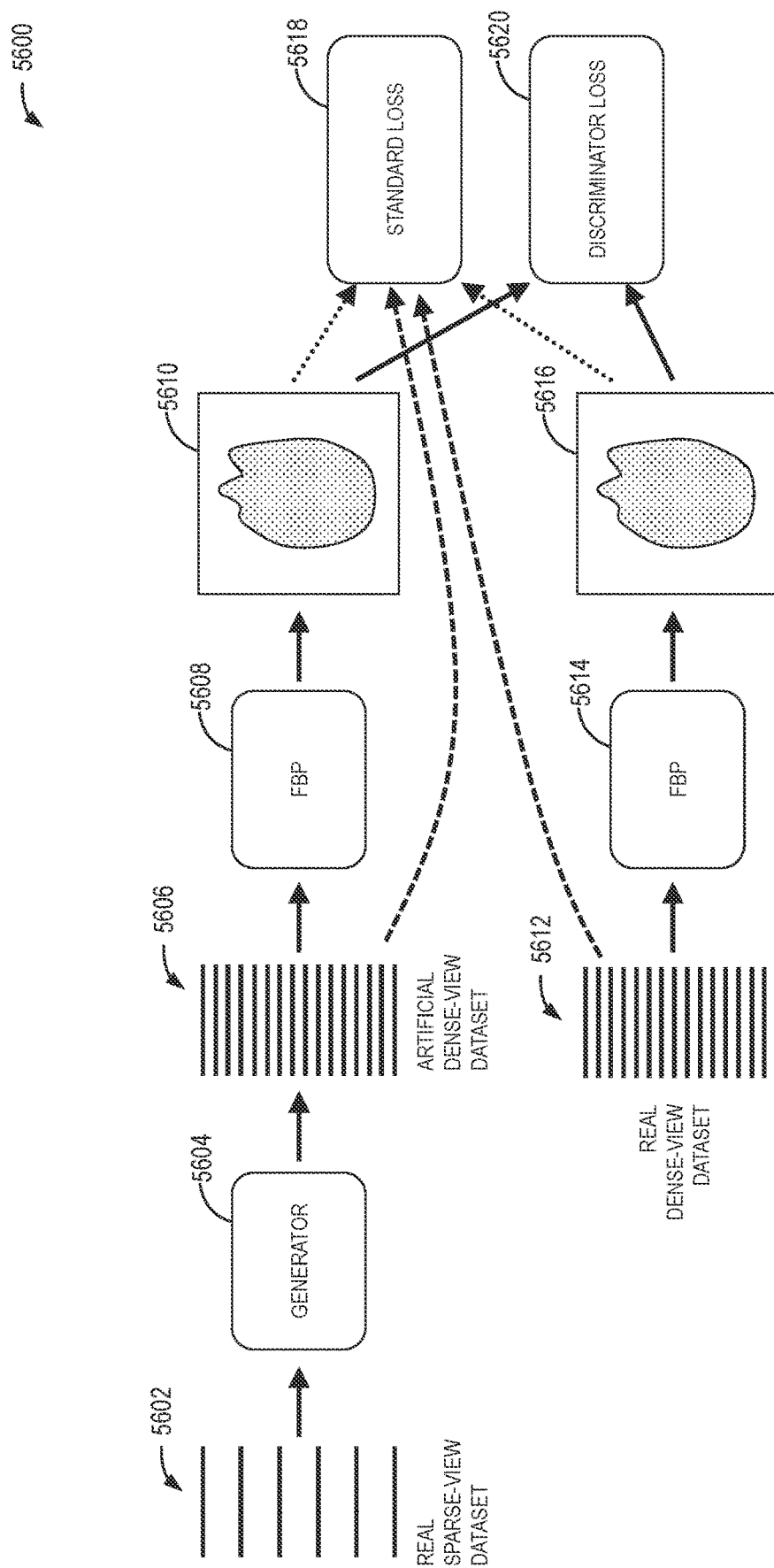
FIG. 56 schematically illustrates a generative adversarial network that may be used in image reconstruction, according to an embodiment.

Turning briefly to FIG. 56, an example GAN 5600 is shown. In the GAN 5600, a real sparse-view dataset 5602 is input into a generator 5604, which generates an artificial (e.g., estimated) dense-view dataset 5606 from the real sparse-view dataset 5602. The artificial dense-view dataset 5606 undergoes a filtered back projection 5608 to produce a first reconstructed image 5610. The generator may be a suitable network, such as a deconvolutional neural network. To train the generator, a reconstructed image produced by the generator (e.g., the first reconstructed image 5610) may be entered into a discriminator along with a second reconstructed image 5616 that is generated from a real dense-view dataset 5612 via a filtered back projection 5614. The discriminator attempts to determine which image is "real" and which image is "fake" (e.g., generated from an artificial sparse view dataset rather than a real dense view dataset). The generator is trained using feedback from the discriminator, as the generator aims to fool the discriminator. Further, in some examples, both the artificial dense-view dataset 5606 and the real dense-view dataset 5612 are input into a standard loss function 5618, as indicated by dashed arrows. The standard loss function 5618 may compare the artificial dense-view dataset 5606 to the real dense-view dataset 5612 and output from the standard loss function may be used to train the generator. In some examples, the standard loss function 5618 may additionally or alternatively compare the corresponding reconstructions, as indicated by dotted arrows. The first reconstructed image 5610 and the second reconstructed image 5616 are also input into a discriminator loss function 5620, as indicated by solid arrows and as described above. While FIG. 56 shows a real sparse view dataset being used to train the generator, it is to be understood that the sparse view dataset(s) used to train the generator may be pseudo sparse view datasets generated from real dense view datasets. For example, a projection dataset obtained by a conventional CT imaging system having a large number of views (e.g., 1000), a large view angle range (e.g., greater than 180 degrees), and a large FOV (e.g., 50 cm) may be modified to generate the pseudo sparse view dataset by discarding views in order to match the view number, view angle range, and FOV of the projection data obtained by the stationary CT imaging system.

Returning to 5306 of FIG. 53, in some examples, the selected technique additionally or alternatively includes applying iterative reconstruction with deep learning, as optionally indicated at 5310. The iterative reconstruction with deep learning may include an unrolled (e.g., unfolded) iterative reconstruction where one or more priors of the iterative reconstruction are learned from one or more deep learning networks. The deep learning may be trained to recover good quality images from sparse-view datasets. Each update stage combines a datafit update step and a deep learning update step (in parallel or in sequence). The deep learning networks are trained such that the final image estimate has good image quality or looks similar to the image produced from a densely sampled dataset.

Figure 57:
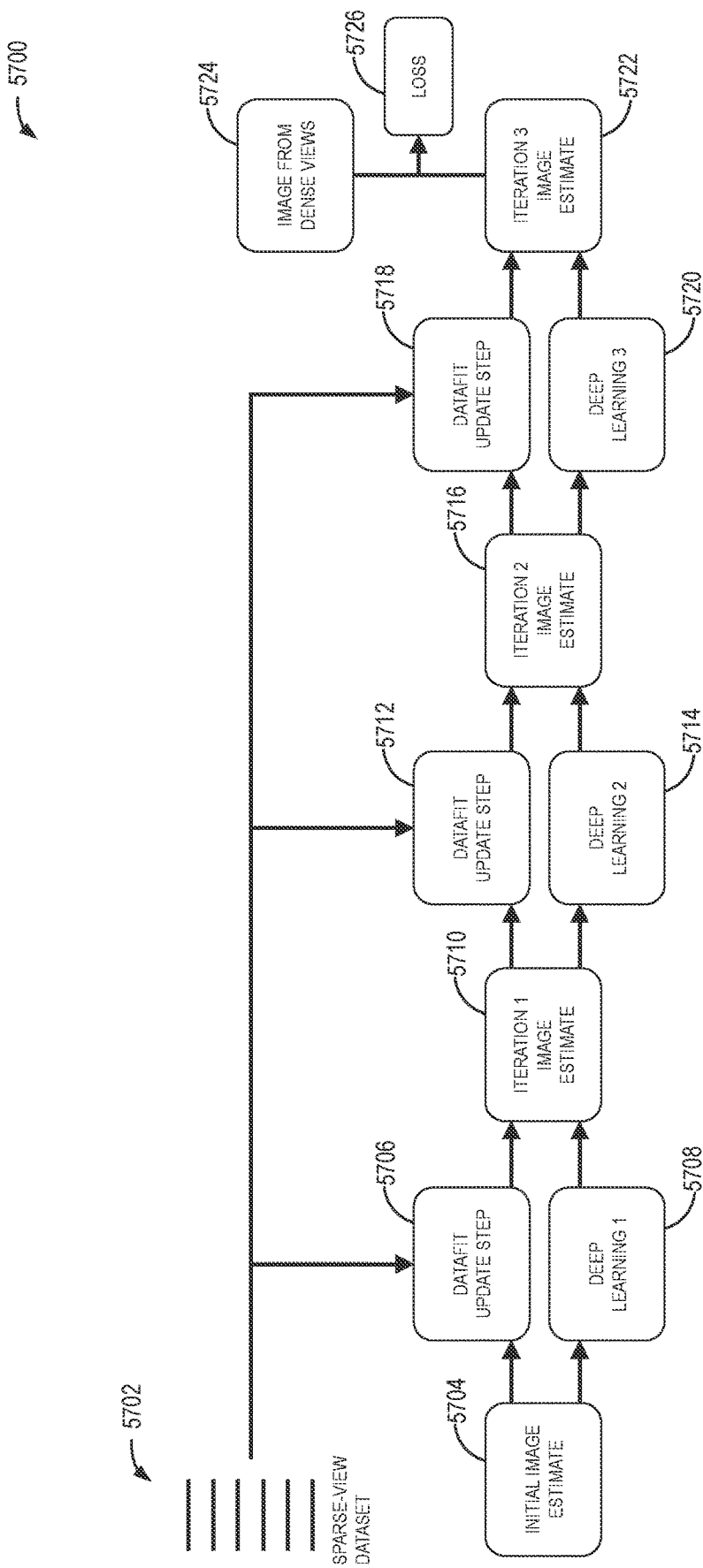
FIG. 57 schematically illustrates an iterative reconstruction approach that may be used for image reconstruction, according to an embodiment.

Turning briefly to FIG. 57, an example unrolled iterative reconstruction network 5700 is shown. In the unrolled iterative reconstruction network 5700, a sparse-view data set 5702 is input into a first datafit update step 5706, which also receives an initial image estimate 5704. The initial image estimate is also received by a first deep learning update step 5708 that is in parallel with the first datafit update step 5706. The output of the first datafit update step 5706 and the output of the first deep learning update step 5708 produce a first image estimate iteration 5710, which is put into each of a second datafit update step 5712 and a second deep learning update step 5714 in parallel. The second datafit update step 5712 also receives the sparse-view data set 5702 and compares the sparse-view data set 5702 to the first image estimate iteration 5710 to determine a measurement error. The output of the second datafit update step 5712 and the output of the second deep learning update step 5714 produce a second image estimate iteration 5716, which is put into each of a third datafit update step 5718 and a third deep learning update step 5720 in parallel. The third datafit update step 5718 also receives the sparse-view data set 5702 and compares the sparse-view data set 5702 to the second image estimate iteration 5716 to determine a measurement error. The output of the third datafit update step 5718 and the output of the third deep learning update step 5720 produce a third image estimate iteration 5722. The third image estimate iteration 5722 is input into a loss function 5726 along with an image from dense views 5724. The measurement error feedback at each datafit update step may help recover structural subtleties in the reconstructed image and suppress inconsistencies and instabilities induced by the deep learning methods used in each deep learning update step.

In some examples, the iterative reconstruction strategy synergizes deep learning, analytic mapping, iterative refinement, and compressed sensing as an analytic, compressive, iterative deep (ACID) network. Reconstructing an image with the ACID network may include entering the sparse view projection dataset into a deep learning network trained to output a first initial reconstructed image, and regularizing the first initial reconstructed image using compressed sensing to generate a second initial reconstructed image. For example, via compressed sensing, the first initial reconstructed image may be transformed to the spatial domain via a Fourier transform and nonzero coefficients may be inferred, which may be used to generate the second initial reconstructed image via an inverse Fourier transform. The sparse view projection dataset may then be updated based on an analytic mapping between the first initial image and the second initial image. The updated sparse view projection dataset may be entered into the deep learning network to generate a third initial reconstructed image, which may be iteratively refined based on the second initial reconstructed image to form a final reconstructed image. In some examples, multiple rounds of updating of the sparse view projection dataset may be performed before the final image is output.

Returning to 5306 of FIG. 53, in some examples, the selected technique additionally or alternatively includes applying a stacked reconstruction, as optionally indicated at 5312. The stacked reconstruction may be performed by back projecting each single view onto a separate image and using these single-view back projections as input to a deep learning network, also referred to as stacked back projection. Optionally, a filter may be applied to each view prior to back projection. In some examples, the reconstruction may be performed using an analytical inverse of a forward transform.

In some examples, the selected technique additionally or alternatively includes applying hierarchical reconstruction, as optionally indicated at 5314. For example, the hierarchical reconstruction approach may be used to reconstruct non-uniformly sampled view datasets. In a first stage(s) of the reconstruction, each set of locally densely sampled views is used to generate a respective single view with partial (weighted) line integrals for each x-ray source. For example, referring to FIG. 50, the set of views 5006*a* may be used to generate a first single view, the set of views 5006*b* may be used to generate a second single view, etc. This first stage is a tomosynthesis-like reconstruction and may be achieved using a deep learning network. The first stage may also use the stacked back projection approach described above. In a second stage, the single views with partial line integrals are used to generate reconstructed images. This second stage is a time-of-flight-like reconstruction and may be achieved using sparse iterative reconstruction or using a deep learning network. The first or second stage may also use the analytic inverse approach described above. In this way, the sparse view projection dataset may be partitioned into a plurality of densely-sampled view sets, each densely-sampled view set may be entered into a network trained to output a respective single view for each densely-sampled view set, and a final image may be reconstructed from all the single views.

In some examples, the selected technique additionally or alternatively includes extrapolating missing views, as optionally indicated at 5316. For example, in some stationary CT imaging system architectures, the available view range is less than a 180 degree (or more) fan angle typically used in CT imaging. For example, the x-ray source may extend over 160 degrees, and the x-ray detector may extend over 200 degrees. In such examples, deep learning may be used to extrapolate the missing views in the view angle direction. Training data may be generated by using complete data and deleting the missing data in the input data. In another example, a deep learning reconstruction approach similar to the ones listed for the sparse view scenarios above may be used. Further, if the final reconstructed image volumes still have better spatial resolution in one direction (e.g., in coronal planes) than in the other direction (e.g., in the sagittal planes), such datasets may be primarily shown to the view as coronal images.

In some examples, the selected technique additionally or alternatively includes separately reconstructing large focal spot views and small focal spot views and combining the images, as optionally indicated at 5318. As described with respect to FIGS. 40 and 41, for example, the large focal spots may provide a better signal-to-noise ratio, and the small focal spots may provide better spatial resolution. The large focal spot views may be reconstructed into a first image having low signal-to-noise, and the small focal spot views may be reconstructed into a second image having high spatial resolution. The resulting low noise and high resolution images may be combined using a deep learning network so that the low noise qualities from the large focal spot views and the high resolution qualities from the small focal spot views are kept in the combined image. The method 5300 may then end.

Returning to 5304, if instead motion compensation is desired, the method 5300 proceeds to 5320 and includes reconstructing the images using a selected technique with motion compensation. In some examples, the selected technique with motion compensation includes extrapolating missing views, as optionally indicated at 5322. For example, a sparse dataset may be acquired in order to reduce the overall scan time, thereby reducing motion, and missing views may be extrapolated, such as described above at 5316.

In some examples, the selected technique with motion compensation additionally or alternatively includes applying spatio-temporal filtering and performing the reconstruction, as optionally indicated at 5324. For example, filtering may be applied in the time direction, such as using a finite impulse response filter, and also in the angular direction, such as using a discrete Fourier transform. The filtered projections may be back-projected to obtain a reconstructed image of the subject.

In some examples, the selected technique with motion compensation additionally or alternatively includes time-resolving views, reconstructing view sets, and applying motion correction, as optionally indicated at 5326. For example, the total set of views may be partitioned into several sparser but more time-resolved subsets of views. The time-resolved subsets may include views taken at the same or close to the same time. As an example, if multiple emitters are activated simultaneously, each view obtained from those emitters activated simultaneously may form a subset of views. Each subset of views may be reconstructed separately using a selected sparse view reconstruction technique, such as described above at 5306. Motion estimation can be performed based on the time-resolved reconstructions. Then, based on the motion estimation, motion correction can be applied to reconstruct the complete set of views into one time-resolved reconstruction or to warp and recombine all subset reconstructions. The method 5300 may then end.

Thus, FIGS. 52 and 53 provide for generating a sparse view projection dataset by activating a plurality of emitters of one or more stationary distributed x-ray source units to emit x-ray beams toward an object within an imaging volume, where the x-ray source unit(s) does not rotate around the imaging volume, and receiving attenuated x-ray beams with one or more detector arrays. As described above, the sparse view projection dataset differs from conventional dense view projection datasets in one or more of a total number of views, a spacing of views, a view angle range, and a field of view. An image may be reconstructed from the sparse view projection dataset using a sparse view reconstruction method that includes a deep learning network. The deep learning network may be trained with training data that includes: a dense view projection dataset and/or one or more training images generated from the dense view projection dataset, and a pseudo sparse view projection dataset generated from the dense view projection dataset and/or one more training images generated from the pseudo sparse view projection dataset. The pseudo sparse view projection dataset may be generated by discarding a plurality of views of the dense view projection dataset so that a total number of views, a spacing of views, a view angle range, and a field of view of the pseudo sparse view dataset matches the total number of views, the spacing of views, the view angle range, and the field of view of the sparse view projection dataset. In this way, the training data that is used to train the deep learning network may match the projection data obtained by the stationary CT system at least in terms of the number and spacing of views, which may enable the trained network to more accurately aid in high-quality image reconstruction using sparse view datasets. As used herein, a deep learning network may refer to a convolutional neural network, an artificial neural network, a recurrent neural network, and/or other suitable multi-layered networks or machine learning algorithms.

Continuing to FIG. 54, a flow chart of a method 5400 for performing a multi-energy scan is shown. For example, the method 5400 may be performed as a part of the method 5100 of FIG. 51 (e.g., at 5116).

At 5402, the method 5400 includes activating stationary x-ray sources (e.g., emitters) to emit two or more energies. In some examples, activating the stationary x-ray sources to emit the two or more energies includes activating the x-ray sources simultaneously or in an alternating fashion, as optionally indicated at 5404.

In some examples, activating the stationary x-ray sources to emit the two or more energies additionally or alternatively includes activating the x-ray sources arranged with fixed, alternating voltages, as optionally indicated at 5406. For example, a first segment or portion of the stationary x-ray sources may be operated at a higher voltage to emit higher energy x-ray beams, and a second segment or portion of the stationary x-ray sources may be operated at a lower voltage to emit lower energy x-ray beams. Examples of such configurations are described with respect to FIGS. 31-37.

In some examples, activating the stationary x-ray sources to emit the two or more energies additionally or alternatively includes switching the x-ray source voltage, as optionally indicated at 5408. For example, as described with respect to FIGS. 1 and 39A-39B, a voltage switcher may adjust the stationary x-ray sources between different energization modes, such as a lower energy mode and a higher energy mode.

In some examples, activating the stationary x-ray sources to emit the two or more energies additionally or alternatively includes applying filters to separate different energies, as optionally indicated at 5410. For example, as described with respect to FIGS. 38A and 38B, a filter may be selectively applied to the x-ray sources emitting a first (e.g., lower) energy x-ray beam and not to the x-ray sources emitting a second (e.g., higher) energy x-ray beams.

Further, it may be understood that collimation, modulation, and varying fan beams may be used when activating the stationary x-ray sources to emit the two or more energies, similar to that described above with respect to FIG. 52.

At 5412, the method 5400 includes receiving attenuated x-rays at detectors, similar to that described above at 5214 of FIG. 52. In some examples, receiving the attenuated x-rays at the detectors includes the detectors being energy-discriminating, energy-integrating, or hybrid detectors, as optionally indicated at 5414. As described with respect to FIGS. 40 and 41, the different detectors may have differing sensitivity or differing spatial resolution, for example. When energy-discriminating detectors are used, all the x-ray sources may be operated at the same peak voltage and different x-ray spectra may be obtained by the different energy-discriminating detectors.

In some examples, receiving the attenuated x-rays at the detectors additionally or alternatively includes rotating the detectors, as optionally indicated at 5416, in the manner described above with respect to 5216 of FIG. 52. Further, it may be understood that scatter measurements or estimations may be performed and used to correct the detector output, such as described with respect to FIG. 52.

At 5418, the method 5400 includes determining if all views are obtained. For example, each view may refer to x-ray radiation attenuation measurements (e.g., projection data) acquired by a given detector and associated with a given beam of x-ray radiation intercepted by the detector at a given angle. It may be determined that all views are obtained when all of the views in the prescription generated at 5108 of FIG. 51 are obtained. If all of the views are not obtained, the method 5400 returns to 5402 and includes continuing to activate the stationary x-ray sources to emit the two or more energies. In contrast, if all of the views are obtained, the method 5400 proceeds to 5420 and includes determining if a ROI has been imaged. If the ROI has been imaged, the method 5400 ends. If the ROI has not been imaged, the method 5400 proceeds to 5422 and includes moving the patient or gantry to a next position so that additional views may be obtained at the next position (e.g., by activating the stationary x-ray sources to emit the two or more energies at 5402), such as mentioned above with respect to FIG. 52.

Figure 55:
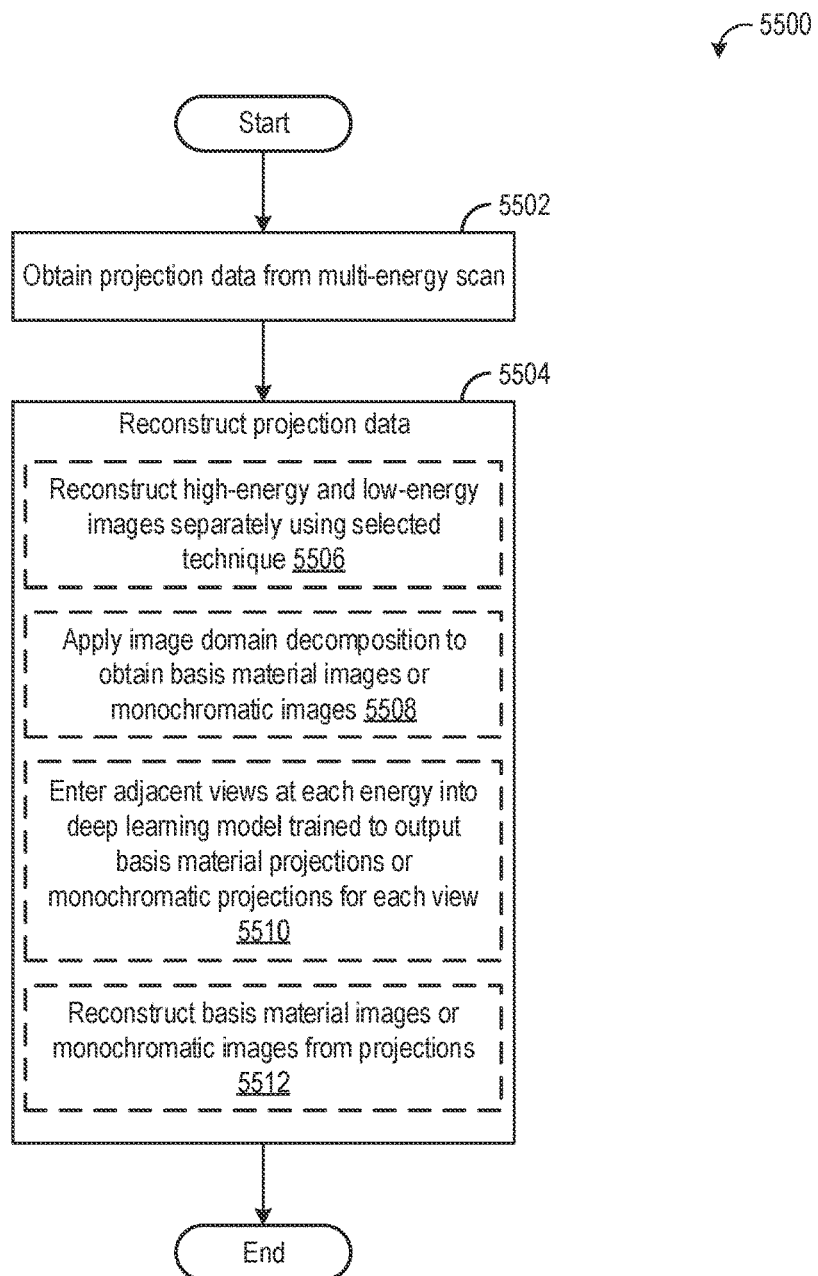
FIG. 55 is a flow chart illustrating a method for reconstructing images from a multi-energy CT scan performed on a stationary CT imaging system, according to an embodiment.

Next, FIG. 55 shows a flow chart of a method 5500 for reconstructing images based on measurements during a single energy scan. For example, the method 5500 may be performed as a part of the method 5100 of FIG. 51 (e.g., at 5118).

At 5502, the method 5500 includes obtaining projection data from the multi-energy scan, such as the multi-energy scan described above with respect to FIG. 54.

At 5504, the method 5500 includes reconstructing the projection data. In some examples, reconstructing the projection data includes reconstructing high-energy and low-energy images separately using a selected technique, as optionally indicated at 5506. Various techniques that may be selected are described with respect to FIG. 53 (at 5306) for reconstructing projection data from single energy scans. In some examples, various sparse view reconstruction techniques may be used.

The separate high-energy and low-energy images may be processed by applying image domain decomposition to obtain basis material images or monochromatic images, as optionally indicated at 5508. In some examples, reconstructing the projection data additionally or alternatively includes entering adjacent views at each energy into a deep learning network/model trained to output basis material projections or monochromatic projections for each view, as optionally indicated at 5510. For example, a first view at a first energy may input into the deep learning model along with a second, adjacent view (or, when fast voltage switching is used, the same view) at a second energy, and the deep learning model may output a joint view (e.g., a joint projection) as a basis material view or monochromatic view. In some examples, reconstructing the projection data additionally or alternatively includes reconstructing basis material images or monochromatic images from the projections, as optionally indicated at 5512. For example, a deep learning network may use a number of adjacent views at high and low energy as input and may output one or more views at specific view angles that represent either basis material projections or monochromatic basis projections. Image-domain decomposition then may be performed to obtain basis materials images or monochromatic images. The method 5500 may then end.

FIGS. 2-7 and 9-21 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, the term "approximately" is construed to mean plus or minus five percent of the range unless otherwise specified.

In one embodiment, a modular imaging system comprises: a plurality of distributed x-ray source units releasably coupled to a plurality of detector arrays, with the plurality of distributed x-ray source units and the plurality of detector arrays forming a self-supporting structure including a central opening shaped to receive a subject to be imaged. In a first example of the modular imaging system, each distributed x-ray source unit of the plurality of distributed x-ray source units is interchangeable with each other distributed x-ray source unit of the plurality of distributed x-ray source units and each detector array of the plurality of detector arrays is interchangeable with each other detector array of the plurality of detector arrays without altering an imaging quality of the modular imaging system. A second example of the modular imaging system optionally includes the first embodiment, and further includes wherein a central axis of the central opening extends parallel with a ground surface on which the self-supporting structure sits. A third example of the modular imaging system optionally includes one or both of the first and second embodiments, and further includes wherein a length from the central axis to each distributed x-ray source unit of the plurality of distributed x-ray source units is equal to a length from the central axis to each detector array of the plurality of detector arrays. A fourth example of the modular imaging system optionally includes one or more or each of the first through third examples, and further includes wherein the plurality of distributed x-ray source units consists of an odd number of distributed x-ray source units and the plurality of detector arrays consists of an odd number of detector arrays. A fifth example of the modular imaging system optionally includes one or more or each of the first through fourth examples, and further includes wherein the plurality of distributed x-ray source units includes exactly three distributed x-ray source units comprising a first distributed x-ray source unit, a second distributed x-ray source unit, and a third distributed x-ray source unit, and the plurality of detector arrays includes exactly three detector arrays comprising a first detector array, a second detector array, and a third detector array. A sixth example of the modular imaging system optionally includes one or more or each of the first through fifth examples, and further includes wherein a first axis extending along a centerline of the first distributed x-ray source unit is parallel with a second axis extending along a centerline of the first detector array, a third axis extending along a centerline of the second distributed x-ray source unit is parallel with fourth axis extending along a centerline of the second detector array, and a fifth axis extending along a centerline of the third distributed x-ray source unit is parallel with a sixth axis extending along a centerline of the third detector array. A seventh example of the modular imaging system optionally includes one or more or each of the first through sixth examples, and further includes wherein each distributed x-ray source unit of the plurality of distributed x-ray source units is arranged between two adjacent detector arrays of the plurality of detector arrays. An eighth example of the modular imaging system optionally includes one or more or each of the first through seventh examples, and further includes wherein each distributed x-ray source unit of the plurality of distributed x-ray source units is arranged in an alternating configuration with each detector array of the plurality of detector arrays. A ninth example of the modular imaging system optionally includes one or more or each of the first through eighth examples, and further includes wherein the self-supporting structure has a hexagonal profile. A tenth example of the modular imaging system optionally includes one or more or each of the first through ninth examples, and further includes wherein a length along a centerline of each distributed x-ray source unit of the plurality of distributed x-ray source units is the same as a length along a centerline of each detector array of the plurality of detector arrays. An eleventh example of the modular imaging system optionally includes one or more or each of the first through tenth examples, and further includes wherein each distributed x-ray source unit of the plurality of distributed x-ray source units is fixedly coupled to an adjacent detector array of the plurality of detector arrays via a respective bracket.

In one embodiment, a portable imaging system comprises: a first distributed x-ray source unit, a second distributed x-ray source unit, and a third distributed x-ray source unit; a first detector array arranged directly opposite to the first distributed x-ray source unit across a central axis of the portable imaging system and releaseably coupled to the second distributed x-ray source unit and the third distributed x-ray source unit; a second detector array arranged directly opposite to the second distributed x-ray source unit across the central axis and releaseably coupled to the first distributed x-ray source unit and the third distributed x-ray source unit; and a third detector array arranged directly opposite to the third distributed x-ray source unit across the central axis and releasably coupled to the first distributed x-ray source unit and the second distributed x-ray source unit. In a first example of the portable imaging system, the first detector array releasably couples to the second distributed x-ray source unit and the third distributed x-ray source unit at a first angle relative to the second detector array and the third detector array, and the second detector array releasably couples to the first distributed x-ray source unit and the third distributed x-ray source unit at a second angle relative to the third detector array. A second example of the portable imaging system optionally includes the first example, and further includes wherein the first angle is equal to the second angle. A third example of the portable imaging system optionally includes one or both of the first and second examples, and further includes wherein the first distributed x-ray source unit, the second distributed x-ray source unit, the third distributed x-ray source unit, the first detector array, the second detector array, and the third detector array are each vertically fixed within a same imaging plane relative to a ground surface on which the portable imaging system sits. A fourth example of the portable imaging system optionally includes one or more or each of the first through third examples, and further includes wherein the first distributed x-ray source unit, the second distributed x-ray source unit, the third distributed x-ray source unit, the second detector array, and the third detector array are each supported by the first detector array in a vertical direction relative to a ground surface on which the portable imaging system sits.

In one embodiment, a method comprises: acquiring a scan of a subject via a modular imaging system by: energizing a first distributed x-ray source unit to emit x-ray radiation in a first direction and intercepting the x-ray radiation at a first detector array arranged opposite to the first distributed x-ray source unit; energizing a second distributed x-ray source unit to emit x-ray radiation in a second direction and intercepting the x-ray radiation at a second detector array arranged opposite to the second distributed x-ray source unit; and energizing a third distributed x-ray source unit to emit x-ray radiation in a third direction and intercepting the x-ray radiation at a third detector array arranged opposite to the third distributed x-ray source unit. In a first example of the method, the method further includes releasably coupling the first distributed x-ray source unit to the second detector array and the third detector array, releasably coupling the second distributed x-ray source unit to the first detector array and the third detector array, and releasably coupling the third distributed x-ray source unit to the first detector array and the second detector array. A second example of the method optionally includes the first example, and further includes: while acquiring the scan of the subject, maintaining the first distributed x-ray source unit vertically above the third detector array relative to a ground surface on which the modular imaging system sits throughout an entirety of the scan, maintaining the second distributed x-ray source unit vertically below the third detector array throughout the entirety of the can, and maintaining the third distributed x-ray source unit vertically below the second detector array throughout the entirety of the scan. A third example of the method optionally includes one or both of the first and second examples, and further includes wherein energizing the first distributed x-ray source unit includes providing electrical energy to the first distributed x-ray source unit via a portable battery unit, energizing the second distributed x-ray source unit includes providing electrical energy to the second distributed x-ray source unit via the portable battery unit, and energizing the third distributed x-ray source unit includes providing electrical energy to the third distributed x-ray source unit via the portable battery unit.

The disclosure also provides support for an imaging system, comprising: a chamber shaped to enclose a subject to be imaged, a support surface disposed within the chamber and shaped to maintain the subject in an upright position, and an annular imaging unit encircling the chamber and having a fixed angular orientation to the chamber, the annular imaging unit including a distributed x-ray source unit and a detector array arranged opposite to each other across the chamber. In a first example of the system, the distributed x-ray source unit and the detector array are arranged along an inner perimeter of the annular imaging unit. In a second example of the system, optionally including the first example, the distributed x-ray source unit includes a plurality of x-ray emitters arranged along the inner perimeter and configured to emit x-ray radiation toward a plurality of detectors of the detector array. In a third example of the system, optionally including one or both of the first and second examples, the plurality of x-ray emitters spans an angular range of at least 150 degrees around the inner perimeter. In a fourth example of the system, optionally including one or more or each of the first through third examples, the detector array includes a plurality of x-ray detectors arranged along the inner perimeter, and wherein the plurality of x-ray detectors spans an angular range of at least 180 degrees around the inner perimeter. In a fifth example of the system, optionally including one or more or each of the first through fourth examples, the detector array is configured to rotate relative to the distributed x-ray source unit. In aسixth example of the system, optionally including one or more or each of the first through fifth examples, the annular imaging unit includes a motor configured to drive the annular imaging unit parallel with a central axis of the chamber. In a seventh example of the system, optionally including one or more or each of the first through sixth examples, the support surface includes a motor configured to drive the support surface parallel with a central axis of the chamber.

The disclosure also provides support for an imaging system, comprising: a base, an outer enclosure and an inner enclosure each supported by the base, with the inner enclosure disposed within the outer enclosure and shaped to house a subject to be imaged, a subject support surface arranged within the inner enclosure in direct contact with the base, an imaging unit encircling the outer enclosure in a fixed angular orientation to the inner enclosure and including a distributed x-ray source unit and a detector array, and a cap sealing an end of the outer enclosure and an end of the inner enclosure opposite to the subject support surface. In a first example of the system, the cap includes a plurality of illumination elements configured to emit ultraviolet radiation. In a second example of the system, optionally including the first example, the base includes a plurality of openings fluidly coupling an interior of the inner enclosure to a disinfectant source. In a third example of the system, optionally including one or both of the first and second examples, the inner enclosure is fixed to the base and the outer enclosure is rotatable relative to the inner enclosure and the base. In a fourth example of the system, optionally including one or more or each of the first through third examples, the inner enclosure includes an opening shaped to receive the subject and having a first arcuate length, and the outer enclosure has a second arcuate length that is at least equal to the first arcuate length. In a fifth example of the system, optionally including one or more or each of the first through fourth examples, in a rotated configuration, the outer enclosure seals the opening of the inner enclosure. In a sixth example of the system, optionally including one or more or each of the first through fifth examples, the outer enclosure and the inner enclosure are formed from a material transparent to light having a wavelength within a range of 400-750 nanometers.

The disclosure also provides support for a method, comprising: acquiring a scan of a subject supported in an upright position by: energizing a distributed x-ray source unit of an imaging system to emit x-ray radiation across an imaging chamber housing the subject, and receiving the x-ray radiation at a detector array arranged opposite to the distributed x-ray source unit, and while acquiring the scan of the subject, maintaining an angular position of the distributed x-ray source unit relative to the imaging chamber. In a first example of the method, the method further comprises: while acquiring the scan of the subject, driving the distributed x-ray source unit and the detector array in unison in a vertical direction relative to a ground surface on which the imaging system sits. In a second example of the method, optionally including the first example, the method further comprises: while acquiring the scan of the subject, adjusting a position of the subject within the imaging chamber via a motorized subject support surface disposed entirely within the imaging chamber. In a third example of the method, optionally including one or both of the first and second examples, the method further comprises: following acquisition of the scan of the subject and while the subject is not within the imaging chamber, flowing disinfectant to the imaging chamber via a plurality of openings formed in a base supporting the imaging chamber. In a fourth example of the method, optionally including one or more or each of the first through third examples, the method further comprises: following acquisition of the scan of the subject and while the subject is not within the imaging chamber, emitting ultraviolet radiation into the imaging chamber by energizing a plurality of illumination elements of a cap sealing the imaging chamber.

The disclosure also provides support for a method for a stationary computed tomography (CT) system, comprising: activating a plurality of emitters of a stationary distributed x-ray source unit to emit x-ray beams toward an object within an imaging volume, where the x-ray source unit does not rotate around the imaging volume, receiving attenuated x-ray beams with one or more detector arrays to form a sparse view projection dataset, where each attenuated x-ray beam generates a different view, and reconstructing an image from the sparse view projection dataset using a sparse view reconstruction method. In a first example of the method, reconstructing the image from the sparse view projection dataset using the sparse view reconstruction method comprises: entering the sparse view projection dataset into a generator trained to output an artificial dense-view projection dataset, and reconstructing the image from the artificial dense-view projection dataset. In a second example of the method, optionally including the first example, the generator is trained with a discriminator operating in the image domain. In a third example of the method, optionally including one or both of the first and second examples, training the generator comprises, for a training dataset comprising a real dense-view dataset and a training sparse view dataset generated from the real dense-view dataset: entering the training sparse view dataset into the generator, reconstructing a first training image from a training artificial dense-view dataset output by the generator, reconstructing a second training image from the real dense-view dataset, entering the first and second training images into the discriminator, and updating the generator based on output from the discriminator until the discriminator cannot discriminate between the first training image and the second training image. In a fourth example of the method, optionally including one or more or each of the first through third examples, training the generator further comprises applying a loss function that compares the real dense-view dataset and the sparse view dataset or that compares the first training image to the second training image. In a fifth example of the method, optionally including one or more or each of the first through fourth examples, the sparse view projection dataset is generated from 100 views or less and the real dense-view dataset is generated from approximately 1000 views. In a sixth example of the method, optionally including one or more or each of the first through fifth examples, reconstructing the image from the sparse view projection dataset using the sparse view reconstruction method comprises reconstructing the image from the sparse view projection dataset using iterative reconstruction with one or more priors learned from one or more deep learning networks, where each update stage of the iterative reconstruction includes a datafit update and a deep learning update. In a seventh example of the method, optionally including one or more or each of the first through sixth examples, reconstructing the image from the sparse view projection dataset using the sparse view reconstruction method comprises: entering the sparse view projection dataset into a deep learning network trained to output a first initial reconstructed image, regularizing the first initial reconstructed image using compressed sensing to generate a second initial reconstructed image, updating the sparse view projection dataset based on an analytic mapping between the first initial reconstructed image and the second initial reconstructed image, entering the updated sparse view projection dataset into the deep learning network to generate a third initial reconstructed image, and iteratively refining the third initial reconstructed image based on the second initial reconstructed image to form a final reconstructed image. In an eighth example of the method, optionally including one or more or each of the first through seventh example, reconstructing the image from the sparse view projection dataset using the sparse view reconstruction method comprises: backprojecting each view of the sparse view projection dataset to generate a separate single-view backprojection for each view, and entering each single-view backprojection as input to a deep learning network trained to output the image. In a ninth example of the method, optionally including one or more or each of the first through eighth examples, reconstructing the image from the sparse view projection dataset using the sparse view reconstruction method comprises reconstructing the image from the sparse view projection dataset using a hierarchical reconstruction method that comprises: partitioning the sparse view projection dataset into a plurality of densely-sampled view sets, entering each densely-sampled view set into a network trained to output a respective single view for each densely-sampled view set, and reconstructing the image from each respective single view. In a tenth example of the method, optionally including one or more or each of the first through ninth examples, the method further comprises: prior to reconstructing the image, entering the sparse view projection dataset into a network trained to extrapolate missing views in a view angle direction to form an extrapolated sparse view projection dataset, and reconstructing the image from the extrapolated sparse view projection dataset. In a eleventh example of the method, optionally including one or more or each of the first through tenth examples, reconstructing the image from the sparse view projection dataset using the sparse view reconstruction method comprises: partitioning the sparse view projection dataset into time-resolved subsets of views, separately reconstructing each time-resolved subset of views to generate a set of reconstructions, estimating motion of the object based on the set of reconstructions, and applying a motion correction to the image based on the estimated motion, where the image is reconstructed from the sparse view projection dataset or the image is generated from the set of reconstructions. In a twelfth example of the method, optionally including one or more or each of the first through eleventh examples, reconstructing the image from the sparse view projection dataset using the sparse view reconstruction method comprises: partitioning the sparse view projection dataset into a first dataset comprising output from detector elements of the one or more detector arrays positioned to intercept x-ray beams emitted from a first subset of emitters of the plurality of emitters and a second dataset comprising output from detector elements of the one or more detector arrays positioned to intercept x-ray beams emitted from a second subset of emitters of the plurality of emitters, the first set of emitters having larger focal spots than the second set of emitters, reconstructing a first image from the first dataset using the sparse view reconstruction method, reconstructing a second image from the second dataset using the sparse view reconstruction method, and combining the first image and the second image to form the image.

The disclosure also provides support for a stationary computed tomography (CT) system, comprising: an imaging unit comprising: one or more stationary distributed x-ray source units each comprising a plurality of emitters positioned to emit x-ray beams through an imaging volume, where the one or more x-ray source units do not rotate around the imaging volume, and one or more detector arrays extending around at least a portion of the imaging volume, each detector array comprising a plurality of detector elements, and one or more computing devices configured to, during a scan of an object within the imaging volume: translate the imaging unit vertically along the object, activate each plurality of emitters, sample each plurality of detector elements to obtain a projection dataset, and reconstruct one or more images from the projection dataset using sparse view reconstruction method. In a first example of the method, reconstructing the one or more images from the projection dataset using the sparse view reconstruction method comprises: partitioning the projection dataset into time-resolved subsets of views, separately reconstructing each time-resolved subset of views to generate a set of reconstructions, estimating motion of the object based on the set of reconstructions, and applying a motion correction to an image of the one or more images based on the estimated motion, where the image is reconstructed from the projection dataset or the image is generated from the set of reconstructions. In a second example of the method, optionally including the first example, reconstructing the one or more images from the projection dataset using the sparse view reconstruction method comprises: partitioning the projection dataset into a first dataset comprising output from detector elements positioned to intercept x-ray beams emitted from a first subset of emitters and a second dataset comprising output from detector elements positioned to intercept x-ray beams emitted from a second subset of emitters, the first subset of emitters having larger focal spots than the second subset of emitters, reconstructing a first image from the first dataset using the sparse view reconstruction method, reconstructing a second image from the second dataset using the sparse view reconstruction method, and combining the first image and the second image to form a final image.

The disclosure also provides support for a method for a stationary computed tomography (CT) system, comprising: generating a sparse view projection dataset by activating a plurality of emitters of a stationary distributed x-ray source unit to emit x-ray beams toward an object within an imaging volume, where the x-ray source unit does not rotate around the imaging volume, and receiving attenuated x-ray beams with one or more detector arrays, the sparse view projection dataset differing from a dense view projection dataset in one or more of a total number of views, a spacing of views, a view angle range, and a field of view, and reconstructing an image from the sparse view projection dataset using a sparse view reconstruction method that includes a deep learning network trained with training data that includes: the dense view projection dataset and/or one or more training images generated from the dense view projection dataset, and a pseudo sparse view projection dataset generated from the dense view projection dataset and/or one more training images generated from the pseudo sparse view projection dataset, where the pseudo sparse view projection dataset is generated by discarding a plurality of views of the dense view projection dataset so that a total number of views, a spacing of views, a view angle range, and a field of view of the pseudo sparse view projection dataset matches the total number of views, the spacing of views, the view angle range, and the field of view of the sparse view projection dataset. In a first example of the method, the total number of views of the sparse view projection dataset is 100 views or less and the view angle range of the sparse view projection dataset is less than 180 degrees. In a second example of the method, optionally including the first example, spacing of views of the sparse view projection dataset is non-uniform. In a third example of the method, optionally including one or both of the first and second examples, reconstructing the image from the sparse view projection dataset using the sparse view reconstruction method comprises: backprojecting each view of the sparse view projection dataset to generate a separate single-view backprojection for each view, entering each single-view backprojection as input to the deep learning network, and receiving the image as output from the deep learning network.

The disclosure also provides support for a stationary computed tomography (CT) system, comprising: a stationary distributed x-ray source unit comprising a plurality of emitters positioned to emit x-ray beams through an imaging volume, one or more detector arrays extending around at least a portion of the imaging volume, each detector array comprising a plurality of detector elements, each detector element configured to receive x-ray beams from more than one emitter, and an anti-scatter device configured to be positioned between one or more emitters of the plurality of emitters and an object in the imaging volume. In a first example of the system, each emitter is configured to emit a respective x-ray beam having a full fan-beam and wherein the anti-scatter device comprises a plurality of collimators each configured to truncate a corresponding x-ray beam to form a partial fan-beam. In a second example of the system, optionally including the first example, the plurality of emitters includes a first emitter, a second emitter, and a third emitter, and wherein the plurality of collimators comprises a first collimator, a second collimator, and a third collimator, the first collimator positioned proximate the first emitter and configured to truncate a first x-ray beam emitted from the first emitter to form a first partial fan-beam having a first angular range, the second collimator positioned proximate the second emitter and configured to truncate a second x-ray beam emitted from the second emitter to form a second partial fan-beam having a second angular range, and the third collimator positioned proximate the third emitter and configured to truncate a third x-ray beam emitted from the third emitter to form a third partial fan-beam having a third angular range, the first angular range different than the second angular range and the third angular range and the second angular range different than the third angular range. In a third example of the system, optionally including one or both of the first and second examples, the x-ray source unit comprises an x-ray source ring encircling the imaging volume with the plurality of emitters positioned around the x-ray source ring, and wherein the anti-scatter device comprises a first plurality of collimators positioned around a first ring-shaped actuator and a second plurality of collimators positioned around a second ring-shaped actuator, and wherein the first ring-shaped actuator and the second ring-shaped actuator are movable to truncate one or more x-ray beams to form one or more partial fan-beams. In a fourth example of the system, optionally including one or more or each of the first through third examples, each emitter is configured to emit a respective x-ray beam having a full fan-beam and wherein the anti-scatter device comprises a plurality of collimators each configured to break up a corresponding full fan-beam into a series of narrower fan-beams. In a fifth example of the system, optionally including one or more or each of the first through fourth examples, the one or more detector arrays and the x-ray source unit are displaced along a z-axis of the imaging volume, wherein each emitter is configured to emit a respective x-ray beam having a full fan-beam, and wherein the anti-scatter device comprises one or more collimators each positionable to collimate a corresponding full fan-beam along the z-axis to form a collimated fan-beam that impinges on some but not all of a subset of detector elements of the one or more detector arrays along the z-axis. In a sixth example of the system, optionally including one or more or each of the first through fifth examples, the system further comprises: a computing device configured to determine an amount of scatter based on output from the subset of the detector elements along the z-axis and correct output from all of the plurality of detector elements based on the amount of scatter. In a seventh example of the system, optionally including one or more or each of the first through sixth examples, the system further comprises: a source controller for triggering the plurality of emitters to emit the x-ray beams. In an eighth example of the system, optionally including one or more or each of the first through seventh examples, at least a portion the emitters of the plurality of emitters are triggered simultaneously. In a ninth example of the system, optionally including one or more or each of the first through eighth examples, each emitter of the plurality of emitters is triggered separately. In a tenth example of the system, optionally including one or more or each of the first through ninth examples, the system further comprises: a computing device configured to reconstruct one or more images from projection data acquired by the one or more detector arrays upon the plurality of emitters being triggered to emit the x-ray beams. In a eleventh example of the system, optionally including one or more or each of the first through tenth examples, when the plurality of emitters is triggered, the x-ray source does not rotate around the imaging volume. In a twelfth example of the system, optionally including one or more or each of the first through eleventh examples, the x-ray source unit and the one or more detector arrays form an imaging unit configured to translate vertically along the imaging volume when the plurality of emitters is triggered.

The disclosure also provides support for a method for a stationary computed tomography (CT) system, comprising: activating a plurality of emitters of a stationary distributed x-ray source unit to emit x-ray beams toward an object within an imaging volume, where the x-ray source unit does not rotate around the imaging volume, collimating at least a portion of the x-ray beams to reduce scatter via an anti-scatter device positioned between the x-ray source unit and the object, receiving attenuated x-ray beams with one or more detector arrays, and reconstructing one or more images from projection data obtained from the one or more detector arrays. In a first example of the method, the x-ray source unit and the one or more detector arrays form an imaging unit, and further comprising translating the imaging unit vertically along the imaging volume while the plurality of emitters is activated. In a second example of the method, optionally including the first example, collimating at least the portion of the x-ray beams comprises collimating a first x-ray beam emitted by a first emitter of the plurality of emitters to have a partial fan-beam with a first angular range and collimating a second x-ray beam emitted by a second emitter of the plurality of emitters to have a partial fan-beam with a second angular range that is different than the first angular range. In a third example of the method, optionally including one or both of the first and second examples, collimating the first x-ray beam and collimating the second x-ray beam comprises adjusting a positon of a first ring-shaped actuator including a first plurality of collimators and/or adjusting a positon of a second ring-shaped actuator including a second plurality of collimators. In a fourth example of the method, optionally including one or more or each of the first through third examples, collimating at least the portion of the x-ray beams comprises collimating a first x-ray beam emitted by a first emitter of the plurality of emitters to form two or more partial fan-beams.

The disclosure also provides support for a stationary computed tomography (CT) system, comprising: an imaging unit comprising: a stationary distributed x-ray source unit comprising a plurality of emitters positioned to emit x-ray beams through an imaging volume, where the x-ray source unit does not rotate around the imaging volume, one or more detector arrays extending around at least a portion of the imaging volume, each detector array comprising a plurality of detector elements, and an anti-scatter device comprising a plurality of collimators, wherein each x-ray beam is configured to be collimated by one or more collimators of the plurality of collimators, and one or more computing devices configured to, during a scan of an object within the imaging volume, translate the imaging unit vertically along the object, activate the plurality of emitters, sample the plurality of detector elements to obtain projection data, and reconstruct one or more images from the projection data.

The disclosure also provides support for a method for a stationary computed tomography (CT) system, comprising: activating an emitter of a plurality of emitters of a stationary distributed x-ray source unit to emit an x-ray beam toward an object within an imaging volume, where the x-ray source unit does not rotate around the imaging volume, receiving the x-ray beam at a subset of detector elements of a plurality of detector elements of one or more detector arrays, sampling the plurality of detector elements to generate a total transmission profile, an attenuation profile, and a scatter measurement, generating a scatter-corrected attenuation profile by entering the total transmission profile, the attenuation profile, and the scatter measurement as inputs to a model, and reconstructing one or more images from the scatter-corrected attenuation profile. In a first example of the method, the total transmission profile is generated from detector output from each detector element of the plurality of detector elements, the attenuation profile is generated from output from only the subset of detector elements, and the scatter measurement is generated from output from only one or more detector elements of the plurality of detector elements outside the x-ray beam. In a second example of the method, optionally including the first example, the model is trained to output the scatter-corrected attenuation profile. In a third example of the method, optionally including one or both of the first and second examples, the model is trained to output a scatter profile representing scatter of the x-ray beam detected by the plurality of detector elements, and wherein generating the scatter-corrected attenuation profile comprises correcting the attenuation profile with the scatter profile to generate the scatter-corrected attenuation profile. In a fourth example of the method, optionally including one or more or each of the first through third examples, the model is trained with training data pairs comprising, for a given view, scatter-corrupted data and scatter-reduced data. In a fifth example of the method, optionally including one or more or each of the first through fourth examples, the scatter-corrupted data is acquired with a full fan-beam x-ray beam and the scatter-reduced data is acquired with a partial fan-beam x-ray beam. In a sixth example of the method, optionally including one or more or each of the first through fifth examples, the scatter-corrected attenuation profile represents a first view, and further comprising activating one or more additional emitters of the plurality of emitters to generate one or more additional attenuation profiles each representing a respective different additional view, scatter-correcting each additional attenuation profile based on the scatter-corrected attenuation profile via interpolation to generate one or more additional scatter-corrected attenuation profiles, and wherein reconstructing one or more images from the scatter-corrected attenuation profile comprises reconstructing one or more images from the scatter-corrected attenuation profile and the one or more additional scatter-corrected attenuation profiles.

The disclosure also provides support for a stationary computed tomography (CT) system, comprising: a stationary distributed x-ray source unit comprising a plurality of emitters positioned to emit x-ray beams toward an object in an imaging volume, a plurality of detector elements forming one or more detector arrays extending around at least a portion of the imaging volume, and one or more computing devices configured to: activate a first emitter of the plurality of emitters to emit a first x-ray beam shaped and positioned to be intercepted by a subset of detector elements of the plurality of detector elements, measure scatter of the first x-ray beam caused by the object, activate one or more additional emitters of the plurality of emitters to emit one or more additional x-ray beams shaped and positioned to be intercepted by one or more additional subsets of detector elements of the plurality of detector elements, obtain projection data from the subset of detector elements and the one or more additional subsets of detector elements, correct the projection data with the measured scatter to form scatter-corrected projection data, and reconstruct one or more images from the scatter-corrected projection data. In a first example of the system, the first emitter is configured to emit the first x-ray beam with a fan-beam spanning the subset of detector elements, and further comprising a lead blocker positioned proximate the first emitter, the lead blocker configured to attenuate a portion of the first x-ray beam in a center of the fan-beam such that a portion of detector elements within the subset of detector elements do not intercept the first x-ray beam, and wherein the scatter of the first x-ray beam caused by the object is measured by the portion of the detector elements that do not intercept the first x-ray beam. In a second example of the system, optionally including the first example, the scatter of the first x-ray beam is measured by one or more detector elements outside the subset of detector elements that are not positioned to intercept the first x-ray beam. In a third example of the system, optionally including one or both of the first and second examples, the system further comprises: a modulator positioned proximate the first emitter, the modulator comprising a plurality of attenuating blockers configured to attenuate portions of the first x-ray beam while not attenuating other portions of the first x-ray beam, and wherein the one or more computing devices are configured to measure the scatter of the first x-ray beam by sampling the output from the subset of the detector elements and demodulating the sampled output to separate detector signals resulting from interception of the first x-ray beam and detector signals resulting from interception of the scatter. In a fourth example of the system, optionally including one or more or each of the first through third examples, correcting the projection data with the measured scatter to form scatter-corrected projection data comprises entering the measured scatter and projection data from the subset of detector elements into a model trained to provide a scatter estimation, and correcting the projection data from the subset of detector elements and the one or more additional subsets of detector elements with the scatter estimation. In a fifth example of the system, optionally including one or more or each of the first through fourth examples, correcting the projection data with the measured scatter to form scatter-corrected projection data comprises entering the measured scatter and projection data from the subset of detector elements into a model trained to provide scatter-corrected projection data, and correcting projection data from the one or more additional subsets of detector elements based on the scatter-corrected projection data via interpolation.

The disclosure also provides support for a method for a stationary computed tomography (CT) system, comprising: obtaining a plurality of views of projection data by sequentially activating a plurality of emitters of a stationary distributed x-ray source unit to emit a plurality of x-ray beams toward an object within an imaging volume and intercepting the plurality of x-ray beams, after attenuation by the object, at a plurality of detector elements of one or more detector arrays, for a first view of the plurality of views obtained by activating a first emitter of the plurality of emitters to emit a primary x-ray beam, generating a transmission profile, an attenuation profile, and a scatter measurement based on output from the plurality of detector elements, where the attenuation profile includes output from only detector elements positioned to intercept the primary x-ray beam, the scatter measurement includes output from only detector elements positioned outside of the primary x-ray beam, and the transmission profile includes output from detector elements positioned to intercept the primary x-ray beam and detector elements positioned outside of the primary x-ray beam, entering the transmission profile, the attenuation profile, and the scatter measurement into a model trained to output a scatter profile indicative of an amount of scattered x-ray beams received at the detector elements positioned to intercept the primary x-ray beam, correcting the projection data of the first view and each remaining view based on the scatter profile, and reconstructing an image from the corrected projection data. In a first example of the method, the x-ray source unit and the one or more detector arrays form an imaging unit, and further comprising vertically translating the imaging unit while the plurality of emitters are sequentially activated. In a second example of the method, optionally including the first example, reconstructing the image includes reconstructing the image using a sparse view reconstruction method. In a third example of the method, optionally including one or both of the first and second examples, a lead blocker is positioned proximate the first emitter such that the primary x-ray beam is split into two separate x-ray beams and wherein the detector elements positioned outside of the primary x-ray beam include detector elements positioned opposite the lead blocker such that the detector elements positioned to intercept the primary x-ray beam are positioned on either side of the detector elements positioned outside of the primary x-ray beam.

The disclosure also provides support for a stationary computed tomography (CT) system, comprising: one or more detector arrays extending around at least a portion of an imaging volume, a stationary distributed x-ray source unit, the x-ray source unit comprising a plurality of emitters including a first set of emitters configured to operate at a first voltage and a second set of emitters configured to operate at a second voltage, different than the first voltage, and a source controller for triggering the first set of emitters for acquiring first projection data by the one or more detector arrays and triggering the second set of emitters for acquiring second projection data by the one or more detector arrays, the first projection data and the second projection data usable to reconstruct one or more basis material composition images or monochromatic images of an object within the imaging volume. In a first example of the system, the one or more detector arrays comprise a detector ring that encircles the imaging volume and the x-ray source unit comprises a first segment and a second segment, the first set of emitters positioned in the first segment and the second set of emitters positioned in the second segment, the first segment forming a first semi-circle partially encircling the imaging volume and the second segment forming a second semi-circle partially encircling the imaging volume. In a second example of the system, optionally including the first example, the one or more detector arrays comprise a detector ring that encircles the imaging volume and the x-ray source unit comprises a first x-ray source ring and a second x-ray source ring each encircling the imaging volume, the first set of emitters positioned in the first x-ray source ring and the second set of emitters positioned in the second x-ray source ring. In a third example of the system, optionally including one or both of the first and second examples, the one or more detector arrays comprise a first detector array and a second detector array, wherein the x-ray source unit comprises a first segment positioned opposite the imaging volume from the first detector array and a second segment positioned opposite the imaging volume from the second detector array, and wherein the first set of emitters is positioned in the first segment and the second set of emitters is positioned in the second segment. In a fourth example of the system, optionally including one or more or each of the first through third examples, the system further comprises: a third detector array and a third segment of the x-ray source unit, the third segment positioned opposite the imaging volume from the third detector array, and wherein the third segment includes a third set of emitters configured to operate at a third voltage, different than the first voltage and the second voltage. In a fifth example of the system, optionally including one or more or each of the first through fourth examples, the one or more detector arrays comprise a detector ring that encircles the imaging volume and the x-ray source comprises an x-ray source ring encircling the imaging volume, the first set of emitters and the second set of emitters positioned in an alternating fashion around the x-ray source ring. In a sixth example of the system, optionally including one or more or each of the first through fifth examples, when the first set of emitters and the second set of emitters are triggered, the x-ray source unit does not rotate around the imaging volume and the one or more detector arrays rotate around the imaging volume. In a seventh example of the system, optionally including one or more or each of the first through sixth examples, at least a portion the emitters of the plurality of emitters are triggered simultaneously. In an eighth example of the system, optionally including one or more or each of the first through seventh examples, the system further comprises: a computing device configured to reconstruct one or more first images from the first projection data, reconstruct one or more second images from the second projection data, and generate the one or more basis material composition images or monochromatic images from the one or more first images and the one or more second images via a decomposition process. In a ninth example of the system, optionally including one or more or each of the first through eighth examples, the first projection data comprises a first set of views including a first view and the second projection data comprises a second set of views including a second view adjacent to the first view, and further comprising a computing device configured to enter the first view and the second view as input to a network trained to output a joint view, the one or more basis material composition images or monochromatic images reconstructed from the joint view. In a tenth example of the system, optionally including one or more or each of the first through ninth examples, the system further comprises: a first generator coupled to the first set of emitters and configured to supply the first voltage and a second generator coupled to the second set of emitters and configured to supply the second voltage.

The disclosure also provides support for a stationary computed tomography (CT) system, comprising: one or more detector arrays extending around at least a portion of an imaging volume, a stationary distributed x-ray source unit, the x-ray source unit comprising a plurality of emitters configured to be switched between a first voltage and a second voltage, different than the first voltage, and a source controller for triggering the plurality of emitters at the first voltage for acquiring first projection data by the one or more detector arrays and triggering the plurality of emitters at the second voltage for acquiring second projection data by the one or more detector arrays, the first projection data and the second projection data usable to reconstruct one or more basis material composition images or monochromatic images of an object within the imaging volume. In a first example of the system, the first projection data and the second projection data are acquired sequentially, such that the source controller is configured to first trigger each emitter of the plurality of emitters at the first voltage to acquire the first projection data and then trigger each emitter of the plurality of emitters at the second voltage to acquire the second projection data. In a second example of the system, optionally including the first example, the first projection data and the second projection data are acquired in an interleaved manner, such that the source controller is configured to trigger a first emitter of the plurality of emitters at the first voltage and then switch the first emitter to the second voltage, and then trigger a second emitter of the plurality of emitters at the first voltage and then switch the second emitter to the second voltage. In a third example of the system, optionally including one or both of the first and second examples, the system further comprises: a dynamic resonance energy-recovery generator coupled to the x-ray source unit. In a fourth example of the system, optionally including one or more or each of the first through third examples, each emitter comprises a cathode and an anode, each anode configured to be held at the first voltage and each cathode configured to be switched from a negative voltage to ground in order to switch that emitter to the second voltage. In a fifth example of the system, optionally including one or more or each of the first through fourth examples, at least a portion of the emitters of the plurality of emitters are triggered simultaneously.

The disclosure also provides support for a method for a stationary computed tomography (CT) system, comprising: activating a plurality of emitters of a stationary distributed x-ray source unit at a first voltage and at a second voltage to emit x-ray beams of a first energy and to emit x-ray beams of a second energy toward an object within an imaging volume, where the x-ray source unit does not rotate around the imaging volume, receiving attenuated x-ray beams at the first energy and the second energy with one or more detector arrays, and reconstructing one or more images from projection data obtained from the one or more detector arrays. In a first example of the method, activating the plurality of emitters at the first voltage and the second voltage comprises activating a first set of emitters of the plurality of emitters at the first voltage to emit x-ray beams of the first energy and activating a second set of emitters of the plurality of emitters at the second voltage to emit x-ray beams of the second energy. In a second example of the method, optionally including the first example, reconstructing the one or more images from the projection data comprises: reconstructing one or more first images from first projection data obtained while x-ray beams of the first energy are emitted, reconstructing one or more second images from second projection data obtained while x-ray beams of the second energy are emitted, and generating one or more basis material composition images or monochromatic images from the one or more first images and the one or more second images via a decomposition process.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A stationary computed tomography (CT) system, comprising:
   a plurality of stationary distributed x-ray source units each comprising a plurality of emitters positioned to emit x-ray beams through an imaging volume; and
   a plurality of detector arrays extending around at least a portion of the imaging volume, each detector array comprising a plurality of detector elements, each detector element configured to receive x-ray beams from more than one emitter, wherein the plurality of detector arrays and the plurality of stationary distributed x-ray source units are displaced along a z-axis of the imaging volume, and wherein each stationary distributed x-ray source unit is arranged between two of the detector arrays and each detector array is arranged between two of the stationary distributed x-ray source units.

2. The stationary CT system of claim 1, wherein each emitter is configured to emit a respective x-ray beam having a full fan-beam and wherein the anti-scatter device comprises a plurality of collimators each configured to truncate a corresponding x-ray beam to form a partial fan-beam.

3. The stationary CT system of claim 2, wherein the plurality of emitters includes a first emitter, a second emitter, and a third emitter, and wherein the plurality of collimators comprises a first collimator, a second collimator, and a third collimator, the first collimator positioned proximate the first emitter and configured to truncate a first x-ray beam emitted from the first emitter to form a first partial fan-beam having a first angular range, the second collimator positioned proximate the second emitter and configured to truncate a second x-ray beam emitted from the second emitter to form a second partial fan-beam having a second angular range, and the third collimator positioned proximate the third emitter and configured to truncate a third x-ray beam emitted from the third emitter to form a third partial fan-beam having a third angular range, the first angular range different than the second angular range and the third angular range and the second angular range different than the third angular range.

4. The stationary CT system of claim 1, wherein the x-ray source unit comprises an x-ray source ring encircling the imaging volume with the plurality of emitters positioned around the x-ray source ring, and wherein the anti-scatter device comprises a first plurality of collimators positioned around a first ring-shaped actuator and a second plurality of collimators positioned around a second ring-shaped actuator, and wherein the first ring-shaped actuator and the second ring-shaped actuator are movable to truncate one or more x-ray beams to form one or more partial fan-beams.

5. The stationary CT system of claim 1, wherein each emitter is configured to emit a respective x-ray beam having a full fan-beam and wherein the anti-scatter device comprises a plurality of collimators each configured to break up a corresponding full fan-beam into a series of narrower fan-beams.

6. The stationary CT system of claim 1, wherein each emitter is configured to emit a respective x-ray beam having a full fan-beam.

7. The stationary CT system of claim 6, wherein the anti-scatter device comprises one or more collimators each positionable to collimate a corresponding full fan-beam along the z-axis to form a collimated fan-beam that impinges on some but not all of a subset of detector elements of the one or more detector arrays along the z-axis.

8. The stationary CT system of claim 7, further comprising a computing device configured to determine an amount of scatter based on output from the subset of the detector elements along the z-axis and correct output from all of the plurality of detector elements based on the amount of scatter.

9. The stationary CT system of claim 1, further comprising a source controller for triggering the plurality of emitters to emit the x-ray beams.

10. The stationary CT system of claim 9, wherein at least a portion the emitters of the plurality of emitters are triggered simultaneously.

11. The stationary CT system of claim 9, wherein each emitter of the plurality of emitters is triggered separately.

12. The stationary CT system of claim 9, further comprising a computing device configured to reconstruct one or more images from projection data acquired by the one or more detector arrays upon the plurality of emitters being triggered to emit the x-ray beams.

13. The stationary CT system of claim 9, wherein when the plurality of emitters is triggered, the x-ray source does not rotate around the imaging volume.

14. The stationary CT system of claim 13, wherein the x-ray source unit and the one or more detector arrays form an imaging unit configured to translate vertically along the imaging volume when the plurality of emitters is triggered.

15. The stationary CT system of claim 1, wherein the plurality of stationary distributed x-ray source units includes three stationary distributed x-ray source units and the plurality of detector arrays includes three detector arrays, and further wherein the three stationary distributed x-ray source units and the three detector arrays are each arranged at a side of a hexagonal profile.

16. A method for a stationary computed tomography (CT) system, comprising:
activating a plurality of emitters of each of a plurality of stationary distributed x-ray source units to emit x-ray beams toward an object within an imaging volume, where each stationary distributed x-ray source unit does not rotate around the imaging volume;
receiving attenuated x-ray beams with a plurality of detector arrays; and
reconstructing one or more images from projection data obtained from the plurality of detector arrays, wherein the plurality of stationary distributed x-ray source units and the plurality of detector arrays form an imaging unit, and further comprising translating the imaging unit vertically along the imaging volume while each plurality of emitters is activated, wherein each stationary distributed x-ray source unit is arranged between two of the detector arrays and each detector array is arranged between two of the stationary distributed x-ray source units.

17. The method of claim 16, wherein collimating at least the portion of the x-ray beams comprises collimating a first x-ray beam emitted by a first emitter of the plurality of emitters to have a partial fan-beam with a first angular range and collimating a second x-ray beam emitted by a second emitter of the plurality of emitters to have a partial fan-beam with a second angular range that is different than the first angular range.

18. The method of claim 17, wherein collimating the first x-ray beam and collimating the second x-ray beam comprises adjusting a positon of a first ring-shaped actuator including a first plurality of collimators and/or adjusting a positon of a second ring-shaped actuator including a second plurality of collimators.

19. The method of claim 16, wherein collimating at least the portion of the x-ray beams comprises collimating a first x-ray beam emitted by a first emitter of the plurality of emitters to form two or more partial fan-beams.

20. A stationary computed tomography (CT) system, comprising:
an imaging unit comprising:
a plurality of stationary distributed x-ray source units each comprising a plurality of emitters positioned to emit x-ray beams through an imaging volume, where each stationary distributed x-ray source unit does not rotate around the imaging volume; and
a plurality of detector arrays extending around at least a portion of the imaging volume, each detector array comprising a plurality of detector elements, wherein each stationary distributed x-ray source unit is arranged between two of the detector arrays and each detector array is arranged between two of the stationary distributed x-ray source units; and
one or more computing devices configured to, during a scan of an object within the imaging volume, translate the imaging unit vertically along the object, activate each plurality of emitters, sample each plurality of detector elements to obtain projection data, and reconstruct one or more images from the projection data.

* * * * *